(12) United States Patent
Chen et al.

(10) Patent No.: US 8,685,647 B2
(45) Date of Patent: Apr. 1, 2014

(54) SNP MARKERS ASSOCIATED WITH POLYCYSTIC OVARY SYNDROME

(75) Inventors: Zi-Jiang Chen, Shandong (CN); Han Zhao, Shandong (CN); Lin He, Shanghai (CN); Yongyong Shi, Shanghai (CN); Jinlong Ma, Shandong (CN); Yueran Zhao, Shandong (CN); Ling Geng, Shandong (CN); Li You, Shandong (CN)

(73) Assignees: Shandong University, Jinan Shandong (CN); Shandong Shanda Hospital for Reproductive Medicine Co., Ltd., Jinan Shandong (CN); Shanghai Jiao Tong University, Shanghai (CN)

( * ) Notice: Subject to any disclaimer, the term of this patent is extended or adjusted under 35 U.S.C. 154(b) by 0 days.

(21) Appl. No.: 13/525,774

(22) Filed: Jun. 18, 2012

(65) Prior Publication Data

US 2012/0309642 A1 Dec. 6, 2012

Related U.S. Application Data

(63) Continuation-in-part of application No. PCT/CN2010/073387, filed on May 31, 2010.

(51) Int. Cl.
*C12Q 1/68* (2006.01)
*C40B 30/04* (2006.01)

(52) U.S. Cl.
USPC ............... 435/6.11; 435/6.1; 435/6.12; 506/9

(58) Field of Classification Search
None
See application file for complete search history.

(56) References Cited

FOREIGN PATENT DOCUMENTS

| KR | 10-2004-0074800 A | 8/2004 |
|---|---|---|
| WO | 2006/125513 | 11/2006 |
| WO | WO 2008/112898 A2 * | 9/2008 |

OTHER PUBLICATIONS

Rotterdam ESHRE/ASRM-Sponsored PCOS Consensus Workshop Group, "Revised 2003 consensus on diagnostic criteria and long-term health risks related to polycystic ovary syndrome", Fertility and Sterility, vol. 81, No. 1, Jan. 2004; pp. 19-25.
Goodarzi, "Diagnosis, epidemiology, and genetics of the polycystic ovary syndrome", Best Practice & Research Clinical Endocrinology & Metabolism, vol. 20, No. 2, 2006, pp. 193-205.
Ehrmann et al., "Prevalence of Impaired Glucose Tolerance and Diabetes in Women With Polycystic Ovary Syndrome", Diabetes Care, vol. 22, No. 1, Jan. 1999, pp. 141-146.
Carmina, "Cardiovascular risk and events in polycystic ovary syndrome", Climacteric, 2009; 12 (Suppl 1), pp. 22-25.
Kandaraki et al., "Metabolic syndrome and polycystic ovary syndrome . . . and vice versa", Arq Bras Endocrinol Metabol, 2009; 53/2, pp. 227-237.
Wild et al., "Long-term consequences of polycystic ovary syndrome: results of a 31 year follow-up study", Human Fertility, 3, 2000, pp. 101-105.
Legro et al., "Detecting Insulin Resistance in Polycystic Ovary Syndrome: Purposes and Pitfalls", Obstetrical and Gynecological Survey, vol. 59, No. 2, 2004, pp. 141-154.
Espinós-Gómez et al., "Prevalence and predictors of abnormal glucose metabolism in Mediterranean women with polycystic ovary syndrome", Gynecological Endocrinology, 25(3), Mar. 2009; pp. 199-204.
Kulshreshtha et al., "Insulin response to oral glucose in healthy, lean young women and patients with polycystic ovary syndrome", Gynecological Endocrinology, 24(11), Nov. 2008, pp. 637-643.
Shi et al., "Analysis of clinical characteristics in large-scale Chinese women with polycystic ovary syndrome", Neuroendocrinology Letters, vol. 28, No. 6, 2007, pp. 807-810.
Sudo et al., "Genetic and functional analyses of polymorphisms in the human FSH receptor gene", Molecular Human Reproduction, vol. 8, No. 10, 2002, pp. 893-899.
Gaasenbeek et al., "Large-Scale Analysis of the Relationship between *CYP11A* Promoter Variation, Polycystic Ovarian Syndrome, and Serum Testosterone", The Journal of Clinical Endocrinology & Metabolism, 89(5), 2004, pp. 2408-2413.
Wang et al., A microsatellite polymorphism (tttta)n in the promoter of the CYP11a gene in Chinese women with polycystic ovary syndrome, Fertility and Sterility, vol. 86, No. 1, Jul. 2006, pp. 223-226.
Chen et al., "Correlation between single nucleotide polymorphism of insulin receptor gene with polycystic ovary syndrome", China J Obstet Gynecol, vol. 39, No. 9, Sep. 2004, pp. 582-585 with English translation.
Villuendas et al., "The -597 G→A and -174 G→C Polymorphisms in the Promoter of the IL-6 Gene Are Associated with Hyperandrogenism", The Journal of Clinical Endocrinology & Metabolism, 87(3), Mar. 2002, pp. 1134-1141.
Simoni et al., Functional genetic polymorphisms and female reproductive disorders: Part I: Polycystic ovary syndrome and ovarian response, Human Reproduction Update, vol. 14, No. 5, Jul. 2008, pp. 459-484.
Li et al., "MaCH: Using Sequence and Genotype Data to Estimate Haplotypes and Unobserved Genotypes", Genet Epidemiol., 34(8), Dec. 2010, pp. 816-834.
Li et al., "Genotype Imputation", Annual Review of Genomics and Human Genetics, 10, 2009, pp. 387-406.
Marchini et al., "A new multipoint method for genome-wide association studies by imputation of genotypes", Nature genetics, vol. 39, No. 7, Jul. 2007, pp. 906-913.
Howie et al., "A Flexible and Accurate Genotype Imputation Method for the Next Generation of Genome-Wide Association Studies", PLoS Genetics, vol. 5, Issue 6, e1000529, Jun. 2009, 15 pages.

(Continued)

*Primary Examiner* — Samuel Woolwine
*Assistant Examiner* — Kaijiang Zhang
(74) *Attorney, Agent, or Firm* — Renner, Otto, Boisselle & Sklar, LLP

(57) ABSTRACT

The present invention discloses SNP markers associated with PCOS and provides probes, chips, primers, kits and methods for detecting the SNP markers. Furthermore, the present invention relates to the use of SNPs in predicting or diagnosing the risk of PCOS.

10 Claims, 9 Drawing Sheets

(56) References Cited

OTHER PUBLICATIONS

Price et al., "Principal components analysis corrects for stratification in genome-wide association studies", Nature genetics, vol. 38, Vo. 8, Aug. 2006, pp. 904-909.

Lindgren et al., Genome-Wide Association Scan Meta-Analysis Identifies Three Loci Influencing Adiposity and Fat Distribution, PLoS Genetics, Vo. 5, Issue 6, e1000508, Jun. 2009, 13 pages.

Purcell et al., "PLINK: A Tool Set for Whole-Genome Association and Population-Based Linkage Analyses", The American Journal of Human Genetics, vol. 81, Sep. 2007, pp. 559-575.

Pruim et al., "LocusZoom: regional visualization of genome-wide association scan results", Bioinformatics Applications Note, vol. 26, No. 18, 2010, pp. 2336-2337.

Shi et al., SHEsis, a powerful software platform for analyses of linkage disequilibrium, haplotype construction, and genetic association at polymorphism loci, Cell Research, 15(2), Feb. 2005, pp. 97-98.

Chen et al., "Genome-wide association study identifies susceptibility loci for polycystic ovary syndrome on chromosome 2p16.3, 2p21 and 9q33.3", Nature Genetics, vol. 43, No. 1, Jan. 2011, pp. 55-59.

Petukhova et al., "Genome-wide association study in alopecia areata implicates both innate and adaptive immunity", Nature, 466(7302), Jul. 1, 2010, pp. 113-117.

Kerns et al., "Genome Wide Association Study to Identify Single Nucleotide Polymorphisms (SNPs) Associated with the Development of Erectile Dysfunction in African-American Men Following Radiotherapy for Prostate Cancer", International Journal of Radiation Oncology Biology Physics, 78(5), Dec. 1, 2010, pp. 1292-1300.

Hao et al., "Tumor Suppressor LATS1 is a Negative Regulator of Oncogene YAP", Journal of Biological Chemistry, vol. 283, No. 9, Feb. 29, 2008, pp. 5496-5509.

Morin-Kensicki et al., "Defects in Yolk Sac Vasculogenesis, Chorioallantoic Fusion, and Embryonic Axis Elongation in Mice with Targeted Disruption of Yap65", Molecular and Cellular Biology, vol. 26, No. 1, Jan. 2006, pp. 77-87.

Barrett et al., "Genome-wide association study and meta-analysis find that over 40 loci affect risk of type 1 diabetes", Nature Genetics, 41(6), Jun. 2009, pp. 703-707.

Cooper et al., "Meta-analysis of genome-wide association study data identifies additional type 1 diabetes risk loci", Nature Genetics, 40(12), Dec. 2009, pp. 1399-1401.

Todd et al., "Robust associations of four new chromosome regions from genome-wide analyses of type 1 diabetes", Nature Genetics, 39(7), Jul. 2007, pp. 857-864.

Plagnol et al., "Genome-Wide Association Analysis of Autoantibody Positivity in Type 1 Diabetes Cases", PLoS Genetics, vol. 7, Issue 8, Aug. 2001, e1002216, 9 pages.

Wang et al., Genetically Dependent ERBB3 Expression Modulates Antigen Presenting Cell Function and Type 1 Diabetes Risk, PLoS One, vol. 5, Issue 7, Jul. 2010, e11789, 11 pages.

Weedon et al., "A common variant of *HMGA2* is associated with adult and childhood height in the general population", Nature Genetics, 39(10), Oct. 2007, pp. 1245-1250.

Kazmierczak et al., "Cloning and Molecular Characterization of Part of a New Gene Fused to *HMGIC* in Mesenchymal Tumors", American Journal of Pathology, vol. 152, No. 2, Feb. 1998, pp. 431-435.

Voight et al., "Twelve type 2 diabetes susceptibility loci identified through large-scale association analysis", Nature Genetics, 42(7), Jul. 2010, pp. 579-589.

Asher et al., "Disruption of the Architectural Factor HMGI-C: DNA-Binding AT Hook Motifs Fused in Lipomas to Distinct Transcriptional Regulatory Domains", Cell, vol. 82, Jul. 14, 1995, pp. 57-65.

O'Flaherty et al., "TOX defines a conserved subfamily of HMG-box proteins", BioMed Central, 4, 13, Apr. 2, 2003, 10 pages.

Moller et al., "Detection of an alteration in the insulin-receptor gene in a patient with insulin resistance, acanthosis nigricans, and the polycystic ovary syndrome (type A insulin resistance)", The New England Journal of Medicine, vol. 319, No. 23, Dec. 8, 1988, pp. 1526-1529.

Moller et al., "A Naturally Occurring Mutation of Insulin Receptor Alanine 1134 Impairs Tyrosine Kinase Function and is Associated with Dominantly Inherited Insulin Resistance", The Journal of Biological Chemistry, vol. 265, No. 25, Sep. 1990, pp. 14979-14985.

Taylor et al., "Mutations in Insulin-Receptor Gene in Insulin-Resistant Patients", Diabetes Care, vol. 13, No. 3, Mar. 1990, pp. 257-279.

Siegel et al., "A C/T single nucleotide polymorphism at the tyrosine kinase domain of the insulin receptor gene is associated with polycystic ovary syndrome", Fertility and Sterility, vol. 78, No. 6, Dec. 2002, pp. 1240-1243.

Accili et al., "Early neonatal death in mice homozygous for a null allele of the insulin receptor gene", Nature Genetics, vol. 12, Jan. 1996, pp. 106-109.

Huang et al., "*ZNF217* suppresses cell death associated with chemotherapy and telomere dysfunction", Human Molecular Genetics, vol. 14, No. 21, 2005, pp. 3219-3225.

Sun et al., "FSH Directly Regulates Bone Mass", Cell 125, Apr. 21, 2006, pp. 247-260.

International Search Report for copending Application No. PCT/CN2010/073387 mailed Feb. 24, 2011.

Jin et al., "Association between CYP19 gene SNP rs2414096 Polymorphism and polycystic ovary syndrome in Chinese women", BMC Medical Genetics, vol. 10, Article No. 139, Dec. 16, 2009, pp. 1471-2350.

* cited by examiner

SEQUENCE LISTING

```
<160> NUMBER OF SEQ ID NOS: 221

<210> SEQ ID NO 1
<211> LENGTH: 452
<212> TYPE: DNA
<213> ORGANISM: Homo sapiens
<220> FEATURE:
<221> NAME/KEY: misc_feature
<222> LOCATION: (400)..(400)
<223> OTHER INFORMATION: n is c or t

<400> SEQUENCE: 1
cgggttcaag tggttctgct gcctcagcct cccgagtagc tgggattaca ggcgccagcc      60
atcaagcctg gctaattttt gtatttttag tagagacagg gttttgccat gttggccagg     120
ctggtcttga actcctgacc tcaggtgatc cacccacctc ggcctcccaa agtgctggga     180
ttacaggcat gagccactgt gcccggccta gacttcactt tcaatgcata gggagacagc     240 ctgcttttttc tattttaaag aattgtagca ttggtcagag ctctgtaatc agatccaaca     300
aaagttttta tctgaaatgg tggataaact ggttctaaaa ataatcacag atgataattt     360
gtacactctt aacgtcaatg tcctgttatg caatttctcn gttaaaaaaa ttatatttgt     420
agagaaaagg aaaccatagg aacaacaaca ac                                   452

<210> SEQ ID NO 2
<211> LENGTH: 445
```

<212> TYPE: DNA
<213> ORGANISM: Homo sapiens
<220> FEATURE:
<221> NAME/KEY: misc_feature
<222> LOCATION: (222)..(222)
<223> OTHER INFORMATION: n is a or g

<400> SEQUENCE: 2

```
agataacaac tctatgctct ggcttcaaat aaaataaaat gaaaacaaac accaagatcc      60
tatcttagtt agttgaaaat aagatgggac agaaggggtg gggagatggt actctattat     120
tctacatttt taagtataga aatttggggg aaaaaaaatc agtcatgaaa atcagattta     180
gtattgtgga aaggaaaat tacactcaca tatgaaaagc tntatctgtg gacttgaaat      240
aaccagctga acaatagaca catggcaaga ttaacaaaca ctggagatga cattttcccc     300
aataaatgga ttttttttctt cattcaatat atggagcagc tctttgaaca acatagtaga   360
aatagtaagt gggctcagat ttgggtatct atatacaaaa ggatgaagaa agactttctt    420
tttaagaaca gcactgaagg gcctt                                          445
```

<210> SEQ ID NO 3
<211> LENGTH: 318
<212> TYPE: DNA
<213> ORGANISM: Homo sapiens
<220> FEATURE:
<221> NAME/KEY: misc_feature
<222> LOCATION: (275)..(275)
<223> OTHER INFORMATION: n is c or t

<400> SEQUENCE: 3

```
atctgccatt ccgatttcca attttttacca tggcccccag ccaagtaacc atcatatggc    60
actcttagac aaacaatagg ggacttgttt aaatcaaaat gcaaaatggt gatgaactgt    120
agaatatata tatttaaaca agtcatttcc cccactgtaa catggagagt ttagctgtgc    180
atgcagggcc agctggcaga agcttgtagg gcctggctgg ctaccaggac tgctcgttta    240
ccttgccctc cctggggag gtgtgacggc agagntgcat ttttatggta tgccccaaca    300
tccatcctgc ctttcttg                                                  318
```

<210> SEQ ID NO 4
<211> LENGTH: 328
<212> TYPE: DNA
<213> ORGANISM: Homo sapiens
<220> FEATURE:
<221> NAME/KEY: misc_feature
<222> LOCATION: (95)..(95)
<223> OTHER INFORMATION: n is a or c

<400> SEQUENCE: 4

```
tctgcctggg aagtgtaagt ctcttgtgtg aataaatttg gtggtgagaa aataaatgct     60
gttttcagct gttgtaaagc aaaatagaat cctanaccag aacttctgca gttagccaca    120
gaccccctag ggaagaactg ggattgccac acaaaagcct cagctttgtc tctataagca    180
tattttcctt aaacacttaa atccacaggc ccttcaggag cacaccactc agctcagtgg    240
ggtccagtaa gtaagacaga aaaaggagaa tagatgggag tatggatagg gggtgacagg    300
ggaggagaca ggaaagtgac tggagtat                                       328
```

<210> SEQ ID NO 5
<211> LENGTH: 401
<212> TYPE: DNA
<213> ORGANISM: Homo sapiens
<220> FEATURE:
<221> NAME/KEY: misc_feature

```
<222> LOCATION: (116)..(116)
<223> OTHER INFORMATION: n is c or t

<400> SEQUENCE: 5
tctgtcttgc tttcttagcc tccagctcca tctccaaaac atctcaagtc ttctcttcct      60
cagattaaac aagcccagct atttccttta aacttttaca accagaatta atgttncctt     120
gtgctctttt aaaaaatcaa atcaataaac acttaaatcc taacaatcac acaagaatta    180
aaaaacaaaa aaattttttt ggacaatgtt ctgaatcttt cacatgttct agacaggctc    240
agagaagtta actgacttgc ccaggctcac aaagggaatg aatgtatgag ctaggattca    300
aagtcaagtc tgtctcactg cagagcctgt gctagttgca aaaatgagtg ttccccatct    360
ctgatatttt taccaccata gaagtgaaca acaatagcac a                        401

<210> SEQ ID NO 6
<211> LENGTH: 560
<212> TYPE: DNA
<213> ORGANISM: Homo sapiens
<220> FEATURE:
<221> NAME/KEY: misc_feature
<222> LOCATION: (256)..(256)
<223> OTHER INFORMATION: n is a or c

<400> SEQUENCE: 6
cagcggtatg atttcgtagt ggttattaag gtaaaagatt cccctccccc caacttgatt      60
agattaaacc tgcttttctaa tatttgaac agccttttaa tttgcttatt ccatcatgaa     120
aaggtaattg tcaactcata ctagttttag tcaccctaaa ttctgacaaa cagaagccaa    180
atcagtggat tatttttcaa tatattccaa atgaatgcac aatggagact gctgtgcaaa    240
gttagaagat gaaacnaaac tgattacata cacctatacc ctgccactaa ttaaaaatat    300
actagtgtta caagtataca gtttcaatgg tggtggtatc tttgttcaga agcacggtac    360
attattatac agctgaagcc ctctagcatt taattaggct gctaattatg agaagaatca    420
cattgccttc aagtctttcc ctggattgtg accaagactt ggtatattaa tttcatggtg    480
attgtgtttt aagatgggaa acatgtcagt aaagaatact ggtcacatct ttcaaagtgt    540
ccaggtgatg agattttagc                                                560

<210> SEQ ID NO 7
<211> LENGTH: 560
<212> TYPE: DNA
<213> ORGANISM: Homo sapiens
<220> FEATURE:
<221> NAME/KEY: misc_feature
<222> LOCATION: (273)..(273)
<223> OTHER INFORMATION: n is c or t

<400> SEQUENCE: 7
cagcggtatg atttcgtagt ggttattaag gtaaaagatt cccctccccc caacttgatt      60
agattaaacc tgcttttctaa tatttgaac agccttttaa tttgcttatt ccatcatgaa     120
aaggtaattt tcaactcata ctagttttag tcaccctaaa ttctgacaaa cagaagccaa    180
atcagtggat tatttttcaa tatattccaa atgaatgcac aatggagact gctgtgcaaa    240
gttagaagat gaaacaaaac tgattacata canctatacc ctgccactaa ttaaaaatat    300
actagtgtta caagtataca gtttcaatgg tggtggtatc tttgttcaga agcacggtac    360
attactatac agctgaagcc ctctagcatt taattaggct gctaattatg agaagaatca    420
cattgccttc aagtctttcc ctggattgtg accaagactt ggtatattaa tttcatggtg    480
attgtgtttt aagatgggaa acatgtcagt aaagaatact ggtcacatct ttcaaagtgt    540
```
ccaggtgatg agattttagc          560

<210> SEQ ID NO 8
<211> LENGTH: 560
<212> TYPE: DNA
<213> ORGANISM: Homo sapiens
<220> FEATURE:
<221> NAME/KEY: misc_feature
<222> LOCATION: (365)..(365)
<223> OTHER INFORMATION: n is c or t

<400> SEQUENCE: 8
cagcggtatg atttcgtagt ggttattaag gtaaaagatt ccctcccccc caacttgatt    60
agattaaacc tgctttctaa tattttgaac agccttttaa tttgcttatt ccatcatgaa   120
aaggtaattt tcaactcata ctagttttag tcaccctaaa ttctgacaaa cagaagccaa   180
atcagtggat tattttcaa tatattccaa atgaatgcac aatggagact gctgtgcaaa    240
gttagaagat gaaacaaaac tgattacata catctatacc ctgccactaa ttaaaaatat   300
actagtgtta caagtataca gtttcaatgg tggtggtatc tttgttcaga agcacggtac   360
attantatac agctgaagcc ctctagcatt taattaggct gctaattatg agaagaatca   420
cattgccttc aagtctttcc ctggattgtg accaagactt ggtatattaa tttcatggtg   480
attgtgtttt aagatgggaa acatgtcagt aaagaatact ggtcacatct ttcaaagtgt   540
ccaggtgatg agattttagc                                              560

<210> SEQ ID NO 9
<211> LENGTH: 266
<212> TYPE: DNA
<213> ORGANISM: Homo sapiens
<220> FEATURE:
<221> NAME/KEY: misc_feature
<222> LOCATION: (92)..(92)
<223> OTHER INFORMATION: n is a or g

<400> SEQUENCE: 9
aagtagctgc ccaaacaatg tgatttcccc agcaatagga acaaccttc caatctctgc     60
ttctagatcc tccctatata aggcctaaaa cnccaccatt agagttttac tgctttattt   120
caaaatgtat gtatctgtaa tatacaaata ccccatggaa gataacactg ggggcattta   180
catgttttgc aagtttggcc tataagcaaa gaagaaaact gagcagcact gaacacctgt   240
gcctcaacaa tctggtccca agcctg                                       266

<210> SEQ ID NO 10
<211> LENGTH: 342
<212> TYPE: DNA
<213> ORGANISM: Homo sapiens
<220> FEATURE:
<221> NAME/KEY: misc_feature
<222> LOCATION: (196)..(196)
<223> OTHER INFORMATION: n is c or t

<400> SEQUENCE: 10
taaaccaagc tccaatttct catagaaacc ctgtcttcaa gatctgccac acatatgaaa    60
agttgcaatg ccagaagcac atgcttctga acaaaaagta taccagtgaa aactattgtg   120
cagtgaaaaa ggcatctggt gaaacgtgtt gaaaaaaagg tggggggga ggtatccaca    180
cacacccatt tcttanacac acatcccata tcattctcga tcatctcagg aatagggatc   240
aacagagtaa tgtacagagg tataaaaaga aagctagca aagcaagca aagccaccat     300
gtaggagtaa ggaactgcat aggaaacagt agtaaaggtg tg                     342

<210> SEQ ID NO 11
<211> LENGTH: 465
<212> TYPE: DNA
<213> ORGANISM: Homo sapiens
<220> FEATURE:
<221> NAME/KEY: misc_feature
<222> LOCATION: (307)..(307)
<223> OTHER INFORMATION: n is c or t

<400> SEQUENCE: 11
agactcagat gagatgccac atcactggac atgcgatctg gcttccctag cagctgccca    60
agggttgtgc caacacctgc ccaaattgtg gtaatgcccc aaggatgaac tttgaccagt   120
aaaagacaaa catattgggc tgttccaaaa ggtggtagtt tcacatggtc tggctagaag   180
atgcaccatg tacaagacaa ccagctcaga ttttctgcaa ggttaaggtt cccttggtaa   240
tatcattcat ctttccttgc ctcacttccc tttttctttc attcctgctg gtcttggtta   300
gtaccantca ataaaatgtt aggacccggg ctttacttcc agctctgttt aataagaaaa   360
tagggccaaa accctagaag gtaggtaaaa tgtaccttct ttgtattctt aaaataccca   420
aacatctcct ctacaatagc acacattctg gagttggaca ggtaa                   465

<210> SEQ ID NO 12
<211> LENGTH: 321
<212> TYPE: DNA
<213> ORGANISM: Homo sapiens
<220> FEATURE:
<221> NAME/KEY: misc_feature
<222> LOCATION: (168)..(168)
<223> OTHER INFORMATION: n is c or t

<400> SEQUENCE: 12
aggctgaagc aggagaatcg cttgaactca ggaagcagag actgcagcga gccaagatgg    60
cgccactgca ctctagcctg ggtgacacag caagactcca tctcaaaaaa aactaaaaaa   120
atttaaaaaa aaaaaagcaa aaatttttt ttggtgattt agctaccnaa gaagaaaaga   180
agctggaatt atagaggtga ataaggtaaa gagtacttga tctaatatct gtgggcttaa   240
tttatacttg cattttcttc ctagaaccat gggaaagtta aaaccagctt atagataatg   300
ctacagtcta aggtcgtctc c                                             321

<210> SEQ ID NO 13
<211> LENGTH: 553
<212> TYPE: DNA
<213> ORGANISM: Homo sapiens
<220> FEATURE:
<221> NAME/KEY: misc_feature
<222> LOCATION: (300)..(300)
<223> OTHER INFORMATION: n is a or g

<400> SEQUENCE: 13
tcatcgctca ttcagtcatc agtttcttct cacgcctatg tatgtgaggt taccatgtga    60
atggcaacat agaaaaatga ctggacctca ttacaacgga aactaatgtt ttacagaaaa   120
acagtcagga tcttattttt tatttaagca gtcactggaa gaattctttg gtttataaga   180
acctgtcttt ttgtgataat tgttttttt tttaacaaac atctcttatt ttacattaat   240
tcccaatttt aacacggctg tcgcacacaa attaaataca taagatttgg gtgctatgtn   300
aaaagtgtca aggcaaaata atgttcatag gaagctttca cgtcttagtt acagtaaaag   360
caaaatacac ttcccttaat ttgtttttta aacactaccc aacaaaccca aaaaactaaa   420
tgttttaact tgtccttgga aagagaagtt gggaaatcaa aggcctctag cacatgttta   480

```
cttcttagca agatggtgaa catcagtgaa gtaatcatta atcatagctg gattcctcag    540
caaagatgtt ggc                                                       553
```

<210> SEQ ID NO 14
<211> LENGTH: 460
<212> TYPE: DNA
<213> ORGANISM: Homo sapiens
<220> FEATURE:
<221> NAME/KEY: misc_feature
<222> LOCATION: (109)..(109)
<223> OTHER INFORMATION: n is c or t

<400> SEQUENCE: 14

```
attaatatgg ccaactcaaa tgaactttac actagagttt tttaatcaaa aagagatctt     60
tcagggttat ccaacagggt ggctcatttc taggcagaac tgagtgtcnt tccctaaact    120
gcctgtatcc attacagcat tcactcttag tccttcctcc taaacatcct ctcactaggg    180
tatcaaaccc caggctgatg tggcatgtgc taattggaca gcagatggct ttcaaattaa    240
aaaagaaaaa aaagaacagc ttttctgaga tgtaattcat atgccacaaa attcatacat    300
ttgaagtata caatagtttt tattagtcac atatgtacaa ccatcaccat aattaatttt    360
agaacatttt cactgccctc ctgccaccaa acgaaaaaaa aaaagaaaa  cttacccgtt    420 agcagtcact gctctccttg cacctctacc cttctccagc                          460
```

<210> SEQ ID NO 15
<211> LENGTH: 542
<212> TYPE: DNA
<213> ORGANISM: Homo sapiens
<220> FEATURE:
<221> NAME/KEY: misc_feature
<222> LOCATION: (189)..(189)
<223> OTHER INFORMATION: n is a or g

<400> SEQUENCE: 15

```
aaaggacatc gacaggcatt gcactgaagg ggaaaagtaa atggcttgta acatgggaa      60 aaataattg tattagtaat cagaaaaatg taagatgaaa ccacaatgag atatcgtttt    120
atattatata aatttttaaa atctgacaat agcaaattat ggtgatgatg tgatgcaata    180
caagtctcng aatttgttgg tgagagtgta atttaaaagc ctacttggca tcatctcata    240
aagttcaaga tgcacatact ttgtgaccag gttattccat ttgtttacca taaactctta    300
gacatgtgca ttagaagata ttaatataca ggctaagtac tccttatctg aaatgcttgg    360
gaccataagc gtttcagatt ttatattttt tcagattttg gaatatctgc atcatacttt    420
gaacacccca aatgtgaaaa tccaaaatcc aaaatgctcc aatgtgcatt tcctttgagt    480
gtcatgttgg tactcaaaaa gctttggatt ttggaccatt tcaggtgttg gattacggat    540
gc                                                                   542
```

<210> SEQ ID NO 16
<211> LENGTH: 426
<212> TYPE: DNA
<213> ORGANISM: Homo sapiens
<220> FEATURE:
<221> NAME/KEY: misc_feature
<222> LOCATION: (215)..(215)
<223> OTHER INFORMATION: n is c or t

<400> SEQUENCE: 16

```
cctattcacc tcaattgcag tcctcttccc actgtctcaa tagggtctcc tttgaaatcc     60
agctatgaag caattcaagt aggcaagcat catcctccat ggtactgtca cctctctatc    120
```

```
tccagatctc tggccatatt cccaccagaa ctacccatgg cctcctcttt ttctcccatt    180
actagttctc tttttcatgg ctgtttctac catcntggaa ataataattt ttaactctct    240
ttctatatct gatctccctt ttcctattaa aaaaaaatcc ttatctgtcc ttatttctag    300
tacaattcta aaatgaagac tgactagcat aaaattaagt acatgaatcc ccaataaata    360
tttgttgaaa atcactagat ctgaataatc tcagaccgta ggttttggaa ctggctattt    420
gggaag                                                              426
```

<210> SEQ ID NO 17
<211> LENGTH: 521
<212> TYPE: DNA
<213> ORGANISM: Homo sapiens
<220> FEATURE:
<221> NAME/KEY: misc_feature
<222> LOCATION: (241)..(241)
<223> OTHER INFORMATION: n is a or t

<400> SEQUENCE: 17

```
ggttttggaa ctggctattt gggaagagta aaaggcaggg gtatgacagt taattaaaac    60 ataaccctg acagaaaaag gaactccacc tatatagaaa caataaagat ggtctgtctc    120
tagtcacagt ataatttatg tagggaaaaa agcacacttt tggtggagaa agaggtcatt    180
ctcatttcaa aagagcttta ttaataaata tttgtatatg tacttattca acataaatcc    240
nctgtttaga aaaagtatt atagctgact aaaatgttca tttgcataat gagaacccat    300
ggtgctctta tatgctgata aactttttaaa taaaaaacca caaatatat gtttaaccat    360 tagatattct aaccaaatga atactgagac taagctattc gttttgataa gagcaaacat    420
caatacaaac ccattaatgt gttcctttcc accacagcag caggcctatc tccattatca    480
catgcaactt gctgagttaa gtaggcagac aaggatgacg g                        521
```

<210> SEQ ID NO 18
<211> LENGTH: 297
<212> TYPE: DNA
<213> ORGANISM: Homo sapiens
<220> FEATURE:
<221> NAME/KEY: misc_feature
<222> LOCATION: (199)..(199)
<223> OTHER INFORMATION: n is c or g

<400> SEQUENCE: 18

```
ccatgagcca ttattgtaaa ctgattagta aagaaatttt cattttataa caatttagac    60
tttaaaaata ttaaatacac agaatgacca caaatttcaa ttattaaatt tacaagaaca    120
aaaaactaca agtaaagcca aaacagatct caaatttgta tatgattctt tttaccttgt    180
aaaaaataat ccagaaagna gttcaagatc agcctaggca atatagtgaa accccatctc    240
tataaaaaat ttaaaaattt agctgggtgt ggtgacacac acctacagtc ccagcta      297
```

<210> SEQ ID NO 19
<211> LENGTH: 382
<212> TYPE: DNA
<213> ORGANISM: Homo sapiens
<220> FEATURE:
<221> NAME/KEY: misc_feature
<222> LOCATION: (157)..(157)
<223> OTHER INFORMATION: n is c or t

<400> SEQUENCE: 19

```
ttagaaatgc tggtggttgt acaactctgt gaataaaacta taaaactgaa ttgtacactt    60
caaatttatg aattgcataa tatagctcaa atatgtaaaa aattattttta gttttcctcc   120
```

```
tttattcata tgttcagtat tatcaagctg tatatangtt tcgacatttc atatacatga    180
tcactttcag ccattatggc aaaaacacca caaaaataca aaatacagcc ccatgaagtc    240
agaagacctt ctaagattgc tgtttcaggt tcttattagc aatatggtct caggtaagca    300 tttactttc taagcctccc tttgcccatt caacaaatta gatttcttat cctatatagt    360
agccatttga ggatcacatt ag                                             382

<210> SEQ ID NO 20
<211> LENGTH: 446
<212> TYPE: DNA
<213> ORGANISM: Homo sapiens
<220> FEATURE:
<221> NAME/KEY: misc_feature
<222> LOCATION: (415)..(415)
<223> OTHER INFORMATION: n is c or t

<400> SEQUENCE: 20
aacccaggca aaagagaaa tagaaatact aattggacaa aatatagcta agactttcat     60
taccagggtt aaaaacacaa acaatgaggc caggcgcggt ggctcacacc tgagccactt    120
tgggaggcca aggcgggcag atcacctgag gtcaggagtt ccagaccagc ctggccaaca    180
tggtgaaagc ccgtctatat taaaaataca aaaaaaaaat tagccaggcg tggtggtgca    240
tgcctgtaat cccagctact cgggaggctg aggcaagaaa atcgcttgaa ctgggaggc    300 agaggttgca gtgagccaag atcacgccac tgcactccag tgtgggcgac aaagagagac    360
tccatctcag acaaaaaaaa aaaccaaaaa acacaaacaa tgagatgcta ttgtnttcca    420
atcagcctag caaaaccaga gtcagt                                         446

<210> SEQ ID NO 21
<211> LENGTH: 434
<212> TYPE: DNA
<213> ORGANISM: Homo sapiens
<220> FEATURE:
<221> NAME/KEY: misc_feature
<222> LOCATION: (67)..(67)
<223> OTHER INFORMATION: n is c or t

<400> SEQUENCE: 21
ccaagtgtca cctctgccat ctggtggtca aatgacaata taactgcaac aactcagtgt     60
ggatacnatc atcatgtgaa agtcacccat gaccccaggg ttgggtgaac tatttgaggc    120
tgggctctga cttttacggc ctgagatgag aaaataaaat gttgaataca caaataaagg    180
tcagaggttt tcccctatat ctctgctcag ggtgaggaac tgtgtagttt acaatggaag    240
agcccattca tccatttatt caacaaatat ttattaagca ctgtcttagg ttggcttcct    300
aggaaacaga ttctaggcag agatttgctt aaggagggtt actgggagc attcttgagg    360 atcacccttg taagggttg agggaaacag aactcgtcag aaagagttga actggaatga    420
atttgcaaca gtgg                                                      434

<210> SEQ ID NO 22
<211> LENGTH: 341
<212> TYPE: DNA
<213> ORGANISM: Homo sapiens
<220> FEATURE:
<221> NAME/KEY: misc_feature
<222> LOCATION: (265)..(265)
<223> OTHER INFORMATION: n is a or g

<400> SEQUENCE: 22
gtggttctta ctctagcaca atgattcaaa accaaggggt ggggaggaat ttcccctgc     60
```

```
cccctccggg ggtcatttgc caaatgtcta gagatacttt tggttgtcac aatttgggaa      120
ggcagcgctc ctggccaggg atgctggaaa acattctaca aggttcaaaa cagctcccat      180
aacaaagaat tatctggccc caattgtcaa ttgtcaatat tgctaagatt tagaaacctg      240
ctctggcaga agaggcacat gttgnacaaa tggctgcatt atggtgagat atgtacaaaa      300
atatatgtaa gcccaggata ttgaagtgag tatgtggatg g                          341
```

<210> SEQ ID NO 23
<211> LENGTH: 842
<212> TYPE: DNA
<213> ORGANISM: Homo sapiens
<220> FEATURE:
<221> NAME/KEY: misc_feature
<222> LOCATION: (774)..(774)
<223> OTHER INFORMATION: n is a or g

<400> SEQUENCE: 23

```
caaaaccagg ctgatgacaa tcatctgaaa acctaatttt tcaagcacac gtgaaccctt       60
aaaattgttc aagaatcctc taatctgcag tgccacaggc ctcctgttgc ccacccctc       120 cagtctgctc caaacatttt tcctcttctg tccctctctt cagaagatac tcttctctcc      180
aaacgcacca agagaaaag ctttcacatg agctcttcca ctcctatact tctcattcct      240
ttcttctcaa accacaacct tagcaccaag gttatatgtg gttcctccct aagggaaaag      300
cacacctcat cttcctgaga taaccacatt tagcttcaat gaacattttt acagaattta      360
aaactgagac gtttccagtc caaacatcac acatttctag atgattcatt tttcaaatgt      420
tccatcaatg gcatctaccc acatatttc ccatgcttat taagacccac cagtatatgc      480
ctggccctct gctaggtaca tgggggaata aggcccatgt ctcagtatct ggggagctca      540
cagtctaaag aggaaagcag acacactggc agataatgtc agcagcactg ggtcagtgct      600
ttgatagagg ttcacaaagg gaacacagaa gagattctag aaagtcttcc aagaggaagt      660
gacacctcac tgatcagccc tctccctcct aactcgaggt gagaaggagg aaagacccca      720
gagcccaact gcactgcctt ctgtaagaca catcttctcc cctattatac tcanccagca      780
agcattccca cctttaagca acagaaat cactcatgtg tgctggtcta tgattctcaa       840
ac                                                                    842
```

<210> SEQ ID NO 24
<211> LENGTH: 472
<212> TYPE: DNA
<213> ORGANISM: Homo sapiens
<220> FEATURE:
<221> NAME/KEY: misc_feature
<222> LOCATION: (55)..(55)
<223> OTHER INFORMATION: n is c or t

<400> SEQUENCE: 24

```
ctccagggac tgcctctttc tctagcaaca cctctgcaaa cgatgagacc agatnaatgt       60
ttggagaagt aaataaggc aataatacct agatctcatg ggctttgaga aaagtgaagt      120
gtatgctggc gagtcttctt taaaaagcaa ggagctagtg gcagcagtgt ggtgcatgga      180
atgctcatgc acagcttgca gaagcagaaa atggtgaaac cactgaagga aacaatttgg      240
cattatctca ataagttga ttgagcttaa tagaataaaa ttgcccaatt tggcatttat      300
cccaatgaag tcaacgatat acatgtccta tgacacaact attcaactcc ttaggtacat      360
acagtacaca gaagttaagt ctatgtgcac cagtatagct cttcaagaat gttcataaaa      420
gtcacacgct agaaacagtc caaatggcca cctacagtta catgcataaa ca              472
```

<210> SEQ ID NO 25
<211> LENGTH: 429
<212> TYPE: DNA
<213> ORGANISM: Homo sapiens
<220> FEATURE:
<221> NAME/KEY: misc_feature
<222> LOCATION: (82)..(82)
<223> OTHER INFORMATION: n is a or g

<400> SEQUENCE: 25

```
gagcagccac tcaagaaaca gggcactggg ttgtttcagg cagagaaaag aactaggcag        60
agattctggg gactggaaag anctagttat gatcaaggaa ccaaaaggac aggagtcctg       120
ctaatgcaca ggagataaag gggaaagtgg catcacatta agctgctaga taaagcaagc       180
tccagatcac acagagagtc ccacaggtca tggtaaagaa ttcagatttt tttttttttt       240
ttggcggtgg ggggaggcaa tagaatgcca ctgaatgatt tgatcaaga gaaaaacaca        300
gtctggttta tagcttcaaa tatttcaact gacttataca gagagcagtt tggaagaagg       360
tgtaagtagg agtagagaaa ataatctgga agtgattgca gtagtccagg tgagactgga       420
tggtggctt                                                               429
```

<210> SEQ ID NO 26
<211> LENGTH: 648
<212> TYPE: DNA
<213> ORGANISM: Homo sapiens
<220> FEATURE:
<221> NAME/KEY: misc_feature
<222> LOCATION: (398)..(398)
<223> OTHER INFORMATION: n is c or t

<400> SEQUENCE: 26

```
aaacaagata gggctaggct gatttaaatt ataagttgaa gtctaggaaa acaaagtct         60
atataataca aaacgttgga atcaagtaat attacttgtt taagccaaat atattcatat       120
ttaaataaca attaaatagc aagagattaa ataccaacca ttcttaatca cagtttaagt       180
ctgataacaa aatcaaaact ttaatgccat acaaaataca tctcacaaac taaccaatgc       240
aaagctctaa gctttaaact ttttgacagt gtcaataaaa accccaggaa gggagaatat       300
tgcaactctc cttggaacac aggtatctta aatcatggtt aaacagacag aatgttaaga       360
atggtatggt ttttatttc tatagcaggt ttattganac tttttttcta gtaaagtttg        420
aaaatctgac actacctgtc cacatagaag gggaaacaaa acttggtcaa agtctgtaga       480
acttcctgtg gagagaaaga gagataattt atacatctaa tgggaccagt aaatctaaca       540
ttaaccacag cacacaatct agcaacttta ccctaaagaa agaggagaca gatgaagaaa       600
tatgggcttt atcaattaca tgggaggagt accaggcagt caatcatg                    648
```

<210> SEQ ID NO 27
<211> LENGTH: 273
<212> TYPE: DNA
<213> ORGANISM: Homo sapiens
<220> FEATURE:
<221> NAME/KEY: misc_feature
<222> LOCATION: (213)..(213)
<223> OTHER INFORMATION: n is a or t

<400> SEQUENCE: 27

```
agaggctatt ctcagtgagc ttctcgcctc tcccaagttg acaccccaga atcctgtcct        60
gtgtctataa ttcctatcat caaattgacc attatctcta gaatgagtta agaatgatgg       120
gggttacact cattaccagt gttccccaga gtatctggca cagaggaaac atccagtgaa       180
```

```
tgatggtgct gaaaaaaatg attggatgat agntcggatt aagaagggaa gaaatagcat    240
tgactgagca cttactattg ccatgcactg tgc                                 273
```

```
<210> SEQ ID NO 28
<211> LENGTH: 255
<212> TYPE: DNA
<213> ORGANISM: Homo sapiens
<220> FEATURE:
<221> NAME/KEY: misc_feature
<222> LOCATION: (104)..(104)
<223> OTHER INFORMATION: n is g or t

<400> SEQUENCE: 28
agcatacctc aagcatgaac agatgaaaac tccatattta agcaattaca tgcaactcag    60
aaatgccaat ttccatcaca attagcctga gttatgcaac atantttttgt tccttttttag   120 tatatagttg gtatatgttt ttataatttg tttaactgcc tatagtgaaa ttttgaaatc    180
acataggcaa tataaaacct taagagaaag ggcaccttt aattttttccc aatgtgccat    240 gtttctacat tgctt                                                     255
```

```
<210> SEQ ID NO 29
<211> LENGTH: 304
<212> TYPE: DNA
<213> ORGANISM: Homo sapiens
<220> FEATURE:
<221> NAME/KEY: misc_feature
<222> LOCATION: (50)..(50)
<223> OTHER INFORMATION: n is a or g

<400> SEQUENCE: 29
gctccctcct tcaacatcca ccaatgaaag atctcaatcc cagggcactn acaagatgcc    60
ttcgtctcac agcatcaaag ccaccatgtg caaatggcag cagcacatat gtcttgtagc    120
cgtgataaga aggaatccaa aataacaagc tagctccaga acactgagca acggaaaggc    180
aatgaagttt accaaggagg cttcccaacc taacacctaa acactggatt gcattcaagt    240
caatctaccc agtgtatcat tctgcttact ccccaaggca tgtctgtctt cttgttggca    300
ttgc                                                                 304
```

```
<210> SEQ ID NO 30
<211> LENGTH: 481
<212> TYPE: DNA
<213> ORGANISM: Homo sapiens
<220> FEATURE:
<221> NAME/KEY: misc_feature
<222> LOCATION: (326)..(326)
<223> OTHER INFORMATION: n is c or t

<400> SEQUENCE: 30
ctgtggctca ccttggagat tatccagtct atagttgtag aaagtgaggt ccaggaagga    60
agagatttgc ttaaagatat ttagggaata tacaggatga gaacaaaatt taagttccct    120
agaccacggg tcagtaaaca ttttttttttt ttttttacag ggctagatag taaatacttt    180
tttgcccttg ctgtggtatt tggtctctat cacaactgcc caattgacat tgtagcccaa    240
atgtaaccaa aggtaacaca tgaatgaatt agcctgtgtt ccaataaaac tttattcata    300
aaaacaggtg tcaggctgga tttganccat tggctgtagt tcagtgacac tgtcctagat    360
cgtggagttg ttttctctct gctaatctgg ctttgagaga tgagaacttc aatccagtct    420
cttttaaaat acacatatgt ttgttggccc cattaatgtc taacgtagga acagaaagcc    480
a                                                                    481
```

<210> SEQ ID NO 31
<211> LENGTH: 300
<212> TYPE: DNA
<213> ORGANISM: Homo sapiens
<220> FEATURE:
<221> NAME/KEY: misc_feature
<222> LOCATION: (112)..(112)
<223> OTHER INFORMATION: n is a or g

<400> SEQUENCE: 31

| | | | | | |
|---|---|---|---|---|---|
| tgttatttga | ttgatggtcc | tagaggattt | tattttacta | tttctagatt | attctgagga | 60 |
| aggcccaaga | taggtcttgg | gtctttcaat | tctggaattg | gaagggaatc | cnaggagatc | 120 |
| tataccaggc | aatgcattat | ttccttgaga | ttatcccctt | gacatcctta | cctgaaagga | 180 |
| agaagacaga | ctctctcagc | cttagggaac | ttccttcctt | tctcagcatc | agacatttaa | 240 |
| agaagtgaaa | aaaaaaaaga | aagcacactg | aagaaatggt | gcaatgatag | tagcctaaag | 300 |

<210> SEQ ID NO 32
<211> LENGTH: 186
<212> TYPE: DNA
<213> ORGANISM: Homo sapiens
<220> FEATURE:
<221> NAME/KEY: misc_feature
<222> LOCATION: (157)..(157)
<223> OTHER INFORMATION: n is c or t

<400> SEQUENCE: 32

| | | | | | |
|---|---|---|---|---|---|
| aatcctgtcc | gtttccaaca | ctgcattggt | ggtcaggaca | atgtgctttc | atttgcacaa | 60 |
| gcatgttcag | gaggagtcct | cctgcaaggt | agatgcccgt | gttgctggga | ctcagtccct | 120 |
| tgtgatgggg | cccaccaaag | acagttttgc | ttgggtnctc | tcaaagctat | gctgttgggt | 180 |
| ttgtgc | | | | | | 186 |

<210> SEQ ID NO 33
<211> LENGTH: 560
<212> TYPE: DNA
<213> ORGANISM: Homo sapiens
<220> FEATURE:
<221> NAME/KEY: misc_feature
<222> LOCATION: (195)..(195)
<223> OTHER INFORMATION: n is c or t

<400> SEQUENCE: 33

| | | | | | |
|---|---|---|---|---|---|
| atcacaagtt | tgccttctta | aatatgtaac | ataaactagt | gtgacaatct | tcttcaagaa | 60 |
| cattggtaaa | tgcttaggct | tataaaacca | catgaataaa | aaggattttt | taaccttttc | 120 |
| tgtaggcgta | attatatagg | tatcttttct | aaagcattaa | gactaagttt | ttataaatca | 180 |
| gcttatggac | gtctnaggaa | tgttcacaca | cccaacacag | cacacctggt | ccctggctct | 240 |
| attttctttg | tgtactttag | aaagtagcta | ggaaatttca | ctgcccagca | cctgacagat | 300 |
| gccctggctt | ctgcttctcc | tttgggctag | cttttcatc | aattttctat | tgctttcacc | 360 |
| cttgggttcc | atacagacct | ctccattgtc | cacaaagctt | tgtggttta | attttaccaa | 420 |
| caccttttt | gtagtactct | actaacctca | ggtcatactg | atactaatcc | tggccactga | 480 |
| accaagagag | taaatatgga | ttttacaatg | gtgggtcagt | tgttcgttac | tgaacagaga | 540 |
| actctgcgat | cttctggcac | | | | | 560 |

<210> SEQ ID NO 34
<211> LENGTH: 323
<212> TYPE: DNA
<213> ORGANISM: Homo sapiens

```
<220> FEATURE:
<221> NAME/KEY: misc_feature
<222> LOCATION: (130)..(130)
<223> OTHER INFORMATION: n is c or t

<400> SEQUENCE: 34
cctcttcacc cacagcaaca tgcacgatga aatctaagga cccaggcaca gcatcatggg      60
tgctttcagt gctttgaaag gaactatttg gttgggaaag ccagtttcgg gaggataagg     120
catattcatn gcacacatca ggcatggctg cttcctggag agtagtgaaa caaagtgaaa     180
tctgaacatc atggcattga gtgcgtcaac acgaaatctg cacttatag gaaagatgga      240 ctacaacaag caaaaataat acaaatcact atcagaccac agagaggctc aggtgcaagg     300
aatgaggacc acttccactg tct                                             323

<210> SEQ ID NO 35
<211> LENGTH: 427
<212> TYPE: DNA
<213> ORGANISM: Homo sapiens
<220> FEATURE:
<221> NAME/KEY: misc_feature
<222> LOCATION: (392)..(392)
<223> OTHER INFORMATION: n is c or t

<400> SEQUENCE: 35
ttttctgttg tatgggatga atggatctaa ttttatcttc ttccatatgc taactgtgta      60
tctttcccct catctttatc atagaataaa ttctgacatt ttgttatttc cagattttt      120 attttattaa tctaactatt cttatactag tacggcagta ctgcctttat gtttatacta     180
tgtaaacgtg taagttatat acatgtatat atgtgtatat aaacattatt tagtatgtac     240
aatatgtaca aaagtacaac tttagtagta tgttttaata gctggtaggg caagacatgt     300 ttttgaaac  taacttttttt attataagtt taaatttagt tgcattgagg tttaaaaaac    360
atagtctaca taatattgat tctagacaat tngtgactct gtgacttgac agtggtcaat     420
ccttgta                                                               427

<210> SEQ ID NO 36
<211> LENGTH: 284
<212> TYPE: DNA
<213> ORGANISM: Homo sapiens
<220> FEATURE:
<221> NAME/KEY: misc_feature
<222> LOCATION: (113)..(113)
<223> OTHER INFORMATION: n is a or g

<400> SEQUENCE: 36
tgcagtaggc tgtcttcaaa tcagcaatat gttttattgt cttttatctt ggttgtaacc      60
aagagcttaa agaccattag cctatacata tgtaatgtgc atttatcccc ccngtgcatt     120
accttacaat tgtccgtatt cctctctcaa ttcatcaaaa aatatttgtt aagcacctag     180
tgggtaccca gcaccatgct aggtgctgtg gggaacacag aagaaatgga agacagagtc     240
tctgcccgct gtgctcgtat ctagaagtgg ctgcatcaca aggt                      284

<210> SEQ ID NO 37
<211> LENGTH: 488
<212> TYPE: DNA
<213> ORGANISM: Homo sapiens
<220> FEATURE:
<221> NAME/KEY: misc_feature
<222> LOCATION: (305)..(305)
<223> OTHER INFORMATION: n is c or t

<400> SEQUENCE: 37
```

```
cgagacaggc aggttgctaa gaagcctggg agaagaggct ggctcttttt gctgtcactc    60
tcgccaacag tccggagtcc attataccc tggtgtgcaa agaatgggac ccttgtgcac   120
cagggctgta tgtccggagc tcgggcagtg tggaaggtga caaggaatcc aaaagttggg   180
ctgacaggtg ggagattttg agacaccct gccgcccctc cctggaggag gcctcgggat   240
ccagtccggt ttccccggc tgtgatctcc actttaaacc cagggtagac ctacctctat   300
ctacnctgtt gcaactacaa ctaccctgtt tatcttttag ggaaagcaaa gtcaatcgct   360
tagttctcgt attccaggaa tgataacaga aatgcctaaa atagtggttc caagaatttg   420
agattccttg ggctagtcga atttctcccc aaacaaaaat gaaacaacaa cactgaatag   480
ccgtcttt                                                            488
```

<210> SEQ ID NO 38
<211> LENGTH: 418
<212> TYPE: DNA
<213> ORGANISM: Homo sapiens
<220> FEATURE:
<221> NAME/KEY: misc_feature
<222> LOCATION: (221)..(221)
<223> OTHER INFORMATION: n is c or t

<400> SEQUENCE: 38

```
caggctgagg caggagaatc aggcagggag gttgcagtga gccgagatgg cagcagtaca    60
gtccagcttc ggctccgcat gagagggaga ccgtggaaag agagggagac cgtggggaga   120
gggagagggg gaggggagg gggagggga gggaccaatc aacagtctta taagtagata   180
caacagtgta taaacaagga aaccaaggaa gattttctc nttcagaact cggaccctga   240
ataccaggtt gagctggagc tgagtgagta ataaaatgaa aggccctta atgtggggga   300 gggtaggtag gagtggagac ccttaagtag tatcagcact gttgtctgat gggagtgtga   360
atctgaacac atgaagctcc agtctcagta gaacagtaag aaatcctaag taaggcca     418
```

<210> SEQ ID NO 39
<211> LENGTH: 392
<212> TYPE: DNA
<213> ORGANISM: Homo sapiens
<220> FEATURE:
<221> NAME/KEY: misc_feature
<222> LOCATION: (210)..(210)
<223> OTHER INFORMATION: n is c or t

<400> SEQUENCE: 39

```
gagccactac gcctgtctga tttttttaat tttttgtaga tttttgcta tgttactcag    60 gctggtcttg gactcctggg ctcaagcgat cctcccacct tggcttccca aagtgccagg   120
attataggca tgagccacca tgctcggcct gctccttttc ttgaaacacc tcctctgtgg   180
tttagattcc aggagactgg aatggtctgn cctggtgggc tgctgagtca gggacctgag   240
gtgtttgttc actgggagg cgggttcaga tcaggaatgt aaggatgatg gaaagaaggg   300
agtcactctg gtttggtggg actggggagc aatcttgatc acggccactt acagcttctg   360
ccattgtcct tcaccactat ctcagcatct cg                                 392
```

<210> SEQ ID NO 40
<211> LENGTH: 360
<212> TYPE: DNA
<213> ORGANISM: Homo sapiens
<220> FEATURE:
<221> NAME/KEY: misc_feature
<222> LOCATION: (284)..(284)
<223> OTHER INFORMATION: n is a or c

```
<400> SEQUENCE: 40
acttcttacc atctcctacc caccttrggg acatagtccc ccacaaggct cacacatctt    60
gagcccattt ttatctactt ccatcttgtc aggaggacag gccctgacac aggatgtttg   120
atccaccaca aagttatcta gggaagagga ggaggacacc attagagatg agggaggaac   180
atcaccagct accaatggaa cccttgctct gggcctaggc tccctccagc tctgcactgg   240
atttgtcccc atctgccacc ctagatccct taagtgctgc cctntagatt caaaagtctc   300
ttcactattt gttgctacaa ggagcagaag taagggtgat agctgaagtc atgggaggac   360

<210> SEQ ID NO 41
<211> LENGTH: 180
<212> TYPE: DNA
<213> ORGANISM: Homo sapiens
<220> FEATURE:
<221> NAME/KEY: misc_feature
<222> LOCATION: (112)..(112)
<223> OTHER INFORMATION: n is g or t

<400> SEQUENCE: 41
ggtttgaaat tgaagtgatg gctaatttag tagtcattca cttggtcttg caacattctg    60
catgcattgt ccagtttcac actgttaatt ttcaaatcaa cagctttgtt tncaaatgtc   120
ccaaggccaa ttactgaatc caaatataaa ctttgtaagt caagaaactc caagcagcaa   180

<210> SEQ ID NO 42
<211> LENGTH: 202
<212> TYPE: DNA
<213> ORGANISM: Homo sapiens
<220> FEATURE:
<221> NAME/KEY: misc_feature
<222> LOCATION: (102)..(102)
<223> OTHER INFORMATION: n is g or t

<400> SEQUENCE: 42
agtccctact cactgatcct ctgcctactt cataaataga gaaaaattct tcattataca    60
aaatgaggaa tttaagttat tttccctatt aaagaacatc cnctcatagt ttttcaagtt   120
attatgtgac aatttgatgt ggattaatgt acggctggct cttatcacct agatgaaaag   180
agtatcagtg ctaagatggg ca                                           202

<210> SEQ ID NO 43
<211> LENGTH: 848
<212> TYPE: DNA
<213> ORGANISM: Homo sapiens
<220> FEATURE:
<221> NAME/KEY: misc_feature
<222> LOCATION: (257)..(257)
<223> OTHER INFORMATION: n is c or t

<400> SEQUENCE: 43
acagttggac ggtggtagac attgacccac ccctgaggtc caacgacccc aaatcacaga    60
accacccagg gtggctgatg cggggtctca agccctggac ccagtatgcc atctttgtga   120
agaccctggt caccttttcg gatgaacgcc ggacctatgg ggccaagagt gacatcattt   180
atgtccagac agatgccacc agtgagtgtg tcttgggaat gtgaattcgt atgtgaatca   240
gacctcttgc tttttaanagg ctgatgcagt gaggttgtat aaaatgctcc ttgatatggt   300
tattggcttt tttttttttt ttagacaggg tcttactttg tcacccaggc tagagtgcaa   360
tgcagtgggg tgatcatggc tcactgcagc ctcaaactcc tgggctcaag caatccttct   420
gcctcagcct cctaagtaga aggaactacc agagtatacc accatgtgtg ctttttttt    480
```

```
tttttttttct ttgagatgaa gtctcactct gtcacccgga ctggagtgca atggcatgat    540
ctcggctcac tgcaacctcc gcctcccagg ttcaagtaat tctcccacct cagcctcctg    600
agtagctggg actacaggca tgcaccacta tacccagcta attttttgtat ttcttgtaga    660 gacagaacgt tgctgtgtta cccaggctgg tcttgaaccc ctggcctcaa gtgatcctcc    720
tgcctcggcc tcccaaagtc ctgggattag aagtgtgagc caccttgccc agtcagttat    780
tggcttttaa aggagctggg tattgaggct tatagtttca dacgaggcag tagcaacaag    840
ccacttga                                                            848
```

```
<210> SEQ ID NO 44
<211> LENGTH: 314
<212> TYPE: DNA
<213> ORGANISM: Homo sapiens
<220> FEATURE:
<221> NAME/KEY: misc_feature
<222> LOCATION: (175)..(175)
<223> OTHER INFORMATION: n is a or g

<400> SEQUENCE: 44
tgtgcctaaa taagatggtt ctctgaacat ttgctgactg tttacaagag aaaaataatt     60
attcctggct tgtaagcctg tcaggccatc acagaagaag gtacaaacta tttccacatt    120 ttttaaccccc ctcagtttct ctatgattat tcgttgacta ttttagctgg tgacncaatg    180
aaaaaacaga gtctaagcaa tttctctagg aatcaagatt tatctgcatt tttttttttt    240 ttttttttt ggccagagtg gcgtgatctt ggctcactgc aacctccgcc tcccaggttc    300
aagcgattct cgtg                                                     314
```

```
<210> SEQ ID NO 45
<211> LENGTH: 527
<212> TYPE: DNA
<213> ORGANISM: Homo sapiens
<220> FEATURE:
<221> NAME/KEY: misc_feature
<222> LOCATION: (41)..(41)
<223> OTHER INFORMATION: n is c or t

<400> SEQUENCE: 45
gtagtgctag aggcctgcca gttttagggg ccatttggct nctgagaaga actgttaata     60
aaagtattaa taaggaagag acacacaaa acacgctcaa tgggaaaagc caggcgtgca    120
gctgacctgg ccctggccta ggacaatgtt tacaaggatt gaccactgtc aagtcacaga    180
gtcacaaatt gtctagaatc aatattatgt agactatgtt ttttaaacct caatgcaact    240
aaatttaaac ttataataaa aaagttagtt tcaaaaaaca tgtcttgccc taccagctat    300
taaaacatac tactaaagtt gtacttttgt acatattgta catactaaat aatgtttata    360
tacacatata tacatgtata taacttacac gtttacatag tataaacata aaggcagtac    420
tgccgtacta gtataagaat agttagatta ataaaataaa aaatctggaa ataacaaaat    480
gtcagaattt attctatgat aaagatgagg ggaaagatac acagtta               527
```

```
<210> SEQ ID NO 46
<211> LENGTH: 33
<212> TYPE: DNA
<213> ORGANISM: artificial sequence
<220> FEATURE:
<223> OTHER INFORMATION: Probe Sequence

<400> SEQUENCE: 46
atataatttt tttaacagag aaattgcata aca                                 33
```

<210> SEQ ID NO 47
<211> LENGTH: 33
<212> TYPE: DNA
<213> ORGANISM: artificial sequence
<220> FEATURE:
<223> OTHER INFORMATION: Probe Sequence

<400> SEQUENCE: 47
atataatttt tttaacggag aaattgcata aca                                      33

<210> SEQ ID NO 48
<211> LENGTH: 33
<212> TYPE: DNA
<213> ORGANISM: artificial sequence
<220> FEATURE:
<223> OTHER INFORMATION: Probe Sequence

<400> SEQUENCE: 48
ttcaagtcca cagatacagc ttttcatatg tga                                      33

<210> SEQ ID NO 49
<211> LENGTH: 33
<212> TYPE: DNA
<213> ORGANISM: artificial sequence
<220> FEATURE:
<223> OTHER INFORMATION: Probe Sequence

<400> SEQUENCE: 49
ttcaagtcca cagatatagc ttttcatatg tga                                      33

<210> SEQ ID NO 50
<211> LENGTH: 52
<212> TYPE: DNA
<213> ORGANISM: artificial sequence
<220> FEATURE:
<223> OTHER INFORMATION: Probe Sequence

<400> SEQUENCE: 50
tccctggggg aggtgtgacg gcagagctgc atttttatgg tatgccccaa ca                 52

<210> SEQ ID NO 51
<211> LENGTH: 52
<212> TYPE: DNA
<213> ORGANISM: artificial sequence
<220> FEATURE:
<223> OTHER INFORMATION: Probe Sequence

<400> SEQUENCE: 51
tccctggggg aggtgtgacg gcagagttgc atttttatgg tatgccccaa ca                 52

<210> SEQ ID NO 52
<211> LENGTH: 52
<212> TYPE: DNA
<213> ORGANISM: artificial sequence
<220> FEATURE:
<223> OTHER INFORMATION: Probe Sequence

<400> SEQUENCE: 52
ctgttgtaaa gcaaaataga atcctaaacc agaacttctg cagttagcca ca                 52

<210> SEQ ID NO 53
<211> LENGTH: 52
<212> TYPE: DNA
<213> ORGANISM: artificial sequence
<220> FEATURE:
<223> OTHER INFORMATION: Probe Sequence

```
<400> SEQUENCE: 53
ctgttgtaaa gcaaaataga atcctacacc agaacttctg cagttagcca ca         52

<210> SEQ ID NO 54
<211> LENGTH: 52
<212> TYPE: DNA
<213> ORGANISM: artificial sequence
<220> FEATURE:
<223> OTHER INFORMATION: Probe Sequence

<400> SEQUENCE: 54
aaacttttac aaccagaatt aatgttccct tgtgctcttt taaaaaatca aa         52

<210> SEQ ID NO 55
<211> LENGTH: 52
<212> TYPE: DNA
<213> ORGANISM: artificial sequence
<220> FEATURE:
<223> OTHER INFORMATION: Probe Sequence

<400> SEQUENCE: 55
aaacttttac aaccagaatt aatgtttcct tgtgctcttt taaaaaatca aa         52

<210> SEQ ID NO 56
<211> LENGTH: 52
<212> TYPE: DNA
<213> ORGANISM: artificial sequence
<220> FEATURE:
<223> OTHER INFORMATION: Probe Sequence

<400> SEQUENCE: 56
gggtataggt gtatgtaatc agtttggttt catcttctaa ctttgcacag ca         52

<210> SEQ ID NO 57
<211> LENGTH: 52
<212> TYPE: DNA
<213> ORGANISM: artificial sequence
<220> FEATURE:
<223> OTHER INFORMATION: Probe sequence

<400> SEQUENCE: 57
gggtataggt gtatgtaatc agttttgttt catcttctaa ctttgcacag ca         52

<210> SEQ ID NO 58
<211> LENGTH: 52
<212> TYPE: DNA
<213> ORGANISM: artificial sequence
<220> FEATURE:
<223> OTHER INFORMATION: Probe Sequence

<400> SEQUENCE: 58
agatgaaaca aaactgatta catacaccta taccctgcca ctaattaaaa at         52

<210> SEQ ID NO 59
<211> LENGTH: 52
<212> TYPE: DNA
<213> ORGANISM: artificial sequence
<220> FEATURE:
<223> OTHER INFORMATION: Probe Sequence

<400> SEQUENCE: 59
agatgaaaca aaactgatta catacatcta taccctgcca ctaattaaaa at         52

<210> SEQ ID NO 60
<211> LENGTH: 52
```

```
<212> TYPE: DNA
<213> ORGANISM: artificial sequence
<220> FEATURE:
<223> OTHER INFORMATION: Probe Sequence

<400> SEQUENCE: 60
tctttgttca gaagcacggt acattactat acagctgaag ccctctagca tt            52

<210> SEQ ID NO 61
<211> LENGTH: 52
<212> TYPE: DNA
<213> ORGANISM: artificial sequence
<220> FEATURE:
<223> OTHER INFORMATION: Probe Sequence

<400> SEQUENCE: 61
tctttgttca gaagcacggt acattattat acagctgaag ccctctagca tt            52

<210> SEQ ID NO 62
<211> LENGTH: 52
<212> TYPE: DNA
<213> ORGANISM: artificial sequence
<220> FEATURE:
<223> OTHER INFORMATION: Probe Sequence

<400> SEQUENCE: 62
gatcctccct ataaaggcc taaaacacca ccattagagt tttactgctt ta            52

<210> SEQ ID NO 63
<211> LENGTH: 52
<212> TYPE: DNA
<213> ORGANISM: artificial sequence
<220> FEATURE:
<223> OTHER INFORMATION: Probe Sequence

<400> SEQUENCE: 63
gatcctccct ataaaggcc taaaacgcca ccattagagt tttactgctt ta            52

<210> SEQ ID NO 64
<211> LENGTH: 52
<212> TYPE: DNA
<213> ORGANISM: artificial sequence
<220> FEATURE:
<223> OTHER INFORMATION: probe sequence

<400> SEQUENCE: 64
aggtatccac acacacccat ttcttacaca cacatcccat atcattctcg at            52

<210> SEQ ID NO 65
<211> LENGTH: 52
<212> TYPE: DNA
<213> ORGANISM: artificial sequence
<220> FEATURE:
<223> OTHER INFORMATION: probe sequence

<400> SEQUENCE: 65
aggtatccac acacacccat ttcttataca cacatcccat atcattctcg at            52

<210> SEQ ID NO 66
<211> LENGTH: 61
<212> TYPE: DNA
<213> ORGANISM: artificial sequence
<220> FEATURE:
<223> OTHER INFORMATION: probe sequence

<400> SEQUENCE: 66
agtaaagccc gggtcctaac attttattga atggtactaa ccaagaccag caggaatgaa    60
```

-continued a                                                              61

<210> SEQ ID NO 67
<211> LENGTH: 61
<212> TYPE: DNA
<213> ORGANISM: artificial sequence
<220> FEATURE:
<223> OTHER INFORMATION: probe sequence

<400> SEQUENCE: 67
agtaaagccc gggtcctaac attttattga gtggtactaa ccaagaccag caggaatgaa    60
a                                                              61

<210> SEQ ID NO 68
<211> LENGTH: 61
<212> TYPE: DNA
<213> ORGANISM: artificial sequence
<220> FEATURE:
<223> OTHER INFORMATION: probe sequence

<400> SEQUENCE: 68
acctctataa ttccagcttc ttttcttctt gggtagctaa atcaccaaaa aaaatttttt    60
g                                                              61

<210> SEQ ID NO 69
<211> LENGTH: 61
<212> TYPE: DNA
<213> ORGANISM: artificial sequence
<220> FEATURE:
<223> OTHER INFORMATION: probe sequence

<400> SEQUENCE: 69
acctctataa ttccagcttc ttttcttctt aggtagctaa atcaccaaaa aaaatttttt    60
g                                                              61

<210> SEQ ID NO 70
<211> LENGTH: 61
<212> TYPE: DNA
<213> ORGANISM: artificial sequence
<220> FEATURE:
<223> OTHER INFORMATION: probe sequence

<400> SEQUENCE: 70
ctatgaacat tattttgcct tgacactttt tacatagcac ccaaatctta tgtatttaat    60
t                                                              61

<210> SEQ ID NO 71
<211> LENGTH: 61
<212> TYPE: DNA
<213> ORGANISM: artificial sequence
<220> FEATURE:
<223> OTHER INFORMATION: probe sequence

<400> SEQUENCE: 71
ctatgaacat tattttgcct tgacactttt cacatagcac ccaaatctta tgtatttaat    60
t                                                              61

<210> SEQ ID NO 72
<211> LENGTH: 52
<212> TYPE: DNA
<213> ORGANISM: artificial sequence
<220> FEATURE:
<223> OTHER INFORMATION: probe sequence

<400> SEQUENCE: 72
ctcatttcta ggcagaactg agtgtccttc cctaaactgc ctgtatccat ta    52

<210> SEQ ID NO 73
<211> LENGTH: 52
<212> TYPE: DNA
<213> ORGANISM: artificial sequence
<220> FEATURE:
<223> OTHER INFORMATION: probe sequence

<400> SEQUENCE: 73
ctcatttcta ggcagaactg agtgtctttc cctaaactgc ctgtatccat ta    52

<210> SEQ ID NO 74
<211> LENGTH: 52
<212> TYPE: DNA
<213> ORGANISM: artificial sequence
<220> FEATURE:
<223> OTHER INFORMATION: probe sequence

<400> SEQUENCE: 74
tgatgatgtg atgcaataca agtctcagaa tttgttggtg agagtgtaat tt    52

<210> SEQ ID NO 75
<211> LENGTH: 52
<212> TYPE: DNA
<213> ORGANISM: artificial sequence
<220> FEATURE:
<223> OTHER INFORMATION: probe sequence

<400> SEQUENCE: 75
tgatgatgtg atgcaataca agtctcggaa tttgttggtg agagtgtaat tt    52

<210> SEQ ID NO 76
<211> LENGTH: 52
<212> TYPE: DNA
<213> ORGANISM: artificial sequence
<220> FEATURE:
<223> OTHER INFORMATION: probe sequence

<400> SEQUENCE: 76 tcttttcat ggctgtttct accatcctgg aaataataat ttttaactct ct    52

<210> SEQ ID NO 77
<211> LENGTH: 52
<212> TYPE: DNA
<213> ORGANISM: artificial sequence
<220> FEATURE:
<223> OTHER INFORMATION: probe sequence

<400> SEQUENCE: 77 tcttttcat ggctgtttct accatcttgg aaataataat ttttaactct ct    52

<210> SEQ ID NO 78
<211> LENGTH: 52
<212> TYPE: DNA
<213> ORGANISM: artificial sequence
<220> FEATURE:
<223> OTHER INFORMATION: probe sequence

<400> SEQUENCE: 78
tatatgtact tattcaacat aaatccactg tttagaaaaa agtattatag ct    52

<210> SEQ ID NO 79
<211> LENGTH: 52

```
<212> TYPE: DNA
<213> ORGANISM: artificial sequence
<220> FEATURE:
<223> OTHER INFORMATION: probe sequence

<400> SEQUENCE: 79
tatatgtact tattcaacat aaatcctctg tttagaaaaa agtattatag ct            52

<210> SEQ ID NO 80
<211> LENGTH: 52
<212> TYPE: DNA
<213> ORGANISM: artificial sequence
<220> FEATURE:
<223> OTHER INFORMATION: probe sequence

<400> SEQUENCE: 80
taccttgtaa aaataatcc agaaagcagt tcaagatcag cctaggcaat at            52

<210> SEQ ID NO 81
<211> LENGTH: 52
<212> TYPE: DNA
<213> ORGANISM: artificial sequence
<220> FEATURE:
<223> OTHER INFORMATION: probe sequence

<400> SEQUENCE: 81
taccttgtaa aaataatcc agaaaggagt tcaagatcag cctaggcaat at            52

<210> SEQ ID NO 82
<211> LENGTH: 52
<212> TYPE: DNA
<213> ORGANISM: artificial sequence
<220> FEATURE:
<223> OTHER INFORMATION: probe sequence

<400> SEQUENCE: 82
tgttcagtat tatcaagctg tatatacgtt tcgacatttc atatacatga tc            52

<210> SEQ ID NO 83
<211> LENGTH: 52
<212> TYPE: DNA
<213> ORGANISM: artificial sequence
<220> FEATURE:
<223> OTHER INFORMATION: probe sequence

<400> SEQUENCE: 83
tgttcagtat tatcaagctg tatatatgtt tcgacatttc atatacatga tc            52

<210> SEQ ID NO 84
<211> LENGTH: 52
<212> TYPE: DNA
<213> ORGANISM: artificial sequence
<220> FEATURE:
<223> OTHER INFORMATION: probe sequence

<400> SEQUENCE: 84
aaacacaaac aatgagatgc tattgtcttc caatcagcct agcaaaacca ga            52

<210> SEQ ID NO 85
<211> LENGTH: 52
<212> TYPE: DNA
<213> ORGANISM: artificial sequence
<220> FEATURE:
<223> OTHER INFORMATION: probe sequence

<400> SEQUENCE: 85
aaacacaaac aatgagatgc tattgttttc caatcagcct agcaaaacca ga            52
```

<210> SEQ ID NO 86
<211> LENGTH: 53
<212> TYPE: DNA
<213> ORGANISM: artificial sequence
<220> FEATURE:
<223> OTHER INFORMATION: probe sequence

<400> SEQUENCE: 86
taactgcaac aactcagtgt ggataccatc atcatgtgaa agtcacccat gac    53

<210> SEQ ID NO 87
<211> LENGTH: 53
<212> TYPE: DNA
<213> ORGANISM: artificial sequence
<220> FEATURE:
<223> OTHER INFORMATION: probe sequence

<400> SEQUENCE: 87
taactgcaac aactcagtgt ggatactatc atcatgtgaa agtcacccat gac    53

<210> SEQ ID NO 88
<211> LENGTH: 52
<212> TYPE: DNA
<213> ORGANISM: artificial sequence
<220> FEATURE:
<223> OTHER INFORMATION: probe sequence

<400> SEQUENCE: 88
tgctctggca gaagaggcac atgttgaaca aatggctgca ttatggtgag at    52

<210> SEQ ID NO 89
<211> LENGTH: 52
<212> TYPE: DNA
<213> ORGANISM: artificial sequence
<220> FEATURE:
<223> OTHER INFORMATION: probe sequence

<400> SEQUENCE: 89
tgctctggca gaagaggcac atgttggaca aatggctgca ttatggtgag at    52

<210> SEQ ID NO 90
<211> LENGTH: 52
<212> TYPE: DNA
<213> ORGANISM: artificial sequence
<220> FEATURE:
<223> OTHER INFORMATION: probe sequence

<400> SEQUENCE: 90
acacatcttc tcccctatta tactcaacca gcaagcattc ccacctttaa gc    52

<210> SEQ ID NO 91
<211> LENGTH: 52
<212> TYPE: DNA
<213> ORGANISM: artificial sequence
<220> FEATURE:
<223> OTHER INFORMATION: probe sequence

<400> SEQUENCE: 91
acacatcttc tcccctatta tactcagcca gcaagcattc ccacctttaa gc    52

<210> SEQ ID NO 92
<211> LENGTH: 61
<212> TYPE: DNA
<213> ORGANISM: artificial sequence
<220> FEATURE:
<223> OTHER INFORMATION: probe sequence

```
<400> SEQUENCE: 92
ttattgccct tatttacttc tccaaacatt aatctggtct catcgtttgc aaaggtgttg     60
c                                                                    61

<210> SEQ ID NO 93
<211> LENGTH: 61
<212> TYPE: DNA
<213> ORGANISM: artificial sequence
<220> FEATURE:
<223> OTHER INFORMATION: probe sequence

<400> SEQUENCE: 93
ttattgccct tatttacttc tccaaacatt gatctggtct catcgtttgc aaaggtgttg     60
c                                                                    61

<210> SEQ ID NO 94
<211> LENGTH: 52
<212> TYPE: DNA
<213> ORGANISM: artificial sequence
<220> FEATURE:
<223> OTHER INFORMATION: probe sequence

<400> SEQUENCE: 94
ggcagagatt ctggggactg gaaagaacta gttatgatca aggaaccaaa ag             52

<210> SEQ ID NO 95
<211> LENGTH: 52
<212> TYPE: DNA
<213> ORGANISM: artificial sequence
<220> FEATURE:
<223> OTHER INFORMATION: probe sequence

<400> SEQUENCE: 95
ggcagagatt ctggggactg gaaagagcta gttatgatca aggaaccaaa ag             52

<210> SEQ ID NO 96
<211> LENGTH: 52
<212> TYPE: DNA
<213> ORGANISM: artificial sequence
<220> FEATURE:
<223> OTHER INFORMATION: probe sequence

<400> SEQUENCE: 96
tttattttct atagcaggtt tattgacact ttttttctag taaagtttga aa             52

<210> SEQ ID NO 97
<211> LENGTH: 52
<212> TYPE: DNA
<213> ORGANISM: artificial sequence
<220> FEATURE:
<223> OTHER INFORMATION: probe sequence

<400> SEQUENCE: 97
tttattttct atagcaggtt tattgatact ttttttctag taaagtttga aa             52

<210> SEQ ID NO 98
<211> LENGTH: 52
<212> TYPE: DNA
<213> ORGANISM: artificial sequence
<220> FEATURE:
<223> OTHER INFORMATION: probe sequence

<400> SEQUENCE: 98
tgctgaaaaa aatgattgga tgatagatcg gattaagaag ggaagaaata gc             52
```

<210> SEQ ID NO 99
<211> LENGTH: 52
<212> TYPE: DNA
<213> ORGANISM: artificial sequence
<220> FEATURE:
<223> OTHER INFORMATION: probe sequence

<400> SEQUENCE: 99
tgctgaaaaa aatgattgga tgatagttcg gattaagaag ggaagaaata gc    52

<210> SEQ ID NO 100
<211> LENGTH: 33
<212> TYPE: DNA
<213> ORGANISM: artificial sequence
<220> FEATURE:
<223> OTHER INFORMATION: probe sequence

<400> SEQUENCE: 100
ctaaaaagga acaaaactat gttgcataac tca    33

<210> SEQ ID NO 101
<211> LENGTH: 33
<212> TYPE: DNA
<213> ORGANISM: artificial sequence
<220> FEATURE:
<223> OTHER INFORMATION: probe sequence

<400> SEQUENCE: 101
ctaaaaagga acaaaaatat gttgcataac tca    33

<210> SEQ ID NO 102
<211> LENGTH: 61
<212> TYPE: DNA
<213> ORGANISM: artificial sequence
<220> FEATURE:
<223> OTHER INFORMATION: probe sequence

<400> SEQUENCE: 102
ctttgatgct gtgagacgaa ggcatcttgt cagtgccctg ggattgagat ctttcattgg    60
t    61

<210> SEQ ID NO 103
<211> LENGTH: 61
<212> TYPE: DNA
<213> ORGANISM: artificial sequence
<220> FEATURE:
<223> OTHER INFORMATION: probe sequence

<400> SEQUENCE: 103
ctttgatgct gtgagacgaa ggcatcttgt tagtgccctg ggattgagat ctttcattgg    60
t    61

<210> SEQ ID NO 104
<211> LENGTH: 52
<212> TYPE: DNA
<213> ORGANISM: artificial sequence
<220> FEATURE:
<223> OTHER INFORMATION: probe sequence

<400> SEQUENCE: 104
aaaaacaggt gtcaggctgg atttgaccca ttggctgtag ttcagtgaca ct    52

<210> SEQ ID NO 105
<211> LENGTH: 52

```
<212> TYPE: DNA
<213> ORGANISM: artificial sequence
<220> FEATURE:
<223> OTHER INFORMATION: probe sequence

<400> SEQUENCE: 105
aaaaacaggt gtcaggctgg atttgatcca ttggctgtag ttcagtgaca ct         52

<210> SEQ ID NO 106
<211> LENGTH: 52
<212> TYPE: DNA
<213> ORGANISM: artificial sequence
<220> FEATURE:
<223> OTHER INFORMATION: probe sequence

<400> SEQUENCE: 106
tcaattctgg aattggaagg gaatccaagg agatctatac caggcaatgc at         52

<210> SEQ ID NO 107
<211> LENGTH: 52
<212> TYPE: DNA
<213> ORGANISM: artificial sequence
<220> FEATURE:
<223> OTHER INFORMATION: probe sequence

<400> SEQUENCE: 107
tcaattctgg aattggaagg gaatccgagg agatctatac caggcaatgc at         52

<210> SEQ ID NO 108
<211> LENGTH: 52
<212> TYPE: DNA
<213> ORGANISM: artificial sequence
<220> FEATURE:
<223> OTHER INFORMATION: probe sequence

<400> SEQUENCE: 108
cccaccaaag acagttttgc ttgggtcctc tcaaagctat gctgttgggt tt         52

<210> SEQ ID NO 109
<211> LENGTH: 52
<212> TYPE: DNA
<213> ORGANISM: artificial sequence
<220> FEATURE:
<223> OTHER INFORMATION: probe sequence

<400> SEQUENCE: 109
cccaccaaag acagttttgc ttgggttctc tcaaagctat gctgttgggt tt         52

<210> SEQ ID NO 110
<211> LENGTH: 61
<212> TYPE: DNA
<213> ORGANISM: artificial sequence
<220> FEATURE:
<223> OTHER INFORMATION: probe sequence

<400> SEQUENCE: 110
gtgtgctgtg ttgggtgtgt gaacattcct aagacgtcca taagctgatt tataaaaact   60
t                                                                   61

<210> SEQ ID NO 111
<211> LENGTH: 61
<212> TYPE: DNA
<213> ORGANISM: artificial sequence
<220> FEATURE:
<223> OTHER INFORMATION: probe sequence

<400> SEQUENCE: 111
```

```
gtgtgctgtg ttgggtgtgt gaacattcct gagacgtcca taagctgatt tataaaaact    60
t                                                                    61

<210> SEQ ID NO 112
<211> LENGTH: 61
<212> TYPE: DNA
<213> ORGANISM: artificial sequence
<220> FEATURE:
<223> OTHER INFORMATION: probe sequence

<400> SEQUENCE: 112
ctccaggaag cagccatgcc tgatgtgtgc aatgaatatg ccttatcctc ccgaaactgg    60
c                                                                    61

<210> SEQ ID NO 113
<211> LENGTH: 61
<212> TYPE: DNA
<213> ORGANISM: artificial sequence
<220> FEATURE:
<223> OTHER INFORMATION: probe sequence

<400> SEQUENCE: 113
ctccaggaag cagccatgcc tgatgtgtgc gatgaatatg ccttatcctc ccgaaactgg    60
c                                                                    61

<210> SEQ ID NO 114
<211> LENGTH: 61
<212> TYPE: DNA
<213> ORGANISM: artificial sequence
<220> FEATURE:
<223> OTHER INFORMATION: probe sequence

<400> SEQUENCE: 114
ggattgacca ctgtcaagtc acagagtcac gaattgtcta gaatcaatat tatgtagact    60
a                                                                    61

<210> SEQ ID NO 115
<211> LENGTH: 61
<212> TYPE: DNA
<213> ORGANISM: artificial sequence
<220> FEATURE:
<223> OTHER INFORMATION: probe sequence

<400> SEQUENCE: 115
ggattgacca ctgtcaagtc acagagtcac aaattgtcta gaatcaatat tatgtagact    60
a                                                                    61

<210> SEQ ID NO 116
<211> LENGTH: 52
<212> TYPE: DNA
<213> ORGANISM: artificial sequence
<220> FEATURE:
<223> OTHER INFORMATION: probe sequence

<400> SEQUENCE: 116
catatgtaat gtgcatttat cccccccagtg cattacctta caattgtccg ta           52

<210> SEQ ID NO 117
<211> LENGTH: 52
<212> TYPE: DNA
<213> ORGANISM: artificial sequence
<220> FEATURE:
<223> OTHER INFORMATION: probe sequence
```

<400> SEQUENCE: 117
catatgtaat gtgcatttat cccccggtg cattaccta caattgtccg ta         52

<210> SEQ ID NO 118
<211> LENGTH: 61
<212> TYPE: DNA
<213> ORGANISM: artificial sequence
<220> FEATURE:
<223> OTHER INFORMATION: probe sequence

<400> SEQUENCE: 118
agataaacag ggtagttgta gttgcaacag ggtagataga ggtaggtcta ccctgggttt   60
a                                                                  61

<210> SEQ ID NO 119
<211> LENGTH: 61
<212> TYPE: DNA
<213> ORGANISM: artificial sequence
<220> FEATURE:
<223> OTHER INFORMATION: probe sequence

<400> SEQUENCE: 119
agataaacag ggtagttgta gttgcaacag agtagataga ggtaggtcta ccctgggttt   60
a                                                                  61

<210> SEQ ID NO 120
<211> LENGTH: 52
<212> TYPE: DNA
<213> ORGANISM: artificial sequence
<220> FEATURE:
<223> OTHER INFORMATION: probe sequence

<400> SEQUENCE: 120
caaggaaacc aaggaagatt tttctccttc agaactcgga ccctgaatac ca           52

<210> SEQ ID NO 121
<211> LENGTH: 52
<212> TYPE: DNA
<213> ORGANISM: artificial sequence
<220> FEATURE:
<223> OTHER INFORMATION: probe sequence

<400> SEQUENCE: 121
caaggaaacc aaggaagatt tttctctttc agaactcgga ccctgaatac ca           52

<210> SEQ ID NO 122
<211> LENGTH: 61
<212> TYPE: DNA
<213> ORGANISM: artificial sequence
<220> FEATURE:
<223> OTHER INFORMATION: probe sequence

<400> SEQUENCE: 122
ctcaggtccc tgactcagca gcccaccagg gcagaccatt ccagtctcct ggaatctaaa   60
c                                                                  61

<210> SEQ ID NO 123
<211> LENGTH: 61
<212> TYPE: DNA
<213> ORGANISM: artificial sequence
<220> FEATURE:
<223> OTHER INFORMATION: probe sequence

<400> SEQUENCE: 123

```
ctcaggtccc tgactcagca gcccaccagg acagaccatt ccagtctcct ggaatctaaa    60
c                                                                    61

<210> SEQ ID NO 124
<211> LENGTH: 61
<212> TYPE: DNA
<213> ORGANISM: artificial sequence
<220> FEATURE:
<223> OTHER INFORMATION: probe sequence

<400> SEQUENCE: 124
caacaaatag tgaagagact tttgaatcta tagggcagca cttaagggat ctagggtggc    60
a                                                                    61

<210> SEQ ID NO 125
<211> LENGTH: 61
<212> TYPE: DNA
<213> ORGANISM: artificial sequence
<220> FEATURE:
<223> OTHER INFORMATION: probe sequence

<400> SEQUENCE: 125
caacaaatag tgaagagact tttgaatcta gagggcagca cttaagggat ctagggtggc    60
a                                                                    61

<210> SEQ ID NO 126
<211> LENGTH: 33
<212> TYPE: DNA
<213> ORGANISM: artificial sequence
<220> FEATURE:
<223> OTHER INFORMATION: probe sequence

<400> SEQUENCE: 126
ggccttggga catttgcaaa caaagctgtt gat                                  33

<210> SEQ ID NO 127
<211> LENGTH: 33
<212> TYPE: DNA
<213> ORGANISM: artificial sequence
<220> FEATURE:
<223> OTHER INFORMATION: probe sequence

<400> SEQUENCE: 127
ggccttggga catttgaaaa caaagctgtt gat                                  33

<210> SEQ ID NO 128
<211> LENGTH: 52
<212> TYPE: DNA
<213> ORGANISM: artificial sequence
<220> FEATURE:
<223> OTHER INFORMATION: probe sequence

<400> SEQUENCE: 128
gttattttcc ctattaaaga acatccgctc atagttttc aagttattat gt              52

<210> SEQ ID NO 129
<211> LENGTH: 52
<212> TYPE: DNA
<213> ORGANISM: artificial sequence
<220> FEATURE:
<223> OTHER INFORMATION: probe sequence

<400> SEQUENCE: 129
gttattttcc ctattaaaga acatcctctc atagttttc aagttattat gt              52
```

<210> SEQ ID NO 130
<211> LENGTH: 61
<212> TYPE: DNA
<213> ORGANISM: artificial sequence
<220> FEATURE:
<223> OTHER INFORMATION: probe sequence

<400> SEQUENCE: 130
gcattttata caacctcact gcatcagcct gttaaaagca agaggtctga ttcacatacg    60
a                                                                    61

<210> SEQ ID NO 131
<211> LENGTH: 61
<212> TYPE: DNA
<213> ORGANISM: artificial sequence
<220> FEATURE:
<223> OTHER INFORMATION: probe sequence

<400> SEQUENCE: 131
gcattttata caacctcact gcatcagcct attaaaagca agaggtctga ttcacatacg    60
a                                                                    61

<210> SEQ ID NO 132
<211> LENGTH: 52
<212> TYPE: DNA
<213> ORGANISM: artificial sequence
<220> FEATURE:
<223> OTHER INFORMATION: probe sequence

<400> SEQUENCE: 132
attcgttgac tattttagct ggtgacacaa tgaaaaaaca gagtctaagc aa            52

<210> SEQ ID NO 133
<211> LENGTH: 52
<212> TYPE: DNA
<213> ORGANISM: artificial sequence
<220> FEATURE:
<223> OTHER INFORMATION: probe sequence

<400> SEQUENCE: 133
attcgttgac tattttagct ggtgacgcaa tgaaaaaaca gagtctaagc aa            52

<210> SEQ ID NO 134
<211> LENGTH: 61
<212> TYPE: DNA
<213> ORGANISM: artificial sequence
<220> FEATURE:
<223> OTHER INFORMATION: probe sequence

<400> SEQUENCE: 134
aggcctgcca gttttagggg ccatttggct cctgagaaga actgttaata aaagtattaa    60
t                                                                    61

<210> SEQ ID NO 135
<211> LENGTH: 61
<212> TYPE: DNA
<213> ORGANISM: artificial sequence
<220> FEATURE:
<223> OTHER INFORMATION: probe sequence

<400> SEQUENCE: 135
aggcctgcca gttttagggg ccatttggct tctgagaaga actgttaata aaagtattaa    60
t                                                                    61

<210> SEQ ID NO 136
<211> LENGTH: 20
<212> TYPE: DNA
<213> ORGANISM: artificial sequence
<220> FEATURE:
<223> OTHER INFORMATION: primer sequence

<400> SEQUENCE: 136
cgggttcaag tggttctgct                                          20

<210> SEQ ID NO 137
<211> LENGTH: 24
<212> TYPE: DNA
<213> ORGANISM: artificial sequence
<220> FEATURE:
<223> OTHER INFORMATION: primer sequence

<400> SEQUENCE: 137
gttgttgttg ttcctatggt ttcc                                     24

<210> SEQ ID NO 138
<211> LENGTH: 26
<212> TYPE: DNA
<213> ORGANISM: artificial sequence
<220> FEATURE:
<223> OTHER INFORMATION: primer sequence

<400> SEQUENCE: 138
agataacaac tctatgctct ggcttc                                   26

<210> SEQ ID NO 139
<211> LENGTH: 21
<212> TYPE: DNA
<213> ORGANISM: artificial sequence
<220> FEATURE:
<223> OTHER INFORMATION: primer sequence

<400> SEQUENCE: 139
aaggcccttc agtgctgttc t                                        21

<210> SEQ ID NO 140
<211> LENGTH: 20
<212> TYPE: DNA
<213> ORGANISM: artificial sequence
<220> FEATURE:
<223> OTHER INFORMATION: primer sequence

<400> SEQUENCE: 140
atctgccatt ccgatttcca                                          20

<210> SEQ ID NO 141
<211> LENGTH: 22
<212> TYPE: DNA
<213> ORGANISM: artificial sequence
<220> FEATURE:
<223> OTHER INFORMATION: primer sequence

<400> SEQUENCE: 141
caagaaaggc aggatggatg tt                                       22

<210> SEQ ID NO 142
<211> LENGTH: 23
<212> TYPE: DNA
<213> ORGANISM: artificial sequence
<220> FEATURE:
<223> OTHER INFORMATION: primer sequence

```
<400> SEQUENCE: 142
tctgcctggg aagtgtaagt ctc                                              23

<210> SEQ ID NO 143
<211> LENGTH: 25
<212> TYPE: DNA
<213> ORGANISM: artificial sequence
<220> FEATURE:
<223> OTHER INFORMATION: primer sequence

<400> SEQUENCE: 143
atactccagt cactttcctg tctcc                                            25

<210> SEQ ID NO 144
<211> LENGTH: 23
<212> TYPE: DNA
<213> ORGANISM: artificial sequence
<220> FEATURE:
<223> OTHER INFORMATION: primer sequence

<400> SEQUENCE: 144
tctgtcttgc tttcttagcc tcc                                              23

<210> SEQ ID NO 145
<211> LENGTH: 26
<212> TYPE: DNA
<213> ORGANISM: artificial sequence
<220> FEATURE:
<223> OTHER INFORMATION: primer sequence

<400> SEQUENCE: 145
tgtgctattg ttgttcactt ctatgg                                           26

<210> SEQ ID NO 146
<211> LENGTH: 21
<212> TYPE: DNA
<213> ORGANISM: artificial sequence
<220> FEATURE:
<223> OTHER INFORMATION: primer sequence

<400> SEQUENCE: 146
cagcggtatg atttcgtagt g                                                21

<210> SEQ ID NO 147
<211> LENGTH: 22
<212> TYPE: DNA
<213> ORGANISM: artificial sequence
<220> FEATURE:
<223> OTHER INFORMATION: primer sequence

<400> SEQUENCE: 147
gctaaaatct catcacctgg ac                                               22

<210> SEQ ID NO 148
<211> LENGTH: 22
<212> TYPE: DNA
<213> ORGANISM: artificial sequence
<220> FEATURE:
<223> OTHER INFORMATION: primer sequence

<400> SEQUENCE: 148
aagtagctgc ccaaacaatg tg                                               22

<210> SEQ ID NO 149
<211> LENGTH: 20
```

```
<212> TYPE: DNA
<213> ORGANISM: artificial sequence
<220> FEATURE:
<223> OTHER INFORMATION: primer sequence

<400> SEQUENCE: 149
caggcttggg accagattgt                                          20

<210> SEQ ID NO 150
<211> LENGTH: 25
<212> TYPE: DNA
<213> ORGANISM: artificial sequence
<220> FEATURE:
<223> OTHER INFORMATION: primer sequence

<400> SEQUENCE: 150
taaaccaagc tccaatttct catag                                    25

<210> SEQ ID NO 151
<211> LENGTH: 26
<212> TYPE: DNA
<213> ORGANISM: artificial sequence
<220> FEATURE:
<223> OTHER INFORMATION: primer sequence

<400> SEQUENCE: 151 cacacccttta ctactgtttc ctatgc                                  26

<210> SEQ ID NO 152
<211> LENGTH: 22
<212> TYPE: DNA
<213> ORGANISM: artificial sequence
<220> FEATURE:
<223> OTHER INFORMATION: primer sequence

<400> SEQUENCE: 152
agactcagat gagatgccac at                                       22

<210> SEQ ID NO 153
<211> LENGTH: 22
<212> TYPE: DNA
<213> ORGANISM: artificial sequence
<220> FEATURE:
<223> OTHER INFORMATION: primer sequence

<400> SEQUENCE: 153
ttacctgtcc aactccagaa tg                                       22

<210> SEQ ID NO 154
<211> LENGTH: 20
<212> TYPE: DNA
<213> ORGANISM: artificial sequence
<220> FEATURE:
<223> OTHER INFORMATION: primer sequence

<400> SEQUENCE: 154
aggctgaagc aggagaatcg                                          20

<210> SEQ ID NO 155
<211> LENGTH: 24
<212> TYPE: DNA
<213> ORGANISM: artificial sequence
<220> FEATURE:
<223> OTHER INFORMATION: primer sequence

<400> SEQUENCE: 155
ggagacgacc ttagactgta gcat                                     24
```

```
<210> SEQ ID NO 156
<211> LENGTH: 24
<212> TYPE: DNA
<213> ORGANISM: artificial sequence
<220> FEATURE:
<223> OTHER INFORMATION: primer sequence

<400> SEQUENCE: 156
tcatcgctca ttcagtcatc agtt                                              24

<210> SEQ ID NO 157
<211> LENGTH: 22
<212> TYPE: DNA
<213> ORGANISM: artificial sequence
<220> FEATURE:
<223> OTHER INFORMATION: primer sequence

<400> SEQUENCE: 157
gccaacatct ttgctgagga at                                                22

<210> SEQ ID NO 158
<211> LENGTH: 26
<212> TYPE: DNA
<213> ORGANISM: artificial sequence
<220> FEATURE:
<223> OTHER INFORMATION: primer sequence

<400> SEQUENCE: 158
attaatatgg ccaactcaaa tgaact                                            26

<210> SEQ ID NO 159
<211> LENGTH: 21
<212> TYPE: DNA
<213> ORGANISM: artificial sequence
<220> FEATURE:
<223> OTHER INFORMATION: primer sequence

<400> SEQUENCE: 159
gctggagaag ggtagaggtg c                                                 21

<210> SEQ ID NO 160
<211> LENGTH: 21
<212> TYPE: DNA
<213> ORGANISM: artificial sequence
<220> FEATURE:
<223> OTHER INFORMATION: primer sequence

<400> SEQUENCE: 160
aaaggacatc gacaggcatt g                                                 21

<210> SEQ ID NO 161
<211> LENGTH: 21
<212> TYPE: DNA
<213> ORGANISM: artificial sequence
<220> FEATURE:
<223> OTHER INFORMATION: primer sequence

<400> SEQUENCE: 161
gcatccgtaa tccaacacct g                                                 21

<210> SEQ ID NO 162
<211> LENGTH: 23
<212> TYPE: DNA
<213> ORGANISM: artificial sequence
<220> FEATURE:
<223> OTHER INFORMATION: primer sequence
```

<400> SEQUENCE: 162
cctattcacc tcaattgcag tcc                                                    23

<210> SEQ ID NO 163
<211> LENGTH: 21
<212> TYPE: DNA
<213> ORGANISM: artificial sequence
<220> FEATURE:
<223> OTHER INFORMATION: primer sequence

<400> SEQUENCE: 163
cttcccaaat agccagttcc a                                                      21

<210> SEQ ID NO 164
<211> LENGTH: 22
<212> TYPE: DNA
<213> ORGANISM: artificial sequence
<220> FEATURE:
<223> OTHER INFORMATION: primer sequence

<400> SEQUENCE: 164
ggttttggaa ctggctattt gg                                                     22

<210> SEQ ID NO 165
<211> LENGTH: 22
<212> TYPE: DNA
<213> ORGANISM: artificial sequence
<220> FEATURE:
<223> OTHER INFORMATION: primer sequence

<400> SEQUENCE: 165
ccgtcatcct tgtctgccta ct                                                     22

<210> SEQ ID NO 166
<211> LENGTH: 25
<212> TYPE: DNA
<213> ORGANISM: artificial sequence
<220> FEATURE:
<223> OTHER INFORMATION: primer sequence

<400> SEQUENCE: 166
ccatgagcca ttattgtaaa ctgat                                                  25

<210> SEQ ID NO 167
<211> LENGTH: 23
<212> TYPE: DNA
<213> ORGANISM: artificial sequence
<220> FEATURE:
<223> OTHER INFORMATION: primer sequence

<400> SEQUENCE: 167
tagctgggac tgtaggtgtg tgt                                                    23

<210> SEQ ID NO 168
<211> LENGTH: 24
<212> TYPE: DNA
<213> ORGANISM: artificial sequence
<220> FEATURE:
<223> OTHER INFORMATION: primer sequence

<400> SEQUENCE: 168
ttagaaatgc tggtggttgt acaa                                                   24

<210> SEQ ID NO 169
<211> LENGTH: 25

<210> SEQ ID NO 170
<211> LENGTH: 23
<212> TYPE: DNA
<213> ORGANISM: artificial sequence
<220> FEATURE:
<223> OTHER INFORMATION: primer sequence

<400> SEQUENCE: 169
ctaatgtgat cctcaaatgg ctact                                25

<210> SEQ ID NO 170
<211> LENGTH: 23
<212> TYPE: DNA
<213> ORGANISM: artificial sequence
<220> FEATURE:
<223> OTHER INFORMATION: primer sequence

<400> SEQUENCE: 170
aacccaggca aaagagaaa tag                                   23

<210> SEQ ID NO 171
<211> LENGTH: 23
<212> TYPE: DNA
<213> ORGANISM: artificial sequence
<220> FEATURE:
<223> OTHER INFORMATION: primer sequence

<400> SEQUENCE: 171
actgactctg gttttgctag gct                                  23

<210> SEQ ID NO 172
<211> LENGTH: 21
<212> TYPE: DNA
<213> ORGANISM: artificial sequence
<220> FEATURE:
<223> OTHER INFORMATION: primer sequence

<400> SEQUENCE: 172
ccaagtgtca cctctgccat c                                    21

<210> SEQ ID NO 173
<211> LENGTH: 22
<212> TYPE: DNA
<213> ORGANISM: artificial sequence
<220> FEATURE:
<223> OTHER INFORMATION: primer sequence

<400> SEQUENCE: 173
ccactgttgc aaattcattc ca                                   22

<210> SEQ ID NO 174
<211> LENGTH: 25
<212> TYPE: DNA
<213> ORGANISM: artificial sequence
<220> FEATURE:
<223> OTHER INFORMATION: primer sequence

<400> SEQUENCE: 174
gtggttctta ctctagcaca atgat                                25

<210> SEQ ID NO 175
<211> LENGTH: 25
<212> TYPE: DNA
<213> ORGANISM: artificial sequence
<220> FEATURE:
<223> OTHER INFORMATION: primer sequence

<400> SEQUENCE: 175
ccatccacat actcacttca atatc                                25

<210> SEQ ID NO 176
<211> LENGTH: 21
<212> TYPE: DNA
<213> ORGANISM: artificial sequence
<220> FEATURE:
<223> OTHER INFORMATION: primer sequence

<400> SEQUENCE: 176
caaaaccagg ctgatgacaa t                                              21

<210> SEQ ID NO 177
<211> LENGTH: 23
<212> TYPE: DNA
<213> ORGANISM: artificial sequence
<220> FEATURE:
<223> OTHER INFORMATION: primer sequence

<400> SEQUENCE: 177
gtttgagaat catagaccag cac                                            23

<210> SEQ ID NO 178
<211> LENGTH: 21
<212> TYPE: DNA
<213> ORGANISM: artificial sequence
<220> FEATURE:
<223> OTHER INFORMATION: primer sequence

<400> SEQUENCE: 178
ctccagggac tgcctctttc t                                              21

<210> SEQ ID NO 179
<211> LENGTH: 25
<212> TYPE: DNA
<213> ORGANISM: artificial sequence
<220> FEATURE:
<223> OTHER INFORMATION: primer sequence

<400> SEQUENCE: 179
tgtttatgca tgtaactgta ggtgg                                          25

<210> SEQ ID NO 180
<211> LENGTH: 21
<212> TYPE: DNA
<213> ORGANISM: artificial sequence
<220> FEATURE:
<223> OTHER INFORMATION: primer sequence

<400> SEQUENCE: 180
gagcagccac tcaagaaaca g                                              21

<210> SEQ ID NO 181
<211> LENGTH: 20
<212> TYPE: DNA
<213> ORGANISM: artificial sequence
<220> FEATURE:
<223> OTHER INFORMATION: primer sequence

<400> SEQUENCE: 181
aagccaccat ccagtctcac                                                20

<210> SEQ ID NO 182
<211> LENGTH: 24
<212> TYPE: DNA
<213> ORGANISM: artificial sequence
<220> FEATURE:
<223> OTHER INFORMATION: primer sequence

```
<400> SEQUENCE: 182
aaacaagata gggctaggct gatt                                              24

<210> SEQ ID NO 183
<211> LENGTH: 23
<212> TYPE: DNA
<213> ORGANISM: artificial sequence
<220> FEATURE:
<223> OTHER INFORMATION: primer sequence

<400> SEQUENCE: 183
catgattgac tgcctggtac tcc                                               23

<210> SEQ ID NO 184
<211> LENGTH: 25
<212> TYPE: DNA
<213> ORGANISM: artificial sequence
<220> FEATURE:
<223> OTHER INFORMATION: primer sequence

<400> SEQUENCE: 184
agaggctatt ctcagtgagc ttctc                                             25

<210> SEQ ID NO 185
<211> LENGTH: 23
<212> TYPE: DNA
<213> ORGANISM: artificial sequence
<220> FEATURE:
<223> OTHER INFORMATION: primer sequence

<400> SEQUENCE: 185
gcacagtgca tggcaatagt aag                                               23

<210> SEQ ID NO 186
<211> LENGTH: 24
<212> TYPE: DNA
<213> ORGANISM: artificial sequence
<220> FEATURE:
<223> OTHER INFORMATION: primer sequence

<400> SEQUENCE: 186
agcatacctc aagcatgaac agat                                              24

<210> SEQ ID NO 187
<211> LENGTH: 23
<212> TYPE: DNA
<213> ORGANISM: artificial sequence
<220> FEATURE:
<223> OTHER INFORMATION: primer sequence

<400> SEQUENCE: 187
aagcaatgta gaaacatggc aca                                               23

<210> SEQ ID NO 188
<211> LENGTH: 21
<212> TYPE: DNA
<213> ORGANISM: artificial sequence
<220> FEATURE:
<223> OTHER INFORMATION: primer sequence

<400> SEQUENCE: 188
gctccctcct tcaacatcca c                                                 21

<210> SEQ ID NO 189
<211> LENGTH: 22
```

```
<212> TYPE: DNA
<213> ORGANISM: artificial sequence
<220> FEATURE:
<223> OTHER INFORMATION: primer sequence

<400> SEQUENCE: 189
gcaatgccaa caagaagaca ga                                              22

<210> SEQ ID NO 190
<211> LENGTH: 23
<212> TYPE: DNA
<213> ORGANISM: artificial sequence
<220> FEATURE:
<223> OTHER INFORMATION: primer sequence

<400> SEQUENCE: 190
ctgtggctca ccttggagat tat                                             23

<210> SEQ ID NO 191
<211> LENGTH: 24
<212> TYPE: DNA
<213> ORGANISM: artificial sequence
<220> FEATURE:
<223> OTHER INFORMATION: primer sequence

<400> SEQUENCE: 191
tggctttctg ttcctacgtt agac                                            24

<210> SEQ ID NO 192
<211> LENGTH: 26
<212> TYPE: DNA
<213> ORGANISM: artificial sequence
<220> FEATURE:
<223> OTHER INFORMATION: primer sequence

<400> SEQUENCE: 192
tgttatttga ttgatggtcc tagagg                                          26

<210> SEQ ID NO 193
<211> LENGTH: 26
<212> TYPE: DNA
<213> ORGANISM: artificial sequence
<220> FEATURE:
<223> OTHER INFORMATION: primer sequence

<400> SEQUENCE: 193
ctttaggcta ctatcattgc accatt                                          26

<210> SEQ ID NO 194
<211> LENGTH: 22
<212> TYPE: DNA
<213> ORGANISM: artificial sequence
<220> FEATURE:
<223> OTHER INFORMATION: primer sequence

<400> SEQUENCE: 194
aatcctgtcc gtttccaaca ct                                              22

<210> SEQ ID NO 195
<211> LENGTH: 21
<212> TYPE: DNA
<213> ORGANISM: artificial sequence
<220> FEATURE:
<223> OTHER INFORMATION: primer sequence

<400> SEQUENCE: 195
gcacaaaccc aacagcatag c                                               21
```

```
<210> SEQ ID NO 196
<211> LENGTH: 26
<212> TYPE: DNA
<213> ORGANISM: artificial sequence
<220> FEATURE:
<223> OTHER INFORMATION: primer sequence

<400> SEQUENCE: 196
atcacaagtt tgccttctta aatatg                                              26

<210> SEQ ID NO 197
<211> LENGTH: 21
<212> TYPE: DNA
<213> ORGANISM: artificial sequence
<220> FEATURE:
<223> OTHER INFORMATION: primer sequence

<400> SEQUENCE: 197
gtgccagaag atcgcagagt t                                                   21

<210> SEQ ID NO 198
<211> LENGTH: 21
<212> TYPE: DNA
<213> ORGANISM: artificial sequence
<220> FEATURE:
<223> OTHER INFORMATION: primer sequence

<400> SEQUENCE: 198
cctcttcacc cacagcaaca t                                                   21

<210> SEQ ID NO 199
<211> LENGTH: 23
<212> TYPE: DNA
<213> ORGANISM: artificial sequence
<220> FEATURE:
<223> OTHER INFORMATION: primer sequence

<400> SEQUENCE: 199
agacagtgga agtggtcctc att                                                 23

<210> SEQ ID NO 200
<211> LENGTH: 24
<212> TYPE: DNA
<213> ORGANISM: artificial sequence
<220> FEATURE:
<223> OTHER INFORMATION: primer sequence

<400> SEQUENCE: 200
ttttctgttg tatgggatga atgg                                                24

<210> SEQ ID NO 201
<211> LENGTH: 25
<212> TYPE: DNA
<213> ORGANISM: artificial sequence
<220> FEATURE:
<223> OTHER INFORMATION: primer sequence

<400> SEQUENCE: 201
tacaaggatt gaccactgtc aagtc                                               25

<210> SEQ ID NO 202
<211> LENGTH: 23
<212> TYPE: DNA
<213> ORGANISM: artificial sequence
<220> FEATURE:
<223> OTHER INFORMATION: primer sequence
```

```
<400> SEQUENCE: 202
tgcagtaggc tgtcttcaaa tca                                            23

<210> SEQ ID NO 203
<211> LENGTH: 21
<212> TYPE: DNA
<213> ORGANISM: artificial sequence
<220> FEATURE:
<223> OTHER INFORMATION: primer sequence

<400> SEQUENCE: 203
accttgtgat gcagccactt c                                              21

<210> SEQ ID NO 204
<211> LENGTH: 21
<212> TYPE: DNA
<213> ORGANISM: artificial sequence
<220> FEATURE:
<223> OTHER INFORMATION: primer sequence

<400> SEQUENCE: 204
cgagacaggc aggttgctaa g                                              21

<210> SEQ ID NO 205
<211> LENGTH: 24
<212> TYPE: DNA
<213> ORGANISM: artificial sequence
<220> FEATURE:
<223> OTHER INFORMATION: primer sequence

<400> SEQUENCE: 205
aaagacggct attcagtgtt gttg                                           24

<210> SEQ ID NO 206
<211> LENGTH: 20
<212> TYPE: DNA
<213> ORGANISM: artificial sequence
<220> FEATURE:
<223> OTHER INFORMATION: primer sequence

<400> SEQUENCE: 206
caggctgagg caggagaatc                                                20

<210> SEQ ID NO 207
<211> LENGTH: 25
<212> TYPE: DNA
<213> ORGANISM: artificial sequence
<220> FEATURE:
<223> OTHER INFORMATION: primer sequence

<400> SEQUENCE: 207
tggccttact taggatttct tactg                                          25

<210> SEQ ID NO 208
<211> LENGTH: 22
<212> TYPE: DNA
<213> ORGANISM: artificial sequence
<220> FEATURE:
<223> OTHER INFORMATION: primer sequence

<400> SEQUENCE: 208
gagccactac gcctgtctga tt                                             22

<210> SEQ ID NO 209
<211> LENGTH: 24
```

```
<212> TYPE: DNA
<213> ORGANISM: artificial sequence
<220> FEATURE:
<223> OTHER INFORMATION: primer sequence

<400> SEQUENCE: 209
cgagatgctg agatagtggt gaag                                           24

<210> SEQ ID NO 210
<211> LENGTH: 24
<212> TYPE: DNA
<213> ORGANISM: artificial sequence
<220> FEATURE:
<223> OTHER INFORMATION: primer sequence

<400> SEQUENCE: 210
acttcttacc atctcctacc cacc                                           24

<210> SEQ ID NO 211
<211> LENGTH: 23
<212> TYPE: DNA
<213> ORGANISM: artificial sequence
<220> FEATURE:
<223> OTHER INFORMATION: primer sequence

<400> SEQUENCE: 211
gtcctcccat gacttcagct atc                                            23

<210> SEQ ID NO 212
<211> LENGTH: 23
<212> TYPE: DNA
<213> ORGANISM: artificial sequence
<220> FEATURE:
<223> OTHER INFORMATION: primer sequence

<400> SEQUENCE: 212
ggtttgaaat tgaagtgatg gct                                            23

<210> SEQ ID NO 213
<211> LENGTH: 22
<212> TYPE: DNA
<213> ORGANISM: artificial sequence
<220> FEATURE:
<223> OTHER INFORMATION: primer sequence

<400> SEQUENCE: 213
ttgctgcttg gagtttcttg ac                                             22

<210> SEQ ID NO 214
<211> LENGTH: 24
<212> TYPE: DNA
<213> ORGANISM: artificial sequence
<220> FEATURE:
<223> OTHER INFORMATION: primer sequence

<400> SEQUENCE: 214
agtccctact cactgatcct ctgc                                           24

<210> SEQ ID NO 215
<211> LENGTH: 24
<212> TYPE: DNA
<213> ORGANISM: artificial sequence
<220> FEATURE:
<223> OTHER INFORMATION: primer sequence

<400> SEQUENCE: 215
tgcccatctt agcactgata ctct                                           24
```

```
<210> SEQ ID NO 216
<211> LENGTH: 23
<212> TYPE: DNA
<213> ORGANISM: artificial sequence
<220> FEATURE:
<223> OTHER INFORMATION: primer sequence

<400> SEQUENCE: 216
acagttggac ggtggtagac att                                            23

<210> SEQ ID NO 217
<211> LENGTH: 22
<212> TYPE: DNA
<213> ORGANISM: artificial sequence
<220> FEATURE:
<223> OTHER INFORMATION: primer sequence

<400> SEQUENCE: 217
tcaagtggct tgttgctact gc                                             22

<210> SEQ ID NO 218
<211> LENGTH: 25
<212> TYPE: DNA
<213> ORGANISM: artificial sequence
<220> FEATURE:
<223> OTHER INFORMATION: primer sequence

<400> SEQUENCE: 218
tgtgcctaaa taagatggtt ctctg                                          25

<210> SEQ ID NO 219
<211> LENGTH: 21
<212> TYPE: DNA
<213> ORGANISM: artificial sequence
<220> FEATURE:
<223> OTHER INFORMATION: primer sequence

<400> SEQUENCE: 219
cacgagaatc gcttgaacct g                                              21

<210> SEQ ID NO 220
<211> LENGTH: 22
<212> TYPE: DNA
<213> ORGANISM: artificial sequence
<220> FEATURE:
<223> OTHER INFORMATION: primer sequence

<400> SEQUENCE: 220
gtagtgctag aggcctgcca gt                                             22

<210> SEQ ID NO 221
<211> LENGTH: 26
<212> TYPE: DNA
<213> ORGANISM: artificial sequence
<220> FEATURE:
<223> OTHER INFORMATION: primer sequence

<400> SEQUENCE: 221
taactgtgta tctttcccct catctt                                         26
```

SNP MARKERS ASSOCIATED WITH POLYCYSTIC OVARY SYNDROME

This application is a continuation-in-part of International Application PCT/CN2010/073387 filed May 31, 2010 and published in the English language, the disclosure of which is incorporated herein by reference in its entirety.

TECHNICAL FIELD

The present invention relates to SNP (Single Nucleotide Polymorphism) markers associated with Polycystic Ovary Syndrome (PCOS). The present invention further relates to probes, chips, primers and methods for detecting the SNPs. Also, the present invention relates to the use of SNPs in predicting and diagnosing the risk of PCOS.

BACKGROUND

PCOS is a clinical condition characterized by the presence of two or more of these features: chronic oligo-ovulation or anovulation, androgen excess and polycystic ovaries.[1] As the most common cause of anovulatory infertility, PCOS affects 6-8% childbearing-aged women.[2,3] Additionally, PCOS is associated with important endocrine-metabolic derangements and a broad range of adverse sequelae, including dyslipidemia, atherosclerosis, insulin resistance and type 2 diabetes.[4-6] Insulin resistance is present in perhaps 50% of women with PCOS.[7] Among women with impaired glucose tolerance (IGT) and diabetes mellitus, about 20% were recognized at younger age to have PCOS.[8-10]

The pathogenesis of PCOS is not fully understood. Heritable tendencies have long been recognized, but complex interactions exist between genetic and environmental factors. Association studies have been conducted on at least 70 candidate genes, principally related to reproductive hormones, insulin resistance, and chronic inflammation, e.g., follicle stimulating hormone receptor(FSHR), cytochrome P450, family 11A (CYP11A), insulin receptor (INSR) and interleukin 6 (IL-6)[11-15]; however, none correlates consistently with PCOS.[16]

SUMMARY

The present invention relates to SNPs associated with PCOS. Particularly, the present invention provides SNP markers associated with PCOS. Furthermore, the present invention provides probes, chips, primers and methods for detecting the SNPs. Also, the present invention relates to the use of them in predicting and diagnosing the risk of PCOS.

One aspect of the invention provides SNP markers, the nucleotide sequences of which are shown as: SEQ ID NO.1, wherein N is C or T; SEQ ID NO.2, wherein N is A or G; SEQ ID NO.3, wherein N is C or T; SEQ ID NO.4, wherein N is A or C; SEQ ID NO.5, wherein N is C or T; SEQ ID NO.6, wherein N is A or C; SEQ ID NO.7, wherein N is C or T; SEQ ID NO.8, wherein N is C or T; SEQ ID NO.9, wherein N is A or G; SEQ ID NO.10, wherein N is C or T; SEQ ID NO.11, wherein N is C or T; SEQ ID NO.12, wherein N is C or T; SEQ ID NO.13, wherein N is A or G; SEQ ID NO.14, wherein N is C or T; SEQ ID NO.15, wherein N is A or G; SEQ ID NO.16, wherein N is C or T; SEQ ID NO.17, wherein N is A or T; SEQ ID NO.18, wherein N is C or G; SEQ ID NO.19, wherein N is C or T; SEQ ID NO.20, wherein N is C or T; SEQ ID NO.21, wherein N is C or T; SEQ ID NO.22, wherein N is A or G; SEQ ID NO.23, wherein N is A or G; SEQ ID NO.24, wherein N is C or T; SEQ ID NO.25, wherein N is A or G; SEQ ID NO.26, wherein N is C or T; SEQ ID NO.27, wherein N is A or T; SEQ ID NO.28, wherein N is G or T; SEQ ID NO.29, wherein N is A or G; SEQ ID NO.30, wherein N is C or T; SEQ ID NO.31, wherein N is A or G; SEQ ID NO.32, wherein N is C or T; SEQ ID NO.33, wherein N is C or T; SEQ ID NO.34, wherein N is C or T; SEQ ID NO.35, wherein N is C or T; SEQ ID NO.36, wherein N is A or G; SEQ ID NO.37, wherein N is C or T; SEQ ID NO.38, wherein N is C or T; SEQ ID NO.39, wherein N is C or T; SEQ ID NO.40, wherein N is A or C; SEQ ID NO.41, wherein N is G or T; SEQ ID NO.42, wherein N is G or T; SEQ ID NO.43, wherein N is C or T; SEQ ID NO.44, wherein N is A or G; or SEQ ID NO.45, wherein N is C or T.

Another aspect of the invention provides probes for detecting the genotypes at the site N of the SNP markers of the present invention.

Still another aspect of the invention provides a chip for detecting the genotypes at the site N of the SNP markers of the present invention, wherein the chip comprises one or more probes of the present invention.

Still another aspect of the invention provides primers for determining the genotypes at the site N of the SNP markers of the present invention.

Still another aspect of the invention provides a kit comprising the probes, chip or primers of the present invention for detecting the genotypes at the site N of the SNP markers.

Still another aspect of the invention provides the use of the primers, probes, chip and kit of the present invention in the preparation of an agent for predicting or diagnosing PCOS.

Still another aspect of the invention provides the use of the primers, probes, chip and kit of the present invention in predicting or diagnosing PCOS.

Still another aspect of the invention provides a method of predicting or diagnosing PCOS based on the SNP markers, wherein the method comprises determining genotypes at the site N of the SNP markers of the present invention.

DETAILED DESCRIPTION

Figure 1:
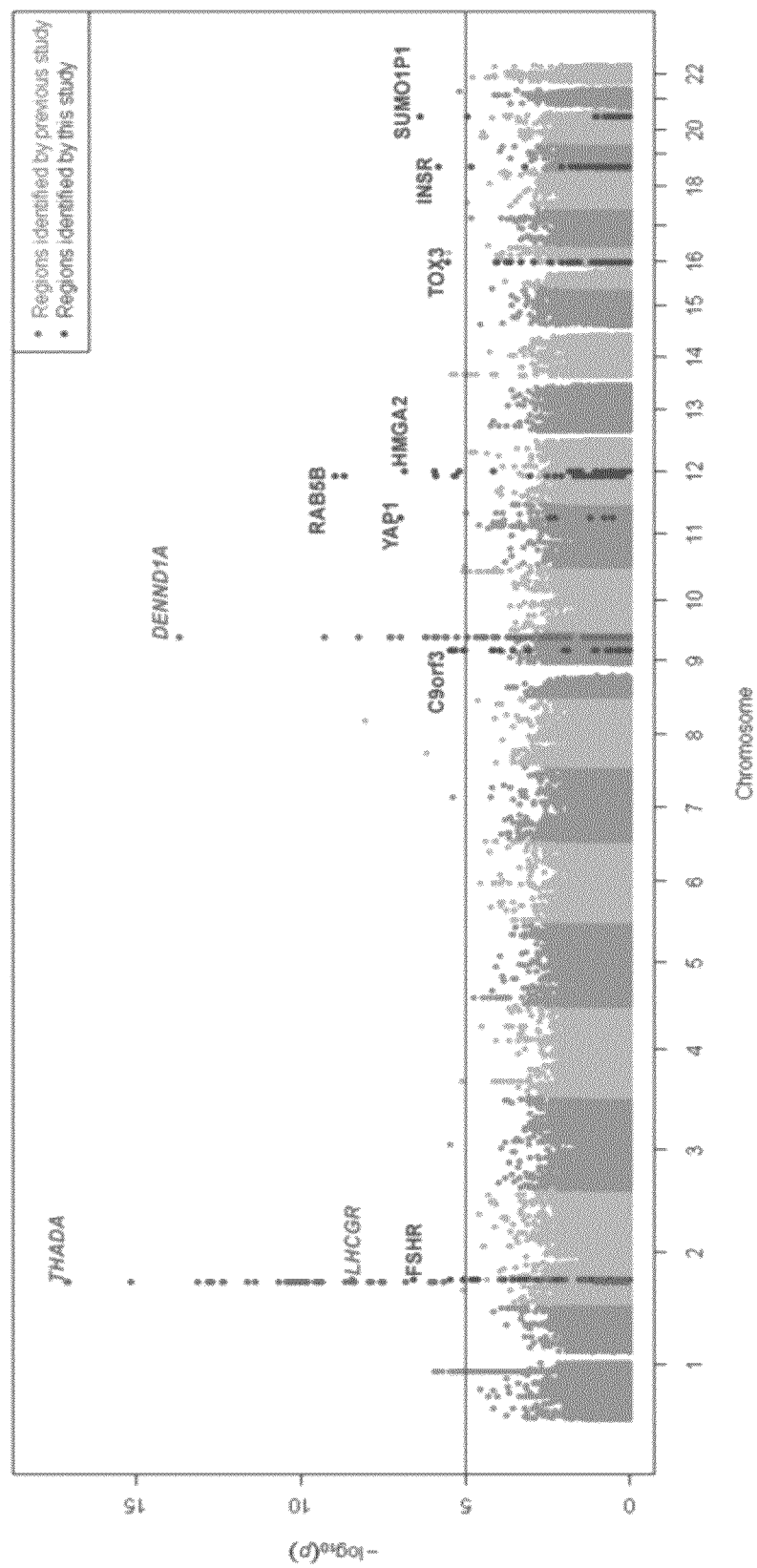
FIG. 1. Genome-wide Manhattan plots for the GWAS meta-analysis. Negative $\log_{10}$ P-values are shown for SNP markers that passed quality control. The solid horizontal line indicates a P value of $10^{-5}$. Markers within 50 kb of an SNP associated with PCOS are marked in red for those identified in a previous GWAS and replicated here, and in green for those first identified in the current study.
Figure 2A:
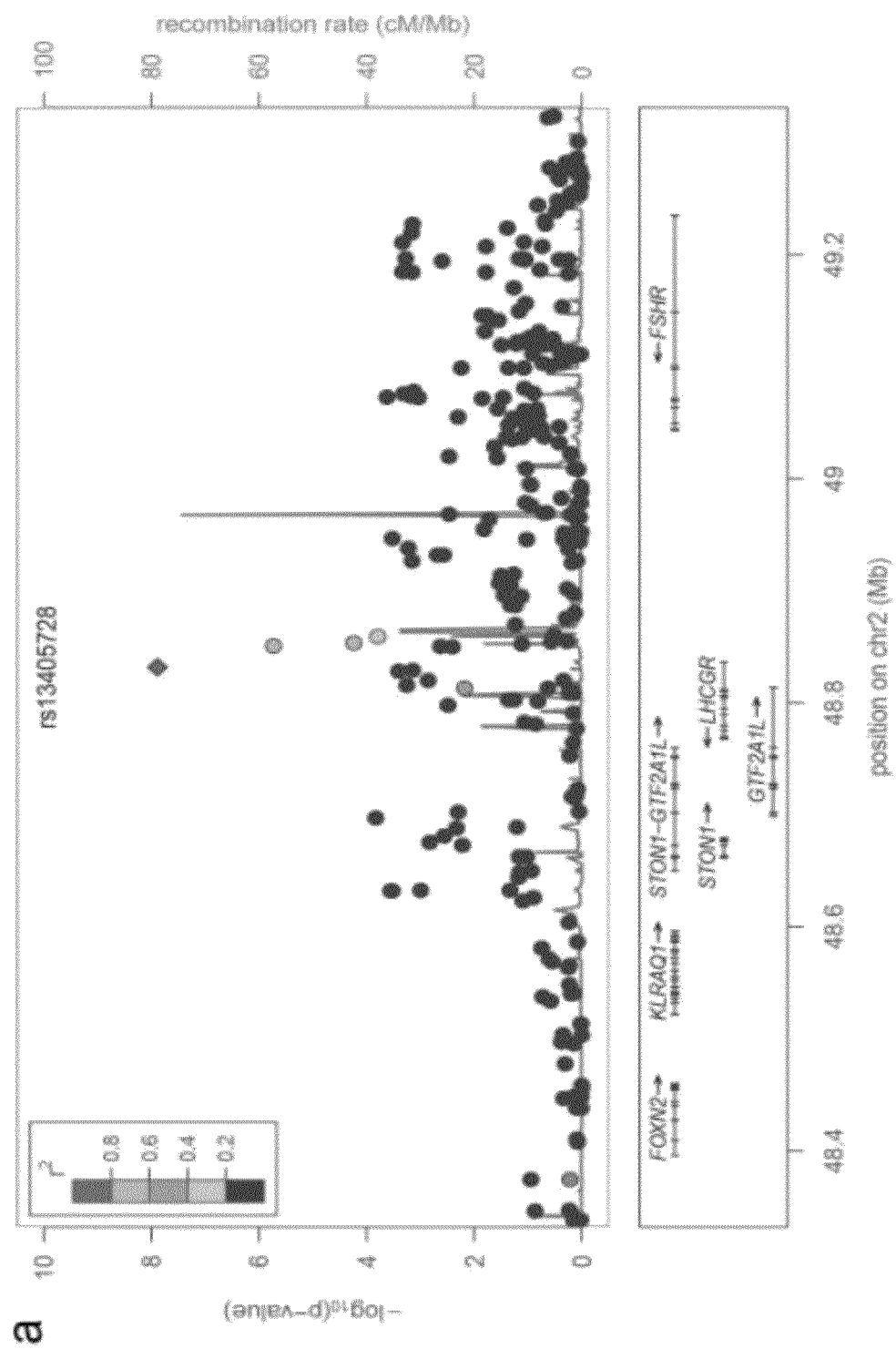
FIG. 2. Regional plots of the 3 PCOS loci from GWAS I (2p16.3, 2p21, and 9q33.3). (a-c) Genotyped SNPs passing quality control measures in GWAS are plotted with the P values (as $-\log_{10}$ values) as a function of genomic position (hg18) (a) 2p16.3, (b) 2p21, and (c) 9q33.3. In each panel, the index association SNP is represented by a diamond. Estimated recombination rates (taken from HapMap) are plotted to reflect the local LD structure. Gene annotations were taken from the University of California Santa Cruz genome browser. LD blocks were obtained from the Hapmap project (release 22, CHB+JPT).
Figure 2B:
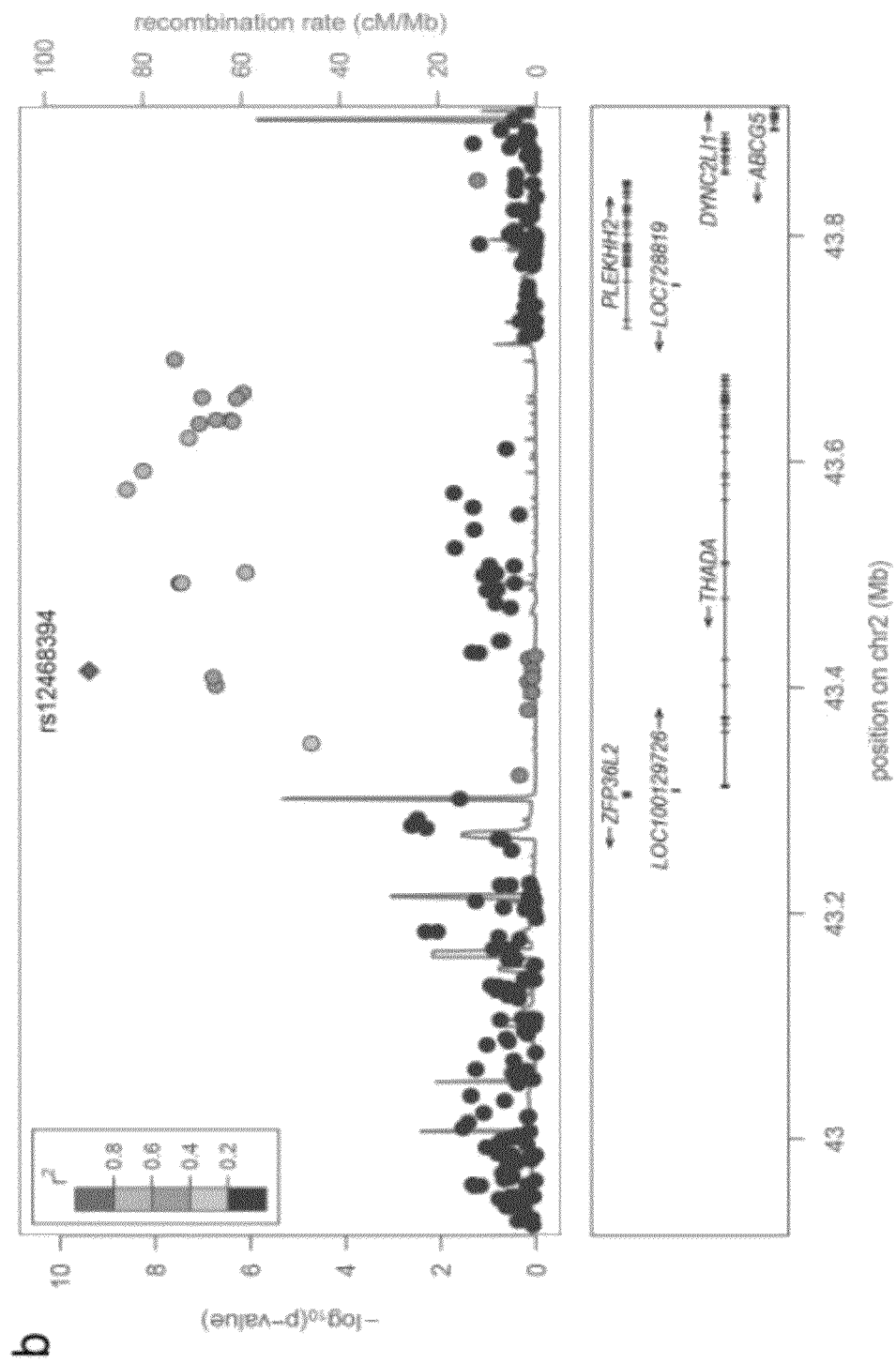
Figure 2C:
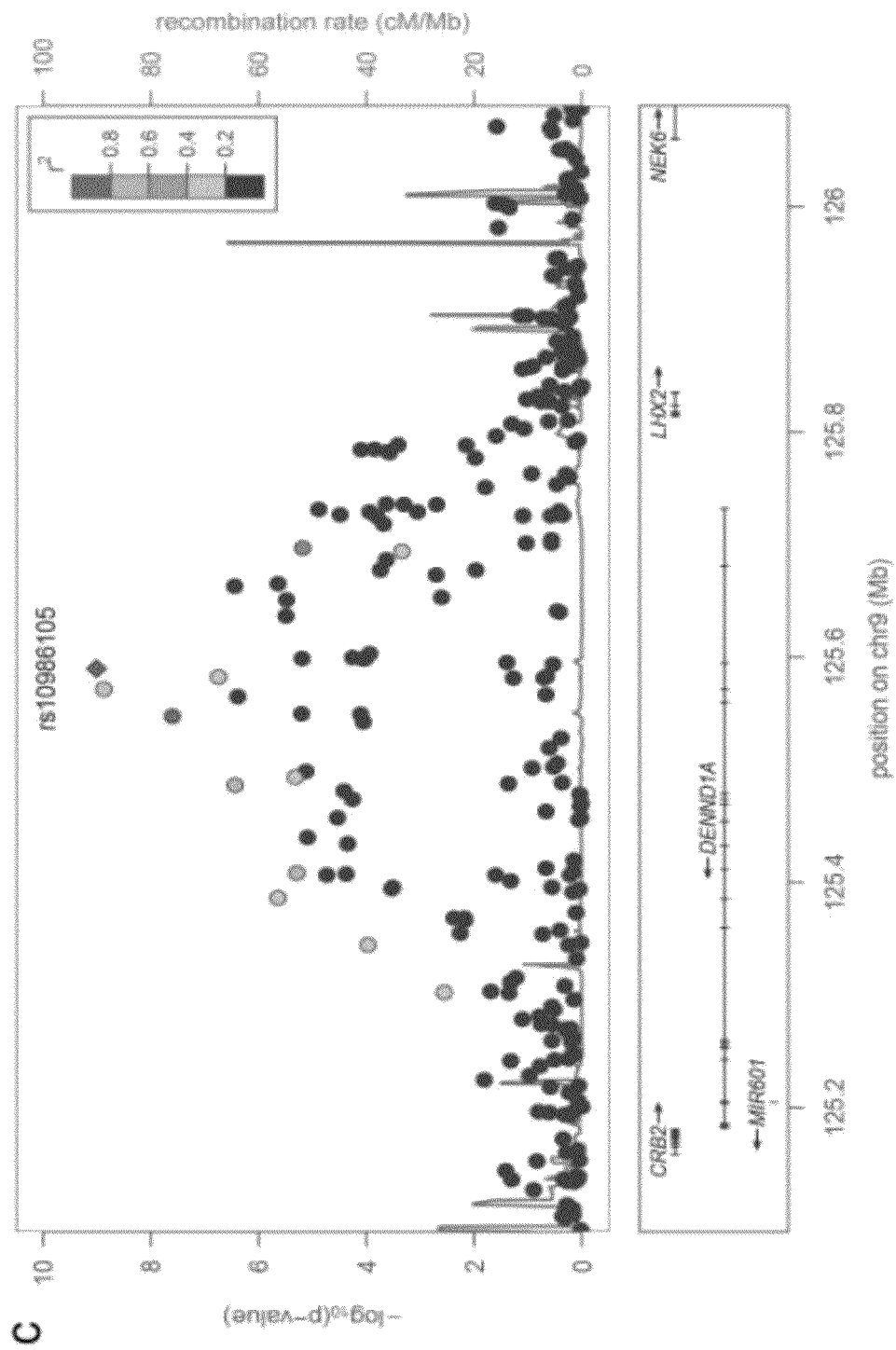
Figure 3A:
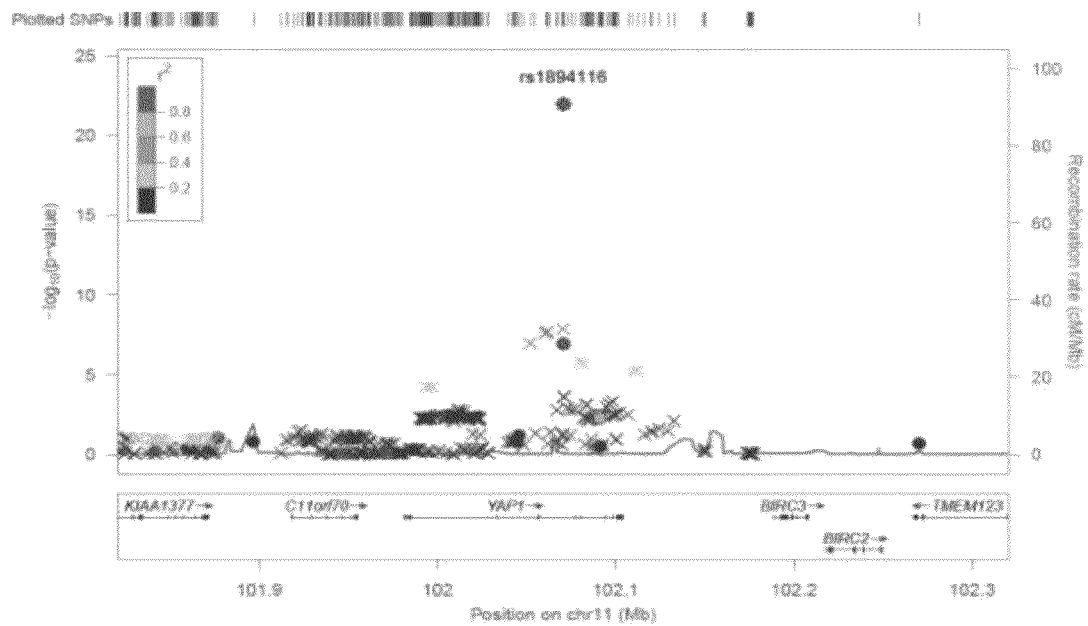
FIG. 3A-3H. Regional plots of the 8 newly discovered PCOS loci. Genotyped and imputed SNPs passing quality control are plotted with their meta-analysis P values (as $-\log_{10}$ values) as a function of genomic position (NCBI Build 37). In each panel, SNPs genotyped are plotted as circles, and SNPs imputed as crosses. The index association SNP is represented in purple, $P_{gwas\_meta}$ is for the combined results of the initial datasets, and $P_{GWAS-REP-Meta}$ is for the combined results of the initial and follow-up datasets, represented by the diamond (for the index SNP) or a square (for another independent SNP of this region). Estimated recombination rates (taken from 1000 Genome ASI) are plotted to reflect the local LD structure. Gene annotations were taken from the University of California Santa Cruz genome browser.
Figure 3B:
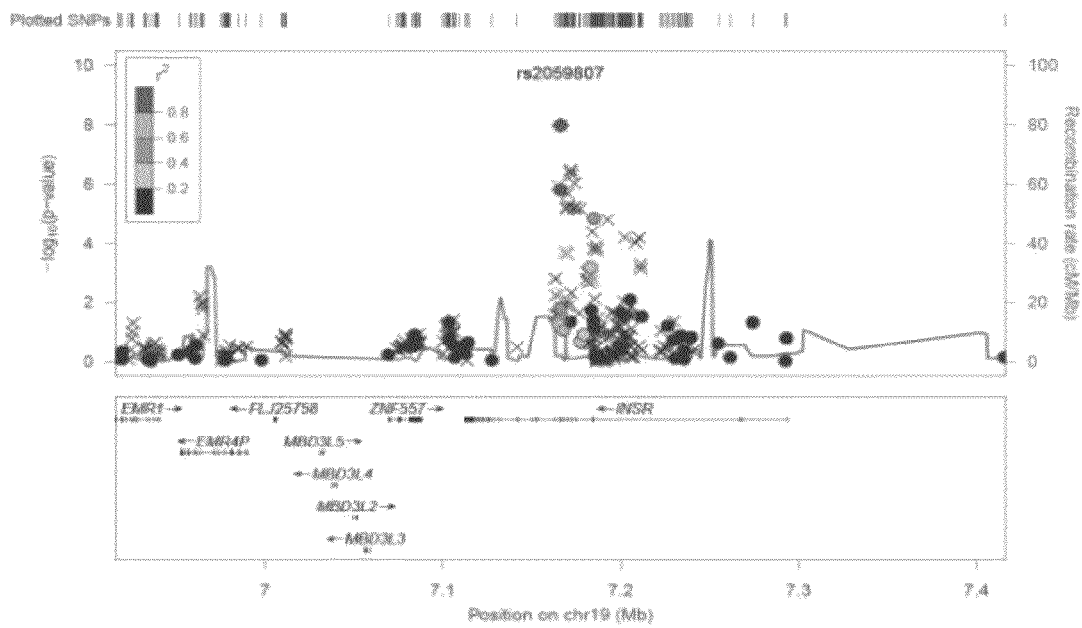
Figure 3C:
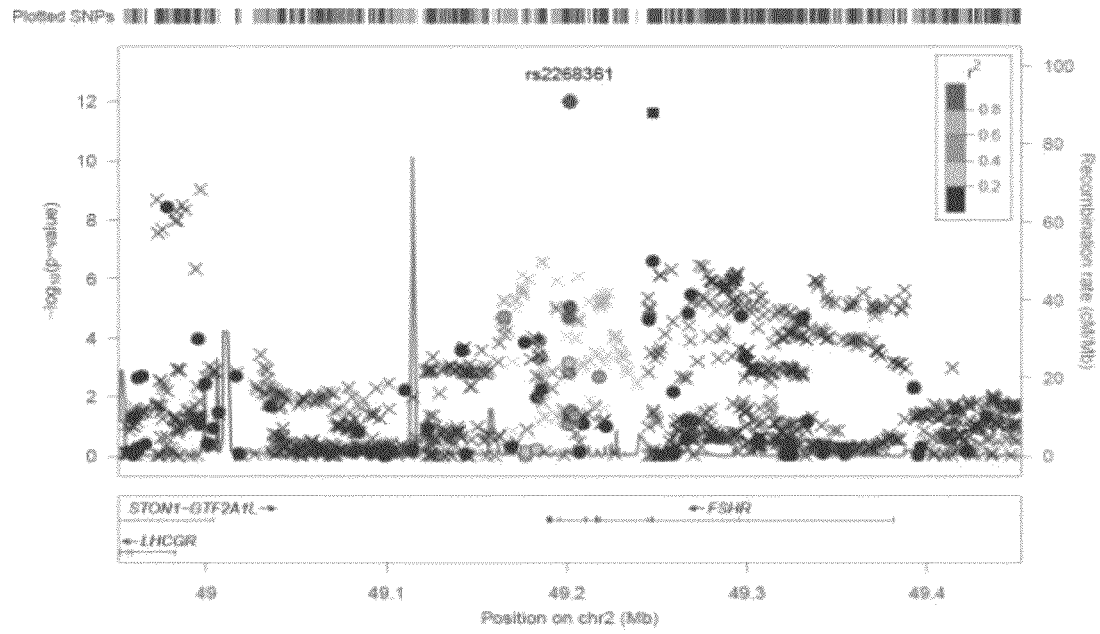
Figure 3D:
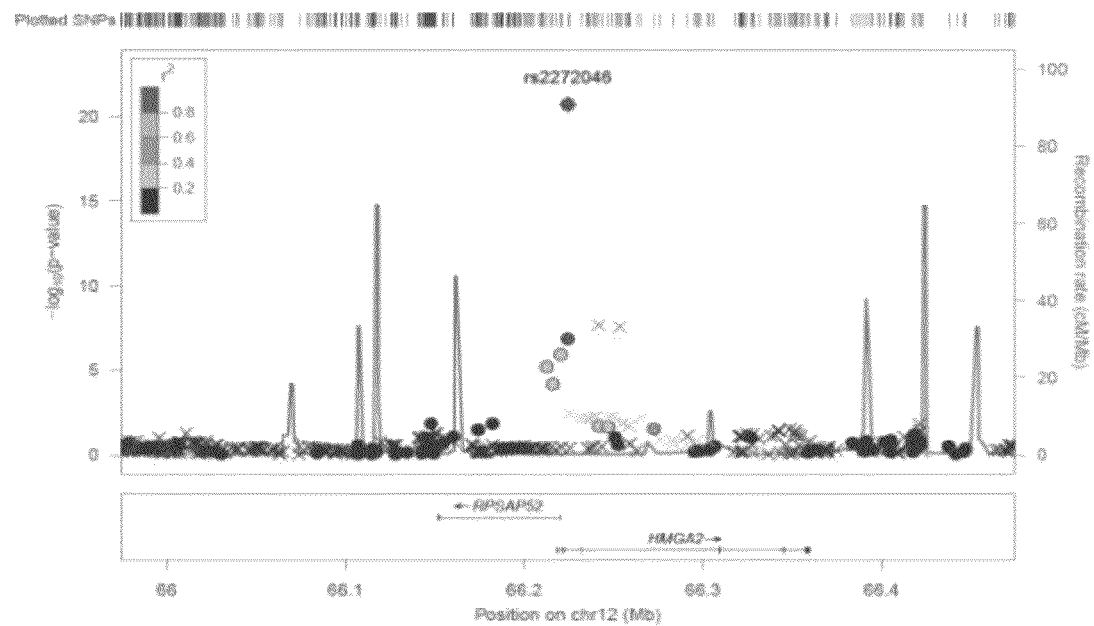
Figure 3E:
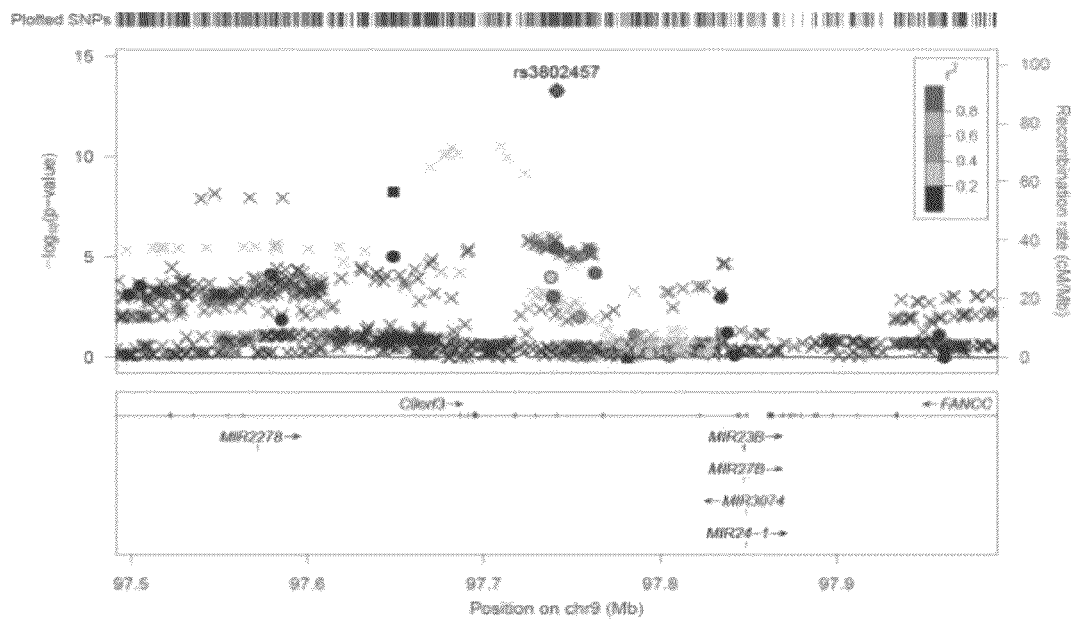
Figure 3F:
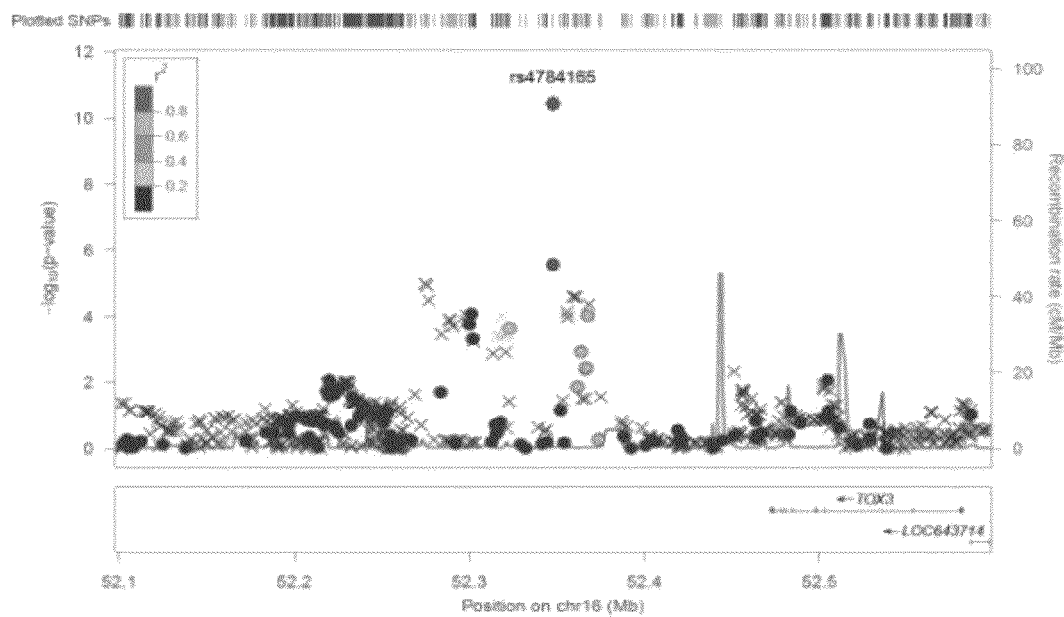
Figure 3G:
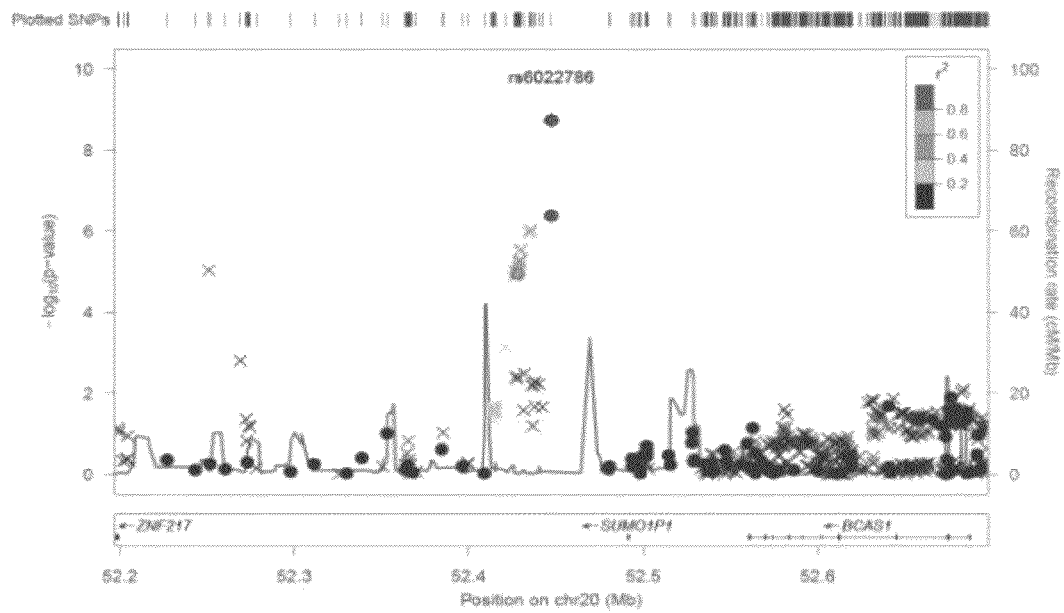
Figure 3H:
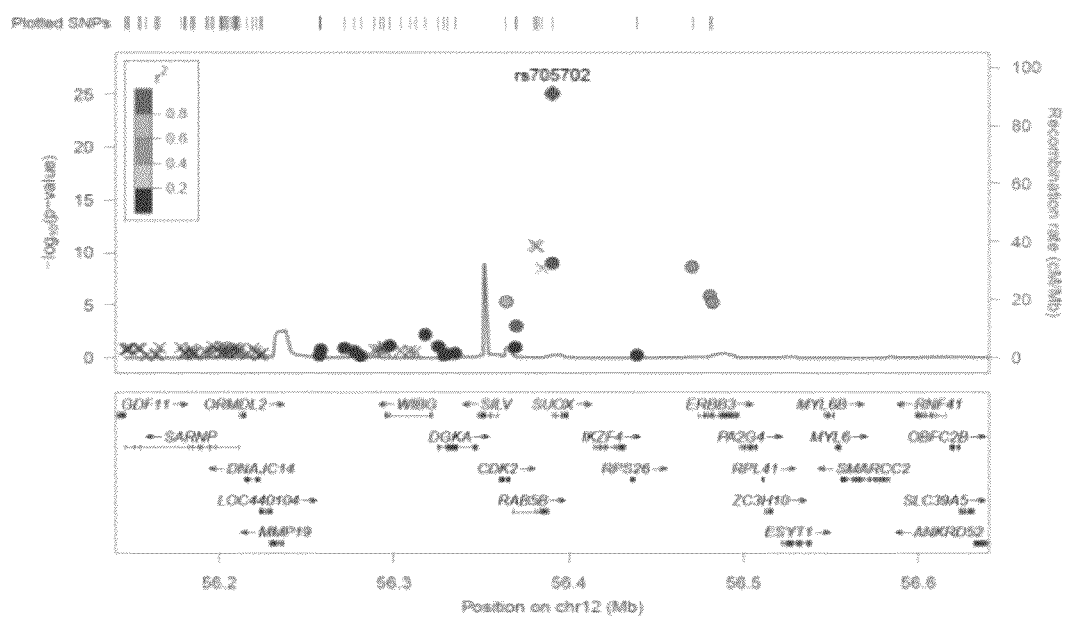

As used herein, the terms "single nucleotide polymorphism" or "SNP" is a DNA sequence variation or a genetic variant that occurs when a nucleotide, e.g., adenine (A), thymine (T), cytosine (C), or guanine (G), in the genome sequence is altered to another nucleotide.

SNPs are identified herein using the rs identifier numbers in accordance with the NCBI dbSNP database.

The term "genotype" refers to a description of the alleles of a gene or genes contained in an individual or a sample. As used herein, no distinction is made between the genotype of an individual and the genotype of a sample originating from the individual. The term "odd ratio" or "OR" refers to the ratio of the odds of the disease for individuals with the marker (polymorphism) relative to the odds of the disease in individuals without the marker (polymorphism).

In the first aspect, the invention provides SNP markers, the nucleotide sequences of which are shown as: SEQ ID NO.1, wherein N is C or T; SEQ ID NO.2, wherein N is A or G; SEQ ID NO.3, wherein N is C or T; SEQ ID NO.4, wherein N is A or C; SEQ ID NO.5, wherein N is C or T; SEQ ID NO.6, wherein N is A or C; SEQ ID NO.7, wherein N is C or T; SEQ ID NO.8, wherein N is C or T; SEQ ID NO.9, wherein N is A or G; SEQ ID NO.10, wherein N is C or T; SEQ ID NO.11, wherein N is C or T; SEQ ID NO.12, wherein N is C or T; SEQ ID NO.13, wherein N is A or G; SEQ ID NO.14, wherein N is C or T; SEQ ID NO.15, wherein N is A or G; SEQ ID NO.16, wherein N is C or T; SEQ ID NO.17, wherein N is A or T; SEQ ID NO.18, wherein N is C or G; SEQ ID NO.19, wherein N is C or T; SEQ ID NO.20, wherein N is C or T; SEQ ID NO.21, wherein N is C or T; SEQ ID NO.22, wherein N is A or G; SEQ ID NO.23, wherein N is A or G; SEQ ID NO.24, wherein N is C or T; SEQ ID NO.25, wherein N is A or G; SEQ ID NO.26, wherein N is C or T; SEQ ID NO.27, wherein N is A or T; SEQ ID NO.28, wherein N is G or T; SEQ ID NO.29, wherein N is A or G; SEQ ID NO.30, wherein N is C or T; SEQ ID NO.31, wherein N is A or G; SEQ ID NO.32, wherein N is C or T; SEQ ID NO.33, wherein N is C or T; SEQ ID NO.34, wherein N is C or T; SEQ ID NO.35, wherein N is C or T; SEQ ID NO.36, wherein N is A or G; SEQ ID NO.37, wherein N is C or T; SEQ ID NO.38, wherein N is C or T; SEQ ID NO.39, wherein N is C or T; SEQ ID NO.40, wherein N is A or C; SEQ ID NO.41, wherein N is G or T; SEQ ID NO.42, wherein N is G or T; SEQ ID NO.43, wherein N is C or T; SEQ ID NO.44, wherein N is A or G; or SEQ ID NO.45, wherein N is C or T.

One embodiment of this aspect provides more than one, for example, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44 or 45 SNP markers selected from the ones above.

In the present invention, each SNP marker refers to a SNP which is found to be associated with PCOS. As used herein, SNP marker and corresponding SNP relate to the same site in the nucleotide fragment. Especially when referring to the detection of the genotype at the site N of SNP marker, it should be understood that it implies the detection of the genotype at the corresponding site of the corresponding SNP, vice versa. The SNP for each SNP marker is listed in Table 1 below.

In another aspect, the invention provides probes for detecting the genotypes at the site N of one or more SNP markers of the present invention.

One embodiment of this aspect provides probes for each SNP marker listed in Table 1.

TABLE 1

SNP and Probes for each SNP marker

| SNP marker NO. | SNP marker SEQ ID NO. | SNP | Probes |
|---|---|---|---|
| 1 | 1 | rs11891936 | ATATAATTTTTTTAAC[A/G]GAGAAATTGCATAACA (SEQ ID NO. 46/SEQ ID NO. 47) |
| 2 | 2 | rs17030684 | TTCAAGTCCACAGATA[C/T]AGCTTITCATATGTGA (SEQ ID NO. 48/SEQ ID NO. 49) |
| 3 | 3 | rs4340576 | TCCCTGGGGGAGGTGTGACGGCAGAG[C/T]TGCATTTT TATGGTATGCCCCAACA (SEQ ID NO. 50/SEQ ID NO. 51) |
| 4 | 4 | rs12468394 | CTGTTGTAAAGCAAAATAGAATCCTA[A/C]ACCAGAA CTTCTGCAGTTAGCCACA (SEQ ID NO. 52/SEQ ID NO. 53) |
| 5 | 5 | rs7567607 | AAACTTTTACAACCAGAATTAATGTT[C/T]CCTTGTGC TCTTTTAAAAAATCAAA (SEQ ID NO. 54/SEQ ID NO. 55) |
| 6 | 6 | rs13429458 | GGGTATAGGTGTATGTAATCAGTTT[G/T]GTTTCATCT TCTAACTTTGCACAGCA (SEQ ID NO. 56/SEQ ID NO. 57) |
| 7 | 7 | rs7568365 | AGATGAAACAAAACTGATTACATACA[C/T]CTATACC CTGCCACTAATTAAAAAT (SEQ ID NO. 58/SEQ ID NO. 59) |
| 8 | 8 | rs7582497 | TCTTTGTTCAGAAGCACGGTACATTA[C/T]TATACAGC TGAAGCCCTCTAGCATT (SEQ ID NO. 60/SEQ ID NO. 61) |
| 9 | 9 | rs10176241 | GATCCTCCCTATATAAGGCCTAAAAC[A/G]CCACCATT AGAGTTTTACTGCTTTA (SEQ ID NO. 62/SEQ ID NO. 63) |

TABLE 1-continued

SNP and Probes for each SNP marker

| SNP marker NO. | SNP marker SEQ ID NO. | SNP | Probes |
|---|---|---|---|
| 10 | 10 | rs6744642 | AGGTATCCACACACACCCATTTCTTA[C/T]ACACACAT CCCATATCATTCTCGAT (SEQ ID NO. 64/SEQ ID NO. 65) |
| 11 | 11 | rs12478601 | AGTAAAGCCCGGGTCCTAACATTTTATTGA[A/G]TGGT ACTAACCAAGACCAGCAGGAATGAAA (SEQ ID NO. 66/ SEQ ID NO. 67) |
| 12 | 12 | rs1038822 | ACCTCTATAATTCCAGCTTCTTTTCTTCTT[G/A]GGTAG CTAAATCACCAAAAAAAAATTTTTG (SEQ ID NO. 68/ SEQ ID NO. 69) |
| 13 | 13 | rs7559891 | CTATGAACATTATTTTGCCTTGACACTTTT[T/C]ACATA GCACCCAAATCTTATGTATTTAATT (SEQ ID NO. 70/ SEQ ID NO. 71) |
| 14 | 14 | rs1873555 | CTCATTTCTAGGCAGAACTGAGTGTC[C/T]TTCCCTAA ACTGCCTGTATCCATTA (SEQ ID NO. 72/SEQ ID NO. 73) |
| 15 | 15 | rs7596052 | TGATGATGTGATGCAATACAAGTCTC[A/G]GAATTTGT TGGTGAGAGTGTAATTT (SEQ ID NO. 74/SEQ ID NO. 75) |
| 16 | 16 | rs10165527 | TCTTTTTCATGGCTGTTTCTACCATC[C/T]TGGAAATAA TAATTTTTAACTCTCT (SEQ ID NO. 76/SEQ ID NO. 77) |
| 17 | 17 | rs6726014 | TATATGTACTTATTCAACATAAATCC[A/T]CTGTTTAG AAAAAAGTATTATAGCT (SEQ ID NO. 78/SEQ ID NO. 79) |
| 18 | 18 | rs2374551 | TACCTTGTAAAAAATAATCCAGAAAG[C/G]AGTTCAA GATCAGCCTAGGCAATAT (SEQ ID NO. 80/SEQ ID NO. 81) |
| 19 | 19 | rs6731009 | TGTTCAGTATTATCAAGCTGTATATA[C/T]GTTTCGAC ATTTCATATACATGATC (SEQ ID NO. 82/SEQ ID NO. 83) |
| 20 | 20 | rs10179648 | AAACACAAACAATGAGATGCTATTGT[C/T]TTCCAATC AGCCTAGCAAAACCAGA (SEQ ID NO. 84/SEQ ID NO. 85) |
| 21 | 21 | rs7558302 | TAACTGCAACAACTCAGTGTGGATAC[C/T]ATCATCAT GTGAAAGTCACCCATGAC (SEQ ID NO. 86/SEQ ID NO. 87) |
| 22 | 22 | rs13405728 | TGCTCTGGCAGAAGAGGCACATGTTG[A/G]ACAAATG GCTGCATTATGGTGAGAT (SEQ ID NO. 88/SEQ ID NO. 89) |
| 23 | 23 | rs10818854 | ACACATCTTCTCCCCTATTATACTCA[A/G]CCAGCAAG CATTCCCACCTTTAAGC (SEQ ID NO. 90/SEQ ID NO. 91) |
| 24 | 24 | rs7857605 | TTATTGCCCTTATTTACTTCTCCAAACATT[A/G]ATCTG GTCTCATCGTTTGCAAAGGTGTTGC (SEQ ID NO. 92/ SEQ ID NO. 93) |
| 25 | 25 | rs2479106 | GGCAGAGATTCTGGGGACTGGAAAGA[A/G]CTAGTTA TGATCAAGGAACCAAAAG (SEQ ID NO. 94/SEQ ID NO. 95) |
| 26 | 26 | rs1778890 | TTTATTTTCTATAGCAGGTTTATTGA[C/T]ACTTTTTTT CTAGTAAAGTTTGAAA (SEQ ID NO. 96/SEQ ID NO. 97) |
| 27 | 27 | rs1627536 | TGCTGAAAAAAATGATTGGATGATAG[A/T]TCGGATT AAGAAGGGAAGAAATAGC (SEQ ID NO. 98/SEQ ID NO. 99) |
| 28 | 28 | rs10986105 | CTAAAAAGGAACAAAA[C/A]TATGTTGCATAACTCA (SEQ ID NO. 100/SEQ ID NO. 101) |
| 29 | 29 | rs2268361 | CTTTGATGCTGTGAGACGAAGGCATCTTGT[C/T]AGTG CCCTGGGATTGAGATCTTTCATTGGT (SEQ ID NO. 102/ SEQ ID NO. 103) |
| 30 | 30 | rs2349415 | AAAAACAGGTGTCAGGCTGGATTTGA[C/T]CCATTGG CTGTAGTTCAGTGACACT (SEQ ID NO. 104/SEQ ID NO. 105) |

TABLE 1-continued

SNP and Probes for each SNP marker

| SNP marker NO. | SNP marker SEQ ID NO. | SNP | Probes |
|---|---|---|---|
| 31 | 31 | rs10865238 | TCAATTCTGGAATTGGAAGGGAATCC[A/G]AGGAGAT CTATACCAGGCAATGCAT (SEQ ID NO. 106/SEQ ID NO. 107) |
| 32 | 32 | rs4744370 | CCCACCAAAGACAGTTTTGCTTGGGT[C/T]CTCTCAAA GCTATGCTGTTGGGTTT (SEQ ID NO. 108/SEQ ID NO. 109) |
| 33 | 33 | rs4385527 | GTGTGCTGTGTTGGGTGTGTGAACATTCCT[A/G]AGAC GTCCATAAGCTGATTTATAAAAACTT (SEQ ID NO. 110/SEQ ID NO. 111) |
| 34 | 34 | rs3802457 | CTCCAGGAAGCAGCCATGCCTGATGTGTGC[A/G]ATG AATATGCCTTATCCTCCCGAAACTGGC (SEQ ID NO. 112/SEQ ID NO. 113) |
| 35 | 35 | rs1894116 | GGATTGACCACTGTCAAGTCACAGAGTCAC[G/A]AAT TGTCTAGAATCAATATTATGTAGACTA (SEQ ID NO. 114/SEQ ID NO. 115) |
| 36 | 36 | rs2069408 | CATATGTAATGTGCATTTATCCCCCC[A/G]GTGCATTA CCTTACAATTGTCCGTA (SEQ ID NO. 116/SEQ ID NO. 117) |
| 37 | 37 | rs705702 | AGATAAACAGGGTAGTTGTAGTTGCAACAG[G/A]GTA GATAGAGGTAGGTCTACCCTGGGTTTA (SEQ ID NO. 118/SEQ ID NO. 119) |
| 38 | 38 | rs11171739 | CAAGGAAACCAAGGAAGATTTTTCTC[C/T]TTCAGAAC TCGGACCCTGAATACCA (SEQ ID NO. 120/SEQ ID NO. 121) |
| 39 | 39 | rs877636 | CTCAGGTCCCTGACTCAGCAGCCCACCAGG[G/A]CAG ACCATTCCAGTCTCCTGGAATCTAAAC (SEQ ID NO. 122/SEQ ID NO. 123) |
| 40 | 40 | rs2292239 | CAACAAATAGTGAAGAGACTTTTGAATCTA[T/G]AGG GCAGCACTTAAGGGATCTAGGGTGGCA (SEQ ID NO. 124/SEQ ID NO. 125) |
| 41 | 41 | rs2272046 | GGCCTTGGGACATTTG[C/A]AAACAAAGCTGTTGAT (SEQ ID NO. 126/SEQ ID NO. 127) |
| 42 | 42 | rs4784165 | GTTATTTTCCCTATTAAAGAACATCC[G/T]CTCATAGT TTTTCAAGTTATTATGT (SEQ ID NO. 128/SEQ ID NO. 129) |
| 43 | 43 | rs2059807 | GCATTTTATACAACCTCACTGCATCAGCCT[G/A]TTAA AAGCAAGAGGTCTGATTCACATACGA (SEQ ID NO. 130/SEQ ID NO. 131) |
| 44 | 44 | rs6022786 | ATTCGTTGACTATTTTAGCTGGTGAC[A/G]CAATGAAA AAACAGAGTCTAAGCAA (SEQ ID NO. 132/SEQ ID NO. 133) |
| 45 | 45 | rs11225161 | AGGCCTGCCAGTTTTAGGGGCCATTTGGCT[C/T]CTGA GAAGAACTGTTAATAAAAGTATTAAT (SEQ ID NO. 134/SEQ ID NO. 135) |

In still another aspect, the invention provides a chip for detecting the genotypes at the site N of one or more SNP markers of the present invention, wherein the chip comprises the probes of the present invention.

In one embodiment of this aspect, the chip is used to detect the genotypes at the site N of 45 SNP markers of the present invention. More preferably, the chip comprises the probes shown as SEQ ID NO. 46-135.

In another embodiment of this aspect, the chip is used to detect the genotypes at the site N of SNP markers shown as SEQ ID NO. 6, 11, 22, 23, 25, 29, 30, 33, 34, 35, 37, 41, 42, 43 and 44. More preferably, the chip comprises the probes shown as SEQ ID NO. 56, 57, 66, 67, 88, 89, 90, 91, 94, 95, 102, 103, 104, 105, 110, 111, 112, 113, 114, 115, 118, 119, 126, 127, 128, 129, 130, 131, 132 and 133.

In still another aspect, the invention provides primers for detecting the genotypes at the site N of one or more SNP markers of the present invention.

In one embodiment of this aspect, the primers for each SNP marker are listed in Table 2.

TABLE 2

Primers for 45 SNP markers

| SNP marker NO. | Primer Sequence (5'-3') | Product length (i.e. SNP marker length) |
|---|---|---|
| 1 | CGGGTTCAAGTGGTTCTGCT (forward) (SEQ ID NO. 136)<br>GTTGTTGTTGTTCCTATGGTTTCC (reverse) (SEQ ID NO. 137) | 452 bp |
| 2 | AGATAACAACTCTATGCTCTGGCTTC (forward) (SEQ ID NO. 138)<br>AAGGCCCTTCAGTGCTGTTCT (reverse) (SEQ ID NO. 139) | 445 bp |
| 3 | ATCTGCCATTCCGATTTCCA (forward) (SEQ ID NO. 140)<br>CAAGAAAGGCAGGATGGATGTT (reverse) (SEQ ID NO. 141) | 318 bp |
| 4 | TCTGCCTGGGAAGTGTAAGTCTC (forward) (SEQ ID NO. 142)<br>ATACTCCAGTCACTTTCCTGTCTCC (reverse) (SEQ ID NO. 143) | 328 bp |
| 5 | TCTGTCTTGCTTTCTTAGCCTCC (forward) (SEQ ID NO. 144)<br>TGTGCTATTGTTGTTCACTTCTATGG (reverse) (SEQ ID NO. 145) | 401 bp |
| 6 | CAGCGGTATGATTTCGTAGTG (forward) (SEQ ID NO. 146)<br>GCTAAAATCTCATCACCTGGAC (reverse) (SEQ ID NO. 147) | 560 bp |
| 7 | CAGCGGTATGATTTCGTAGTG (forward) (SEQ ID NO. 146)<br>GCTAAAATCTCATCACCTGGAC (reverse) (SEQ ID NO. 147) | 560 bp |
| 8 | CAGCGGTATGATTTCGTAGTG (forward) (SEQ ID NO. 146)<br>GCTAAAATCTCATCACCTGGAC (reverse) (SEQ ID NO. 147) | 560 bp |
| 9 | AAGTAGCTGCCCAAACAATGTG (forward) (SEQ ID NO. 148)<br>CAGGCTTGGGACCAGATTGT (reverse) (SEQ ID NO. 149) | 266 bp |
| 10 | TAAACCAAGCTCCAATTTCTCATAG (forward) (SEQ ID NO. 150)<br>CACACCTTTACTACTGTTTCCTATGC (reverse) (SEQ ID NO. 151) | 342 bp |
| 11 | AGACTCAGATGAGATGCCACAT (forward) (SEQ ID NO. 152)<br>TTACCTGTCCAACTCCAGAATG (reverse) (SEQ ID NO. 153) | 465 bp |
| 12 | AGGCTGAAGCAGGAGAATCG (forward) (SEQ ID NO. 154)<br>GGAGACGACCTTAGACTGTAGCAT (reverse) (SEQ ID NO. 155) | 321 bp |
| 13 | TCATCGCTCATTCAGTCATCAGTT (forward) (SEQ ID NO. 156)<br>GCCAACATCTTTGCTGAGGAAT (reverse) (SEQ ID NO. 157) | 553 bp |
| 14 | ATTAATATGGCCAACTCAAATGAACT (forward) (SEQ ID NO. 158)<br>GCTGGAGAAGGGTAGAGGTGC (reverse) (SEQ ID NO. 159) | 460 bp |
| 15 | AAAGGACATCGACAGGCATTG (forward) (SEQ ID NO. 160)<br>GCATCCGTAATCCAACACCTG (reverse) (SEQ ID NO. 161) | 542 bp |
| 16 | CCTATTCACCTCAATTGCAGTCC (forward) (SEQ ID NO. 162)<br>CTTCCCAAATAGCCAGTTCCA (reverse) (SEQ ID NO. 163) | 426 bp |
| 17 | GGTTTTGGAACTGGCTATTTGG (forward) (SEQ ID NO. 164)<br>CCGTCATCCTTGTCTGCCTACT (reverse) (SEQ ID NO. 165) | 521 bp |
| 18 | CCATGAGCCATTATTGTAAACTGAT (forward) (SEQ ID NO. 166)<br>TAGCTGGGACTGTAGGTGTGT (reverse) (SEQ ID NO. 167) | 297 bp |
| 19 | TTAGAAATGCTGGTGGTTGTACAA (forward) (SEQ ID NO. 168)<br>CTAATGTGATCCTCAAATGGCTACT (reverse) (SEQ ID NO. 169) | 382 bp |
| 20 | AACCCAGGCAAAAAGAGAAATAG (forward) (SEQ ID NO. 170)<br>ACTGACTCTGGTTTTGCTAGGCT (reverse) (SEQ ID NO. 171) | 446 bp |
| 21 | CCAAGTGTCACCTCTGCCATC (forward) (SEQ ID NO. 172)<br>CCACTGTTGCAAATTCATTCCA (reverse) (SEQ ID NO. 173) | 434 bp |
| 22 | GTGGTTCTTACTCTAGCACAATGAT (forward) (SEQ ID NO. 174)<br>CCATCCACATACTCACTTCAATATC (reverse) (SEQ ID NO. 175) | 341 bp |
| 23 | CAAAACCAGGCTGATGACAAT (forward) (SEQ ID NO. 176)<br>GTTTGAGAATCATAGACCAGCAC (reverse) (SEQ ID NO. 177) | 842 bp |
| 24 | CTCCAGGGACTGCCTCTTTCT (forward) (SEQ ID NO. 178)<br>TGTTTATGCATGTAACTGTAGGTGG (reverse) (SEQ ID NO. 179) | 472 bp |
| 25 | GAGCAGCCACTCAAGAAACAG (forward) (SEQ ID NO. 180)<br>AAGCCACCATCCAGTCTCAC (reverse) (SEQ ID NO. 181) | 429 bp |

TABLE 2-continued

Primers for 45 SNP markers

| SNP marker NO. | Primer Sequence (5'-3') | Product length (i.e. SNP marker length) |
|---|---|---|
| 26 | AAACAAGATAGGGCTAGGCTGATT(forward) (SEQ ID NO. 182)<br>CATGATTGACTGCCTGGTACTCC(reverse) (SEQ ID NO. 183) | 648 bp |
| 27 | AGAGGCTATTCTCAGTGAGCTTCTC (forward) (SEQ ID NO. 184)<br>GCACAGTGCATGGCAATAGTAAG(reverse) (SEQ ID NO. 185) | 273 bp |
| 28 | AGCATACCTCAAGCATGAACAGAT (forward) (SEQ ID NO. 186)<br>AAGCAATGTAGAAACATGGCACA(reverse) (SEQ ID NO. 187) | 255 bp |
| 29 | GCTCCCTCCTTCAACATCCAC (forward) (SEQ ID NO. 188)<br>GCAATGCCAACAAGAAGACAGA(reverse) (SEQ ID NO. 189) | 304 bp |
| 30 | CTGTGGCTCACCTTGGAGATTAT (forward) (SEQ ID NO. 190)<br>TGGCTTTCTGTTCCTACGTTAGAC(reverse) (SEQ ID NO. 191) | 481 bp |
| 31 | TGTTATTTGATTGATGGTCCTAGAGG (forward) (SEQ ID NO. 192)<br>CTTTAGGCTACTATCATTGCACCATT(reverse) (SEQ ID NO. 193) | 300 bp |
| 32 | AATCCTGTCCGTTTCCAACACT (forward) (SEQ ID NO. 194)<br>GCACAAACCCAACAGCATAGC(reverse) (SEQ ID NO. 195) | 186 bp |
| 33 | ATCACAAGTTTGCCTTCTTAAATATG (forward) (SEQ ID NO. 196)<br>GTGCCAGAAGATCGCAGAGTT(reverse) (SEQ ID NO. 197) | 560 bp |
| 34 | CCTCTTCACCCACAGCAACAT (forward) (SEQ ID NO. 198)<br>AGACAGTGGAAGTGGTCCTCATT(reverse) (SEQ ID NO. 199) | 323 bp |
| 35 | TTTTCTGTTGTATGGGATGAATGG (forward) (SEQ ID NO. 200)<br>TACAAGGATTGACCACTGTCAAGTC(reverse) (SEQ ID NO. 201) | 427 bp |
| 36 | TGCAGTAGGCTGTCTTCAAATCA (forward) (SEQ ID NO. 202)<br>ACCTTGTGATGCAGCCACTTC(reverse) (SEQ ID NO. 203) | 284 bp |
| 37 | CGAGACAGGCAGGTTGCTAAG (forward) (SEQ ID NO. 204)<br>AAAGACGGCTATTCAGTGTTGTTG(reverse) (SEQ ID NO. 205) | 488 bp |
| 38 | CAGGCTGAGGCAGGAGAATC (forward) (SEQ ID NO. 206)<br>TGGCCTTACTTAGGATTTCTTACTG (reverse) (SEQ ID NO. 207) | 418 bp |
| 39 | GAGCCACTACGCCTGTCTGATT (forward) (SEQ ID NO. 208)<br>CGAGATGCTGAGATAGTGGTGAAG(reverse) (SEQ ID NO. 209) | 392 bp |
| 40 | ACTTCTTACCATCTCCTACCCACC (forward) (SEQ ID NO. 210)<br>GTCCTCCCATGACTTCAGCTATC(reverse) (SEQ ID N0,211) | 360 bp |
| 41 | GGTTTGAAATTGAAGTGATGGCT (forward) (SEQ ID NO. 212)<br>TTGCTGCTTGGAGTTTCTTGAC(reverse) (SEQ ID NO. 213) | 180 bp |
| 42 | AGTCCCTACTCACTGATCCTCTGC (forward) (SEQ ID NO. 214)<br>TGCCCATCTTAGCACTGATACTCT(reverse) (SEQ ID NO. 215) | 202 bp |
| 43 | ACAGTTGGACGGTGGTAGACATT (forward) (SEQ ID NO. 216)<br>TCAAGTGGCTTGTTGCTACTGC(reverse) (SEQ ID NO. 217) | 848 bp |
| 44 | TGTGCCTAAATAAGATGGTTCTCTG (forward) (SEQ ID NO. 218)<br>CACGAGAATCGCTTGAACCTG(reverse) (SEQ ID NO. 219) | 314 bp |
| 45 | GTAGTGCTAGAGGCCTGCCAGT (forward) (SEQ ID NO. 220)<br>TAACTGTGTATCTTTCCCCTCATCTT (reverse) (SEQ ID NO. 221) | 527 bp |

In still another aspect, the invention provides a kit for detecting the genotypes at the site N of one or more SNP markers of the present invention, wherein the kit comprises the probes, chip or the primers of the present invention.

In one embodiment of this aspect, the kit is used to detect the genotypes at the site N of at least 15 SNP markers of the present invention. Preferably, the kit is used to detect the genotypes at the site N of 45 SNPs of the present invention. More preferably, the kit comprises probes shown as SEQ ID NO. 46-135.

In another embodiment of this aspect, the kit is used to detect the genotypes at the site N of 15 SNP markers shown as SEQ ID NO. 6, 11, 22, 23, 25, 29, 30, 33, 34, 35, 37, 41, 42, 43 and 44. More preferably, the kit comprises the probes consisted of probes shown as SEQ ID NO. 56, 57, 66, 67, 88, 89, 90, 91, 94, 95, 102, 103, 104, 105, 110, 111, 112, 113, 114, 115, 118, 119, 126, 127, 128, 129, 130, 131, 132 and 133.

In another embodiment of this aspect, the kit comprises primers for detecting the genotypes at the site N of 45 SNP markers of the present invention. More preferably, the kit comprises primers consisted of the primers shown as SEQ ID NO. 136-221.

In still another embodiment of this aspect, the kit comprises primers for determining the genotypes at the site N of 15 SNP markers of the present invention, wherein the 15 SNP markers are shown as SEQ ID NO. 6, 11, 22, 23, 25, 29, 30, 33, 34, 35, 37, 41, 42, 43 and 44. Preferably, the kit comprises primers consisted of the primers shown as SEQ ID NO.146, 147, 152, 153, 174, 175, 176, 177, 180, 181, 188, 189, 190, 191, 196, 197, 198, 199, 200, 201, 204, 205, 212, 213, 214, 215, 216, 217, 218 and 219.

In still another aspect, the invention provides the use of the primers, probes, chip or kit of the present invention in the preparation of an agent for predicting or diagnosing PCOS, wherein the primers, probes, chip or kit is used to detect the genotypes at the site N of the SNP markers of the present invention. In one embodiment, the genotypes at the site N of at least 15 SNP markers, preferably all 45 SNP markers of the present invention are detected. In another embodiment, the genotypes at the site N of 15 SNP markers are detected, wherein the 15 SNPs are shown as SEQ ID NO. 6, 11, 22, 23, 25, 29, 30, 33, 34, 35, 37, 41, 42, 43 and 44.

In still another aspect, the invention provides the use of the primers, probes, chip or kit of the present invention in predicting or diagnosing PCOS, wherein the primers, probes, chip or kit is used to detect the genotypes at the site N of the SNP markers of the present invention.

Still another aspect of the invention provides a method of predicting or diagnosing PCOS, wherein the method comprises determining genotypes at the site N of one or more SNP markers of the present invention.

In one embodiment of this aspect, the method comprises determining genotypes at the site N of at least 15 SNP markers, preferably all 45 SNP markers of the present invention.

In another embodiment of this aspect, the method comprises determining genotypes at the site N of 15 SNP markers, wherein the 15 SNP markers are shown as SEQ ID NO. 6, 11, 22, 23, 25, 29, 30, 33, 34, 35, 37, 41, 42, 43 and 44.

In yet another embodiment of this aspect, determining genotypes at the site N of the SNP markers is performed by hybridization, for example, using the probes or chips of the present invention.

In yet another embodiment of this aspect, determining genotypes at the site N of the SNP markers is performed by sequencing, for example, PCR, Real-time Quantitative PCR, or MassARRAY (Sequenom), using primers of the present invention.

In yet another embodiment of this aspect, the present method comprises the following steps: extracting DNA from peripheral blood or saliva of a subject, determining genotypes at the site N of one or more SNP markers, and analyzing the results to predict the risk of PCOS or diagnose PCOS.

Embodiments

Subjects

All Han Chinese samples evaluated were obtained in multiple collaborating hospitals from China. The discovery sets (GWAS I and II) of 2254 Han Chinese PCOS samples and 3001 controls were recruited mainly from northern China. Subsequent replication samples (REP I and II) of 8226 cases and 7578 controls were collected from 29 provinces (Shandong, Heilongjiang, Jilin, Liaoning, Inner Mongolia, Hebei, Henan, Tianjin, Beijing, Shanxi, Shaanxi, Gansu, Ningxia, Jiangsu, Anhui, Shanghai, Guangdong, Guangxi, Fujian, Zhejiang, Hubei, Hunan, Jiangxi, Sichuan, Chongqing, Xinjiang, Yunnan, Guizhou and Hainan) throughout China. The PCOS patients were diagnosed according to the Rotterdam Consensus proposed in 200345. Clinical data of the patients were obtained from medical records. Oligo-/aovulation was assessed by menstrual cycles more than 35 days in length or a history of ≤8 menstrual cycles in a year. Polycystic ovarian morphology was determined when ≥12 follicles measuring 2-9 mm in diameter were scanned in either ovary or the ovarian volume was above 10 ml. Hyperandrogenism was confirmed if there were evidences about hyperandrogenemia and/or hirsutism. Patients with other causes of oligomenorrhea or hyperandrogenism were excluded. Clinical information was collected from the cases through a full clinical checkup by physician specialists. Additional demographic information was collected from both cases and controls through a structured questionnaire. All participants provided written informed consents. The study was approved by the Institutional Ethical Committee of each hospital and was conducted according to Declaration of Helsinki principles.

DNA Extraction

EDTA anti-coagulated venous blood samples were collected from all participants. Genomic DNA was extracted from peripheral blood lymphocytes by standard procedures using Flexi Gene DNA kits (Qiagen), and was diluted to working concentrations of 50 ng/μL for genome-wide genotyping and 15-20 ng/μL for the validation study.

GWAS Genotyping and Quality Control

Affymetrix Genome-Wide Arrays were used for discovery phase: GWAS Data Set 1 was performed using the Affymetrix Genome-Wide Human SNP Array 6.0, and Samples of GWAS Data Set 2 were genotyped using Axiom Genome-Wide Arrays. Quality control filtering of the GWAS data was performed as follows: for the SNP 6.0 arrays whose Contrast QC was 0.4 or greater being left out of further data analysis, and for the Axiom arrays, a Dish QC (DQC) of 0.82 or better is considered a pass. Genotype data were generated using the birdseed algorithm for SNP 6.0, and the Axiom GT1 algorithm for Axiom arrays. For sample filtering, array with generated genotypes of fewer than 95% of loci were excluded. For SNP filtering (after sample filtering), SNP with call rates <95% in either case or control samples were removed. SNPs whose MAF (minor allele frequency) was <1%, or deviated significantly from Hardy Weinberg Equilibrium (HWE, P≤1E-5) in controls were excluded.

Imputation Analysis of Untyped SNPs

To conduct meta-analysis across array types, imputations were conducted for both GWAS date sets using MACH[17,18], separately. Phased haplotypes for 90 CHB+JPT subjects (180 haplotypes) were used as the reference for imputing genotypes. Any SNP imputed with information content $r^2<0.3$ was excluded from association analysis because of lack of power. In addition, a second imputation step was performed using IMPUTEv2[19,20] for the 8 new identified regions (0.5 MB either side of any SNP achieved a $P_{GWAS-META}<10^{-5}$), using the 1,000 Genomes haplotypes Phase I interim release (June 2011) as reference. Any SNPs imputed with proper info <0.4 were treated as poor imputation. The criteria for SNP QC filtering were the same as the genotyped ones.

Analysis of Population Substructure

Population substructure was evaluated using principal components analysis (PCA) as implemented in the software EIGENSTRAT[21]. Twenty principal components (PCs) were generated for each subject. PCA were conducted twice, and the first one was for the analysis of study data (1,510 cases and 2,106 controls) combined with HapMap data. The first two principal components were plotted, and, 43 cases and 9 controls were excluded. The second one was conducted for the remaining test samples. The PCs were generated for association analysis.

Association Analysis

Logistic regression was used to determine whether there was a significant difference in PC scores between cases and controls; significant PCs were used as covariates in the association analysis to correct for population stratification. After adjustment, little stratification was observed ($\lambda$=1.07, $\lambda_{1000}$=1.04, standardized to a sample size of 1000[22]).

Meta-Analysis of GWAS Data Sets

The GWAS data sets were combined using meta-analysis. The meta-analysis was conducted using PLINK[23]. The heterogeneity across the three stages was evaluated using Q-statistic P-value. The Mantel-Haenszel method is used to calculate the fixed effect estimate.

SNP Selection and Replication

The following criteria were used for the selection of SNPs for validation: Strong significant SNPs ($P_{GWAS-META} \leq 10^{-5}$) from the GWAS-meta analysis were selected for Replication I. Generally, those SNPs showed nominal significance (P<0.05) in Replication I or were not significant in Replication I but with a GWAS-REP1 meta-analysis P value less than $5 \times 10^{-6}$ were also kept for Replication II. The Sequenom MassARRAY system was used for most of the replication studies, except for rs2059807, which was genotyped using TaqMan assays (Applied Biosystems).

Statistical Analysis

Genome-wide association analysis at the single marker level and the HWE analysis in the case-control samples were performed using PLINK[23]; R package was used for the genome wide P value plot. The regional plots were generated using LocusZoom[24]. In the replication studies, allelic association analysis was conducted using SHEsis[25]. The GWAS and replication data were also combined using meta-analysis using PLINK[23]. Conditional logistic regression was used to test for independent effects of an individual SNP[26,27].

Results

Totally, 45 SNPs were found to be associated with PCOS. The detailed analysis information is listed in Tables 3-5.

In fact, the SNPs represent regions, which associate with PCOS and may comprise many SNPs. Among these regions, significant evidence was found for the first identified loci, 2p16.3, 2p21, and 9q33.3[26], and the SNPs representing these regions are rs13405728 (2p16.3; $P_{GWAS-meta}$=3.77×10$^{-9}$), rs13429458 (2p21, $P_{GWAS-meta}$=4.17×10$^{-13}$), rs12478601 (2p21, $P_{GWAS-meta}$=3.37×10$^{-10}$), rs2479106 (9q33.3, $P_{GWAS-meta}$=5.14×10$^{-10}$) and rs10818854 (9q33.3, $P_{GWAS-meta}$=2.50E-04). SNPs in 19 other regions beyond the reported 3 showed association at $P_{GWAS-meta}$ value<10$^{-5}$ with PCOS susceptibility in the GWAS-meta analysis.

However, variants in the FSHR gene, which locates in 2p16.3 but not directly supported in the previous GWAS, also show $P_{GWAS-meta}$ values<10$^{-5}$. And conditional logistic analysis supports that signals in FSHR is independent from the previous report. Therefore, the inventor selected the most significant SNPs from totally 20 regions for validation (the Replication I study).

Among these 20 regions, 7 were validated in the Replication I stage (P<0.05 with the same allelic odds ratio direction), and other 3 regions had SNPs with P<5×10$^{-6}$ in the GWAS-REP1 meta-analysis. SNPs from these 10 regions were genotyped again in an independent sample set (Replication II). As a result, common variants in 8 regions, 9q22.32, 11q22.1, 12q13.2, 12q14.3, 16q12.1, 19p13.3, 20q13.2 and the FSHR gene (2p16.3), showed overall combined evidence of association at P value<5×10$^{-8}$, by a meta-analysis of all stages under fixed-effects model. The results strongly support the associations between those regions and PCOS.

On 9q22.32, the most significant SNP is rs3802457 ($P_{GWAS-REP-Meta}$=5.28×10$^{-14}$, $OR_{GWAS-REP-Meta}$=0.77), which locates in the intron region of the C9orf3 gene (FIG. 3). Controlling for rs3802457, rs4385527 ($P_{GWAS-REP-Meta}$=5.87×10$^{-9}$, $OR_{GWAS-REP-Meta}$=0.84) shows independent association in conditional logistic regression analysis, and it also locates in C9orf3. C9orf3 is a member of the M1 zinc aminopeptidase family. It is a zinc-dependent metallopeptidase that catalyzes the removal of an amino acid from the amino terminus of a protein or peptide, and may play a role in the generation of angiotensin IV. SNP rs3802458 within C9orf3 is reported associated with the development of erectile dysfunction (ED) in African-American men following radiotherapy for prostate cancer[28]. ED in men and PCOS in women occurred when people develop conditions with inadequate or excessive amounts of sexual hormones. Interestingly, FSHR gene (rs2268363) has been identified as the most significantly associated with ED[28], and strong association evidence between FSHR and PCOS was also identified (discussed below).

On 11q22.1, rs1894116 (PGWAS-REP-Meta=1.08×10$^{-22}$, $OR_{GWAS-REP-Meta}$=1.27) locates in the intron region of YAP1 (MIM: 606608) (FIG. 3). Controlling for rs1894116, conditional logistic regression analysis reveals that there is no additional association signal. YAP1, containing a WW domain, is a transcriptional regulator which can act both as a coactivator and a corepressor and is the critical downstream regulatory target in the Hippo signaling pathway that plays a pivotal role in organ size control and tumor suppression by restricting proliferation and promoting apoptosis. YAP overexpression alters the expression of genes associated with cell proliferation, apoptosis, migration, adhesion, and epithelial-to-mesenchymal transition[29]. Mice embryos with Yap1 null mutation die between embryonic days E9.5 and E10.5 due to yolk sac avasculogenesis and failure of attachment between the allantois and the chorion[30].

On 12q13.2, the most significant SNP rs705702 (PGWAS-REP-Meta=8.64×10$^{-26}$, $OR_{GWAS-REP-Meta}$=1.27) locates in the intergenic region between RAB5B (MIM: 179514) and SUOX (MIM: 606887) (FIG. 3). Controlling for rs705702, conditional logistic regression analysis reveals that there is no additional association signal. RAB5B is a member of the RAS superfamily, and it is associated with the plasma membrane and early endosomes. SUOX encodes a homodimeric protein localized to the intermembrane space of mitochondria. There are several SNPs showing evidence of association with PCOS risk. Of them, rs2292239 ($P_{GWAS-REP-Meta}$=2.72×10$^{-22}$, $OR_{GWAS-REP-Meta}$=1.25) appears to be a most interesting one, which is reported associated with Type 1 diabetes[31-33] and Type 1 diabetes autoantibodies[34]. Rs2292239 locates in intron 7 of ERBB3. ERBB3, an activator of the phosphatidylinositol-3-kinase/Akt pathway, is a member of the epidermal growth factor tyrosine kinase receptor family which regulates cell survival and vesicle trafficking. ERBB3 plays a critical role in determining antigen presenting cells function[35].

On 12q14.3, rs2272046 (PGWAS-REP-Meta=1.95×10$^{-21}$, $OR_{GWAS-REP-Meta}$0.70) locates in an intronic region of HMGA2 (MIM: 600698), which encodes a protein with structural DNA-binding domains and acts as a transcriptional regulating factor (FIG. 3). Controlling for rs2272046, there is no additional association signals in this region. HMGA2 has previously been identified to be associated with adult stature[36], vascular tumors including angiomyxomas and pulmonary hamartomas[37], and Type 2 Diabetes[38]. Interestingly, a mutation in the gene can result in the "pygmy" mouse, with a significant reduction in body weight, reduced amounts of fat tissue, and infertility in both sexes[39], which suggests its vital role in growth and reproduction.

On 16q12.1, the most significant SNP is rs4784165 ($P_{GWAS-REP-Meta}$3.64×10$^{-11}$, $OR_{GWAS-REP-Meta}$=1.15) (FIG. 3). Controlling for rs4784165, conditional logistic regression analysis reveals that there is no additional association signal. TOX3 (MIM: 611416) is the nearest gene to this top signal. TOX3 belongs to the large and diverse family of HMG-box proteins that function as architectural factors in the modification of chromatin structure by bending and unwinding DNA[40].

On 19p13.3, rs2059807 ($P_{GWAS-REP-Meta}$=1.09×10$^{-8}$, $OR_{GWAS-REP-meta}$=1.14) locates in the intron region of the INSR gene (MIM: 147670) (FIG. 3). Controlling for rs2059807, conditional logistic regression analysis reveals that there is no additional association signals. INSR plays an important role in insulin metabolism. The tyrosine kinase domain mutations of the insulin receptor have been shown to cause severe hyperinsulinemia and insulin resistance[41-43]. In previous studies, common SNP in INSR gene has been reported to be associated with PCOS in Han Chinese and Caucasian[44,45]. Insr null mice grow slowly and die by 7 days of age with ketoacidosis, high serum insulin and triglycerides, low glycogen stores and fatty livers[46].

On 20q13.2, the top signal is rs6022786 ($P_{GWAS-REP-Meta}$=1.83×10$^{-9}$, $OR_{GWAS-REP-Meta}$=1.13), locates in an intergenic region between genes SUMO1P1 and ZNF217 (MIM: 602967) (FIG. 3). Controlling for rs6022786, conditional logistic regression analysis reveals that there is no additional association signals. SUMO1P1 is the SUMO1 pseudogene 1. ZNF217, zinc finger protein 217, can attenuate apoptotic signals resulting from telomere dysfunction as well as from doxorubicin-induced DNA damage, may promote neoplastic transformation by increasing cell survival during telomeric crisis, and may promote later stages of malignancy by increasing cell survival during chemotherapy[47].

And, 2p16.3 has been reported in the previous GWAS of PCOS[26]. In that study, global significant findings in this region only locates in the LHCGR gene (MIM: 152790), and the top signal was not directly linked with the FSHR gene (MIM: 136435), mainly due to a recombination hot spot. However, FSHR has been considered to be one of the most compelling candidate genes for PCOS for a long time[48]. FSHR null mutant females are sterile with small ovaries, blocked follicular development, atrophic uterus and imperforate vagina, and null mutant males are fertile despite reduction in testis weight, oligozoospermia and reduced testosterone levels[49] In the current study, SNPs in the FSHR gene meet the selection criteria for validation in the initial stage, and global significant findings were obtained in the combined analysis (top signal is rs2268361, $P_{GWAS-REP-Meta}$=9.89×10$^{-13}$, $OR_{GWAS-REP-Meta}$=0.87) (FIG. 3). Conditional logistical regression analysis supports that the association of FSHR is independent from those previous signals in LHCGR.

Finally, independent 15 SNPs are selected to represent these regions, which are most associated with PCOS. The 15 SNPs refer to SNP marker Nos. 6, 11, 22, 23, 25, 29, 30, 33, 34, 35, 37, 41, 42, 43 and 44.

TABLE 3

Analysis results for the No. 1-28 SNP markers in GWAS-I

| SNP marker No. | Allele[a] | GWAS 744 cases, 895 controls | | | | Replication 1 2840 cases, 5012 controls | | | |
|---|---|---|---|---|---|---|---|---|---|
| | | MAF | | | | MAF | | | |
| | | Case | Control | OR | p[b] | Case | Control | OR | p |
| 1 | A/G | 0.130 | 0.216 | 0.54 | 2.93 × 10$^{-09}$ | 0.151 | 0.203 | 0.70 | 2.22 × 10$^{-16}$ |
| 2 | T/C | 0.159 | 0.232 | 0.62 | 3.46 × 10$^{-07}$ | 0.158 | 0.211 | 0.70 | 3.11 × 10$^{-15}$ |
| 3 | G/A | 0.244 | 0.329 | 0.66 | 2.71 × 10$^{-07}$ | 0.242 | 0.291 | 0.78 | 1.96 × 10$^{-09}$ |
| 4 | A/C | 0.207 | 0.305 | 0.60 | 1.20 × 10$^{-09}$ | 0.230 | 0.281 | 0.76 | 7.42 × 10$^{-11}$ |
| 5 | A/G | 0.233 | 0.329 | 0.62 | 1.06 × 10$^{-08}$ | 0.249 | 0.304 | 0.76 | 1.61 × 10$^{-12}$ |
| 6 | C/A | 0.132 | 0.207 | 0.59 | 1.05 × 10$^{-07}$ | 0.134 | 0.186 | 0.68 | 5.55 × 10$^{-16}$ |
| 7 | T/C | 0.234 | 0.322 | 0.64 | 3.02 × 10$^{-08}$ | 0.250 | 0.300 | 0.78 | 1.09 × 10$^{-10}$ |
| 8 | G/A | 0.237 | 0.325 | 0.64 | 6.07 × 10$^{-08}$ | 0.250 | 0.303 | 0.77 | 2.98 × 10$^{-11}$ |
| 9 | G/A | 0.241 | 0.321 | 0.67 | 1.08 × 10$^{-06}$ | 0.254 | 0.308 | 0.77 | 3.51 × 10$^{-12}$ |
| 10 | T/C | 0.151 | 0.223 | 0.62 | 1.24 × 10$^{-06}$ | 0.165 | 0.213 | 0.73 | 3.61 × 10$^{-12}$ |
| 11 | T/C | 0.220 | 0.314 | 0.61 | 5.55 × 10$^{-09}$ | 0.235 | 0.291 | 0.75 | 2.80 × 10$^{-13}$ |
| 12 | C/T | 0.229 | 0.323 | 0.62 | 1.89 × 10$^{-08}$ | 0.239 | 0.296 | 0.75 | 2.08 × 10$^{-13}$ |
| 13 | A/G | 0.226 | 0.312 | 0.64 | 1.92 × 10$^{-07}$ | 0.238 | 0.296 | 0.74 | 1.50 × 10$^{-13}$ |
| 14 | G/A | 0.175 | 0.254 | 0.62 | 3.95 × 10$^{-07}$ | 0.191 | 0.233 | 0.77 | 4.85 × 10$^{-09}$ |
| 15 | A/G | 0.176 | 0.251 | 0.64 | 1.23 × 10$^{-06}$ | 0.178 | 0.229 | 0.73 | 5.23 × 10$^{-13}$ |
| 16 | A/G | 0.177 | 0.251 | 0.64 | 1.90 × 10$^{-06}$ | 0.187 | 0.232 | 0.76 | 1.15 × 10$^{-10}$ |
| 17 | T/A | 0.175 | 0.251 | 0.63 | 1.00 × 10$^{-06}$ | 0.180 | 0.226 | 0.75 | 3.92 × 10$^{-11}$ |
| 18 | G/C | 0.174 | 0.247 | 0.64 | 2.06 × 10$^{-06}$ | 0.182 | 0.220 | 0.79 | 6.54 × 10$^{-08}$ |
| 19 | C/T | 0.177 | 0.256 | 0.63 | 4.94 × 10$^{-07}$ | 0.187 | 0.235 | 0.74 | 5.92 × 10$^{-11}$ |
| 20 | T/C | 0.232 | 0.324 | 0.63 | 4.19 × 10$^{-08}$ | 0.250 | 0.302 | 0.77 | 3.77 × 10$^{-11}$ |
| 21 | T/C | 0.265 | 0.357 | 0.65 | 6.11 × 10$^{-08}$ | 0.290 | 0.333 | 0.82 | 1.18 × 10$^{-07}$ |
| 22 | G/A | 0.188 | 0.274 | 0.61 | 2.54 × 10$^{-07}$ | 0.192 | 0.237 | 0.76 | 3.11 × 10$^{-10}$ |
| 23 | A/G | 0.135 | 0.079 | 1.80 | 1.20 × 10$^{-06}$ | 0.123 | 0.087 | 1.46 | 8.08 × 10$^{-12}$ |
| 24 | C/T | 0.132 | 0.073 | 1.94 | 1.33 × 10$^{-07}$ | 0.110 | 0.080 | 1.43 | 5.75 × 10$^{-10}$ |
| 25 | G/A | 0.294 | 0.216 | 1.51 | 5.09 × 10$^{-07}$ | 0.276 | 0.223 | 1.33 | 4.59 × 10$^{-13}$ |
| 26 | C/T | 0.222 | 0.139 | 1.76 | 2.79 × 10$^{-09}$ | 0.173 | 0.135 | 1.34 | 4.37 × 10$^{-10}$ |
| 27 | A/T | 0.295 | 0.214 | 1.53 | 3.27 × 10$^{-07}$ | 0.267 | 0.225 | 1.26 | 9.11 × 10$^{-09}$ |
| 28 | C/A | 0.134 | 0.069 | 2.08 | 6.13 × 10$^{-09}$ | 0.112 | 0.083 | 1.39 | 8.20 × 10$^{-09}$ |

TABLE 3-continued

Analysis results for the No. 1-28 SNP markers in GWAS-I

| SNP marker No. | Replication 2 (498 cases, 780 controls) MAF Case | Control | OR | p | Meta-analysis OR [95% CI] | p |
|---|---|---|---|---|---|---|
| 1 | 0.184 | 0.225 | 0.78 | 0.029 | 0.66 [0.61-0.72] | $5.80 \times 10^{-23}$ |
| 2 | 0.176 | 0.223 | 0.74 | 0.0046 | 0.69 [0.64-0.75] | $2.17 \times 10^{-22}$ |
| 3 | 0.265 | 0.308 | 0.81 | 0.046 | 0.74 [0.69-0.80] | $1.78 \times 10^{-15}$ |
| 4 | 0.209 | 0.274 | 0.70 | 0.00042 | 0.72 [0.68-0.78] | $1.59 \times 10^{-20}$ |
| 5 | 0.240 | 0.303 | 0.73 | 0.00077 | 0.73 [0.68-0.78] | $1.95 \times 10^{-21}$ |
| 6 | 0.153 | 0.196 | 0.74 | 0.0073 | 0.67 [0.62-0.72] | $1.73 \times 10^{-23}$ |
| 7 | 0.238 | 0.299 | 0.73 | 0.0012 | 0.75 [0.70-0.80] | $1.15 \times 10^{-18}$ |
| 8 | 0.271 | 0.302 | 0.86 | 0.10 | 0.75 [0.71-0.81] | $3.14 \times 10^{-17}$ |
| 9 | 0.245 | 0.302 | 0.75 | 0.0080 | 0.73 [0.68-0.79] | $4.21 \times 10^{-17}$ |
| 10 | 0.185 | 0.212 | 0.84 | 0.12 | 0.72 [0.67-0.78] | $2.77 \times 10^{-17}$ |
| 11 | 0.228 | 0.298 | 0.69 | 0.00014 | 0.72 [0.67-0.77] | $3.48 \times 10^{-23}$ |
| 12 | 0.252 | 0.314 | 0.74 | 0.0011 | 0.72 [0.68-0.77] | $2.87 \times 10^{-22}$ |
| 13 | 0.247 | 0.303 | 0.76 | 0.0038 | 0.73 [0.68-0.78] | $2.83 \times 10^{-21}$ |
| 14 | 0.189 | 0.246 | 0.72 | 0.0015 | 0.74 [0.69-0.79] | $1.71 \times 10^{-16}$ |
| 15 | 0.186 | 0.240 | 0.72 | 0.0019 | 0.71 [0.66-0.77] | $2.74 \times 10^{-20}$ |
| 16 | 0.197 | 0.245 | 0.76 | 0.022 | 0.71 [0.65-0.77] | $9.88 \times 10^{-17}$ |
| 17 | 0.186 | 0.241 | 0.72 | 0.0015 | 0.73 [0.68-0.78] | $1.32 \times 10^{-18}$ |
| 18 | 0.185 | 0.242 | 0.71 | 0.00082 | 0.75 [0.70-0.81] | $7.49 \times 10^{-15}$ |
| 19 | 0.202 | 0.252 | 0.75 | 0.0063 | 0.72 [0.67-0.78] | $4.31 \times 10^{-18}$ |
| 20 | 0.236 | 0.301 | 0.72 | 0.00054 | 0.74 [0.69-0.79] | $1.14 \times 10^{-19}$ |
| 21 | 0.291 | 0.324 | 0.86 | 0.098 | 0.79 [0.74-0.84] | $2.36 \times 10^{-13}$ |
| 22 | 0.181 | 0.269 | 0.60 | $7.93 \times 10^{-07}$ | 0.71 [0.67-0.77] | $7.55 \times 10^{-21}$ |
| 23 | 0.097 | 0.073 | 1.36 | 0.042 | 1.51 [1.37-1.65] | $9.40 \times 10^{-18}$ |
| 24 | 0.085 | 0.072 | 1.21 | 0.22 | 1.48 [1.34-1.63] | $1.39 \times 10^{-15}$ |
| 25 | 0.252 | 0.219 | 1.21 | 0.059 | 1.34 [1.26-1.43] | $8.12 \times 10^{-19}$ |
| 26 | 0.143 | 0.139 | 1.03 | 0.79 | 1.37 [1.27-1.48] | $2.09 \times 10^{-15}$ |
| 27 | 0.237 | 0.218 | 1.11 | 0.29 | 1.28 [1.20-1.37] | $1.42 \times 10^{-13}$ |
| 28 | 0.085 | 0.073 | 1.17 | 0.31 | 1.47 [1.33-1.61] | $6.90 \times 10^{-15}$ |

[a]Minor allele/major allele.
[b]PCA adjusted P values. MAF, minor allele frequency

TABLE 4

Analysis results for the No. 29-44 SNP markers in GWAS-II

| SNP marker No. | Allele[a] | GWAS I (744 cases VS 895 controls) MAF cases/controls | OR [95% CI] | P | GWAS II (1510 cases VS 2106 controls) MAF cases/controls | OR [95% CI] | P | GWAS META OR | P | REP I (1908 cases VS 1913 controls) MAF cases/controls | OR [95% CI] | P |
|---|---|---|---|---|---|---|---|---|---|---|---|---|
| 29 | T/C[b] | 0.44/0.49 | 0.83 [0.72-0.95] | 6.68E−03 | 0.45/0.49 | 0.84 [0.76-0.93] | 4.19E−04 | 0.84 | 8.82E−06 | 0.47/0.49 | 0.91 [0.83-0.99] | 3.31E−02 |
| 30 | C/T | 0.1/0.09 | 1.18 [0.94-1.49] | 1.60E−01 | 0.23/0.17 | 1.37 [1.22-1.55] | 3.72E−07 | 1.33 | 2.56E−07 | 0.22/0.18 | 1.32 [1.18-1.47] | 2.51E−06 |
| 31 | A/G | 0.2/0.18 | 1.14 [0.95-1.36] | 1.51E−01 | 0.21/0.17 | 1.34 [1.19-1.52] | 3.01E−06 | 1.27 | 3.33E−06 | 0.24/0.2 | 1.25 [1.12-1.39] | 8.09E−05 |
| 32 | C/T | 0.39/0.43 | 0.85 [0.73-0.97] | 1.92E−02 | 0.38/0.43 | 0.83 [0.75-0.91] | 1.55E−04 | 0.83 | 8.95E−06 | 0.41/0.43 | 0.9 [0.82-0.99] | 2.56E−02 |
| 33 | G/A | 0.15/0.17 | 0.82 [0.68-0.99] | 4.35E−02 | 0.15/0.19 | 0.77 [0.67-0.87] | 6.77E−05 | 0.78 | 9.62E−06 | 0.19/0.2 | 0.9 [0.82-0.99] | 2.32E−02 |
| 34 | G/A | 0.06/0.09 | 0.68 [0.52-0.89] | 4.28E−03 | 0.06/0.08 | 0.7 [0.57-0.85] | 2.65E−04 | 0.69 | 3.81E−06 | 0.08/0.09 | 0.88 [0.75-1.03] | 1.17E−01 |
| 35 | G/A | 0.25/0.19 | 1.45 [1.23-1.72] | 1.36E−05 | 0.23/0.19 | 1.23 [1.09-1.39] | 5.91E−04 | 1.3 | 1.11E−07 | 0.24/0.2 | 1.21 [1.09-1.35] | 6.29E−04 |
| 36 | A/G | 0.29/0.23 | 1.42 [1.21-1.67] | 1.18E−05 | 0.07/0.06 | 1.21 [0.99-1.48] | 6.16E−02 | 1.34 | 4.53E−06 | 0.29/0.26 | 1.18 [1.06-1.30] | 2.07E−03 |
| 37 | G/A | 0.29/0.22 | 1.41 [1.21-1.66] | 1.93E−05 | 0.3/0.26 | 1.28 [1.15-1.43] | 7.92E−06 | 1.32 | 1.09E−09 | 0.29/0.25 | 1.21 [1.09-1.34] | 2.27E−04 |
| 38 | C/T | 0.3/0.24 | 1.39 [1.19-1.62] | 3.43E−05 | 0.3/0.25 | 1.28 [1.15-1.44] | 1.02E−05 | 1.32 | 2.11E−09 | 0.29/0.25 | 1.23 [1.11-1.36] | 8.77E−05 |
| 39 | G/A | 0.13/0.11 | 1.23 [0.99-1.52] | 6.22E−02 | 0.3/0.25 | 1.29 [1.15-1.44] | 7.36E−06 | 1.27 | 1.28E−06 | 0.29/0.25 | 1.19 [1.07-1.32] | 9.75E−04 |
| 40 | T/G | 0.09/0.08 | 1.14 [0.89-1.47] | 3.03E−01 | 0.3/0.25 | 1.29 [1.15-1.44] | 6.02E−06 | 1.26 | 5.22E−06 | 0.28/0.23 | 1.27 [1.15-1.41] | 5.16E−06 |

TABLE 4-continued

Analysis results for the No. 29-44 SNP markers in GWAS-II

| 41 | C/A | 0.07/0.1 | 0.71 [0.55-0.91] | 6.78E-03 | 0.07/0.09 | 0.65 [0.54-0.78] | 5.38E-06 | 0.67 | 1.43E-07 | 0.07/0.09 | 0.8 [0.68-0.95] | 1.07E-02 |
| --- | --- | --- | --- | --- | --- | --- | --- | --- | --- | --- | --- | --- |
| 42 | G/T | 0.07/0.06 | 1.09 [0.82-1.45] | 5.55E-01 | 0.39/0.33 | 1.28 [1.16-1.42] | 1.95E-06 | 1.26 | 2.82E-06 | 0.36/0.34 | 1.09 [0.99-1.20] | 7.24E-02 |
| 43 | G/A | 0.34/0.28 | 1.34 [1.16-1.56] | 1.16E-04 | 0.34/0.29 | 1.19 [1.07-1.33] | 1.66E-03 | 1.24 | 1.58E-06 | 0.31/0.28 | 1.16 [1.05-1.28] | 4.40E-03 |
| 44 | A/G | 0.38/0.32 | 1.32 [1.14-1.53] | 1.72E-04 | 0.37/0.33 | 1.21 [1.09-1.34] | 3.76E-04 | 1.24 | 4.05E-07 | 0.35/0.33 | 1.11 [1.01-1.22] | 3.77E-02 |

| | | | REP II (6318 cases VS 5665 controls) | | | | |
| --- | --- | --- | --- | --- | --- | --- | --- |
| SNP marker | GWAS-REP I META | | MAF cases/ controls | OR [95% CI] | | GWAS-REPs META | |
| No. | OR | P | | | P | OR | P |
| 29 | 0.87 | 2.07E-06 | 0.47/0.5 | 0.87 [0.83-0.92] | 1.05E-07 | 0.87 | 9.89E-13 |
| 30 | 1.32 | 3.02E-12 | 0.22/0.2 | 1.11 [1.05-1.19] | 6.93E-04 | 1.19 | 2.35E-12 |
| 31 | 1.26 | 1.13E-09 | 0.21/0.19 | 1.14 [1.07-1.22] | 5.74E-05 | 1.19 | 2.19E-12 |
| 32 | 0.86 | 1.53E-06 | 0.4/0.43 | 0.87 [0.83-0.92] | 2.26E-07 | 0.87 | 1.63E-12 |
| 33 | 0.85 | 4.29E-06 | 0.15/0.17 | 0.86 [0.81-0.93] | 4.64E-05 | 0.84 | 5.87E-09 |
| 34 | 0.77 | 9.88E-06 | 0.08/0.1 | 0.76 [0.69-0.83] | 1.07E-09 | 0.77 | 5.28E-14 |
| 35 | 1.26 | 4.38E-10 | 0.23/0.19 | 1.27 [1.20-1.36] | 4.45E-14 | 1.27 | 1.08E-22 |
| 36 | 1.24 | 1.21E-07 | 0.28/0.25 | 1.22 [1.15-1.28] | 5.77E-11 | 1.22 | 3.73E-17 |
| 37 | 1.27 | 2.34E-12 | 0.29/0.24 | 1.26 [1.19-1.34] | 7.44E-15 | 1.27 | 8.64E-26 |
| 38 | 1.28 | 1.36E-12 | — | — | — | — | — |
| 39 | 1.23 | 7.46E-09 | 0.28/0.24 | 1.24 [1.17-1.31] | 9.78E-13 | 1.24 | 3.90E-20 |
| 40 | 1.27 | 1.17E-10 | 0.28/0.23 | 1.25 [1.17-1.32] | 3.87E-13 | 1.25 | 2.72E-22 |
| 41 | 0.73 | 1.89E-08 | 0.07/0.09 | 0.69 [0.63-0.76] | 9.10E-15 | 0.7 | 1.95E-21 |
| 42 | 1.17 | 4.55E-06 | 0.39/0.36 | 1.14 [1.08-1.21] | 1.57E-06 | 1.15 | 3.64E-11 |
| 43 | 1.2 | 4.11E-08 | 0.33/0.31 | 1.09 [1.02-1.15] | 6.61E-03 | 1.14 | 1.09E-08 |
| 44 | 1.18 | 2.30E-07 | 0.37/0.35 | 1.1 [1.04-1.16] | 4.82E-04 | 1.13 | 1.83E-09 |

[a]Minor allele/major allele.
[b]N represents the nucleotide more correlative to PCOS in the site.

TABLE 5

Analysis result for the No. 45 SNP marker.

| SNP marker | Allele frequency comparison | | | | | Meta-analysis | | | |
| --- | --- | --- | --- | --- | --- | --- | --- | --- | --- |
| No. | MAF | PCOS | CTRL | $\chi^2$ | P | OR | P | P(R) | OR | Q |
| 45 | A | 0.24 | 0.19 | 14.51 | 0.00014 | 1.32 (1.144-1.523) | 3.98E-09 | 3.98E-09 | 1.393 | 0.3853 |

MAF, minor allele frequency.
In meta-analysis, the P is calculated by fixed effect model and P(R) is calculated by random effect model.

Based on the study above and practice use, detecting genotypes at the site N of at least 15 SNP markers, for example, all 45 SNP markers in the present invention, is useful for predicting or diagnosing PCOS. However, detecting genotypes at the site N of 15 independent SNP markers of 6, 11, 22, 23, 25, 29, 30, 33, 34, 35, 37, 41, 42, 43 and 44 can also work, with less expense.

Detecting Genotypes at the Site N of the SNP Markers

There are many processes for detecting genotypes at the site N of the SNP markers, for example, by hybridization or sequencing.

As to hybridization, probes are designed to specifically hybridize with the locus of SNP, and then the hybridization is analyzed whether SNP is present. An example of probes for all 45 SNPs is given just for the purpose of exemplifying, which is not intended to limit the scope of the invention. A person skilled in the art could easily design similar probes to hybridize with the SNPs, which all fall into the scope of the invention.

Generally, probes are presented in a carrier, for example, a chip, so that more than one SNP markers can be detected at a time. The present invention also provides a chip comprising probes detecting the SNP markers shown as SEQ ID NO. 6, 11, 22, 23, 25, 29, 30, 33, 34, 35, 37, 41, 42, 43 and 44 (i.e. SNPs of rs13429458, rs12478601, rs13405728, rs10818854, rs2479106, rs2268361, rs2349415, rs4385527, rs3802457, rs1894116, rs705702, rs2272046, rs4784165, rs2059807 and rs6022786). A person skilled in the art well knows how to produce such chip when the probes are selected.

As to sequencing, primers should be designed forward and afterward the interested locus. An example of primers for all 45 SNPs (listed in Table 2) is given just for the purpose of exemplifying, which is not intended to limit the scope of the invention. A person skilled in the art can easily design similar primers to sequence the SNP markers, which also fall into the scope of the present invention. Furthermore, the process and agents used in the sequencing are also well known in the art.

Another useful method for genotyping SNP markers uses iPLEX of Sequenom platform (Sequenom, Inc., San Diego, Calif.). Polymerase chain reaction (PCR) and extension primers for the SNPs were designed using the MassARRAY Assay Design 3.0 software. PCR and extension reactions are performed according to the manufacturer's instructions, and extension product sizes were determined by mass spectrometry using the Sequenom iPLEX system.

Method of Predicting or Diagnosing PCOS

The 45 SNP markers based on the present invention can be used to predict or diagnose PCOS. Firstly, the DNA from peripheral blood or saliva of a subject is extracted, and then, the genotypes at the site N of the SNPs are detected, for example, by hybridization with probes or chips above, or by sequencing. At last, the results will be analyzed to predict the risk of PCOS.

EXAMPLES

The following examples are just for the purpose of exemplifying and should not be considered to limit the scope of the present invention.

Example 1

All the 45 SNP markers are amplified by PCR using the primers listed in Table 2. The following processes are followed for the PCR reaction.

A. Reaction System

| Reagent | Volume (μL) |
| --- | --- |
| ddH$_2$O | 1.8 |
| 10* buffer | 0.5 |
| Mg$^{2+}$ | 0.4 |
| dNTP | 0.1 |
| Hotstar | 0.2 |
| F Primer/R Primer | 1 |
| DNA sample | 1 |
| Total | 5 |

B. Reaction Process

| | | |
| --- | --- | --- |
| Pre-denaturation | 95° C. | 2 min |
| 45 cycles of | 95° C. | 30 s |
| | 60° C. | 30 s |
| | 72° C. | 60 s |
| Extension | 72° C. | 5 min |
| | 25° C. | ∞ |

Figure 4A:
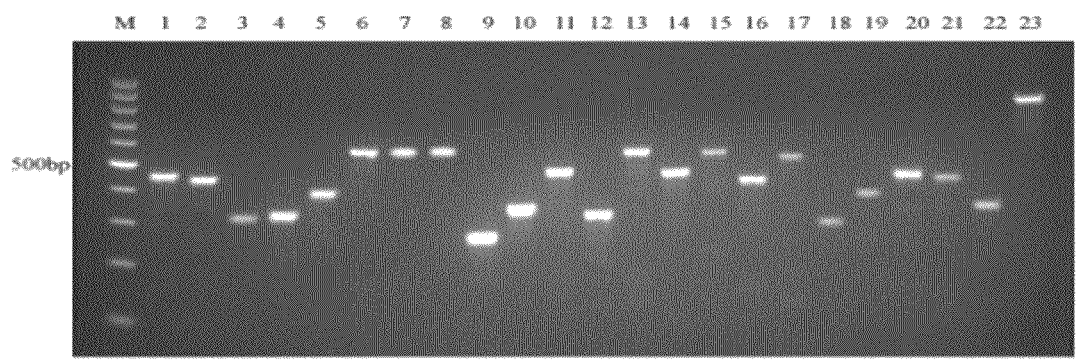
FIG. 4A-4B. PCR electrophoretograms for the 45 SNP markers.
Figure 4B:
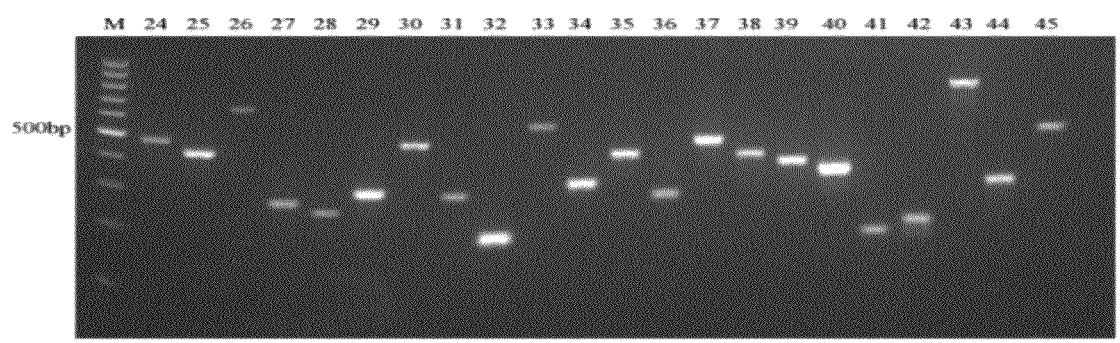

The products are tested by electrophoresis and sequencing and are confirmed. FIG. 4 shows the electrophoretogram for all the 45 SNP markers.

Example 2

1. Extracting DNA from peripheral blood or saliva of a subject, purifying DNA and adjusting DNA concentration to 20 ng/mL.
2. Detecting genotypes at the site N of 15 SNP markers by sequencing and the 15 SNP markers are shown as SEQ ID NO. 6, 11, 22, 23, 25, 29, 30, 33, 34, 35, 37, 41, 42, 43 and 44. The primers used are listed in Table 2.
3. Method:
I. PCR Reaction
A. Reaction System

| Reagent | Volume (μL) |
| --- | --- |
| ddH$_2$O | 1.8 |
| 10* buffer | 0.5 |
| Mg$^{2+}$ | 0.4 |
| dNTP | 0.1 |
| Hotstar | 0.2 |
| F Primer/R Primer | 1 |
| DNA sample | 1 |
| Total | 5 |

B. Reaction Process

| | | |
| --- | --- | --- |
| Pre-denaturation | 95° C. | 2 min |
| 45 cycles of | 95° C. | 30 s |
| | 60° C. | 30 s |
| | 72° C. | 60 s |
| Extension | 72° C. | 5 min |
| | 25° C. | ∞ |

C. Purification of PCR Product

The PCR product is precipitated by 25 μL PEG (22%, w/v) and 2 μL NaCl (5 M) at room temperature. Then the plate is stored at 4° C. for 30 minutes. The left-over PEG was washed by 80 μL of 75% ethanol three times by centrifugation at 4° C.

D. Cycle Sequencing of Purified PCR Product

The purified DNA was dissolved in 5 μL ddH$_2$O.

| Reagent | Volume (μL) |
| --- | --- |
| ddH$_2$O | 3.7 |
| BigDye Terminator 3.1 Sequencing Buffer (ABI) | 1.125 |
| Primer | 0.675 |
| Total | 5.5 |

Then, the plates are mixed well and spun shortly. The initial denaturation procedure is performed by a rapid thermal ramp to 96° C. and lasts for 1 minute. 25 cycles of reactions are performed with denaturation for 10 seconds over 96° C., annealing for 5 seconds over 50° C. and extension for 4 minutes over 60° C. Rapid thermal ramp to 4° C. is performed. And the product is hold until ready to purify.

E. Ethanol/EDTA/Sodium Acetate Precipitation

2 μL of 125 mM EDTA and 2 μL of 3 M sodium acetate are added to each well. And then 50 μL 100% ethanol is added to each well. The plate is sealed and mixed by inverting 4 times. The plate is incubated at room temperature for 15 minutes. Then the precipitated DNA is washed with 75% ethanol for 3 times.

F. Capillary Electrophoresis on ABI 3730 XL Genetic Analyzer

Each well is added 10 μL formamide and denatured at 95° C. for 5 minutes. The precipitated DNA is loaded on ABI 3730 XL genetic analyzer for capillary electrophoresis.

II. MassARRAY

A. Main Apparatus and Reagent
1) Amplification: ABI GeneAmp® 9700 384 Dual;
2) Mechanical arm: MassARRAY Nanodispenser RS 1000;
3) Analyze: MassARRAY Compact System;
4) Reagent: Complete Genotyping Reagent Kit for MassARRAY® Compact 384

B. Procedure

Perform 384 PCR reactions (same multiplexed assays, different DNA). These instructions cover performing PCR for a whole 384-well microtiter plate of reactions in which the same assay will be applied to different DNA.

Prepare a PCR Cocktail as Described in the Following Table

1) Add the reagents in the order in which they appear in the table for multiplexed PCR cocktail, without DNA, for 384 reactions (same multiplexed assays, different DNA).

| Component | Volume (μL) |
| --- | --- |
| ddH$_2$O | 1.8 |
| 10* buffer | 0.5 |
| Mg$^{2+}$ | 0.4 |
| dNTP | 0.1 |
| Hotstar | 0.2 |
| F Primer/R Primer | 1 |
| DNA | 1 |
| Total | 5 |

2) To each well of a 384-well microtiter plate (Marsh Biomedical Products, Inc. #SP 0401 Sequen), add 1 μL of the appropriate genomic DNA (5-10 ng/μL).

3) Dispense 44 of the PCR cocktail into each well of the 384-well plate.

4) Centrifuge the microtiter plate at 1,000 RPM for 1 minute.

5) Gently mix or vortex the plate, and spin down before thermocycling.

6) Thermocycle the 384-well microtiter plate as follows:

| | | |
| --- | --- | --- |
| 94° C. | 4 minutes | |
| 94° C. | 20 seconds | 45 cycles |
| 56° C. | 30 seconds | |
| 72° C. | 1 minute | |
| 72° C. | 3 minutes | |
| 4° C. | forever | |

Prepare the SAP Enzyme Solution

1) Add the reagents in the order in which they appear in the following table into a 1.5 mL tube to prepare the SAP enzyme solution.

SAP Enzyme Solution Volume

| Component | Volume (μL) |
| --- | --- |
| SAP*Buffer | 0.17 |
| SAP Enzyme | 0.3 |
| ddH$_2$O | 1.53 |
| Total | 2 |

2) Hold the 1.5 mL tube, containing the SAP enzyme solution, to a vortex for five seconds to mix the solution.

3) Centrifuge the 1.5 mL tube of SAP enzyme solution for ten seconds at 5000 RPM.

4) 2 μL of SAP enzyme solution is added to each well in the 384-well sample microtiter plate.

5) Seal the 384-well sample microtiter plate with plate sealing film.

6) Centrifuge the 384-well sample microtiter plate at 1000 RPM for 1 minute.

7) Incubate the 384-well sample microtiter plate as follows:

| | |
| --- | --- |
| 37° C. | 40 minutes |
| 85° C. | 5 minutes |
| 4° C. | forever |

Prepare the High Plex iPLEX Gold Reaction Cocktail (Same Multiplexed Assays, Different DNA)

1) Prepare the high plex iPLEX Gold reaction cocktail, as described in the following table in a 1.5 mL tube. Add the reagents in the order in which they appear in the table. Multiplexed high plex iPLEX Gold reaction cocktail (same assays, different DNA)

| Component | Volume (μL) |
| --- | --- |
| ddH$_2$O | 0.619 |
| Primer mix | 0.94 |
| Gold*Buffer (10x) | 0.2 |
| Termination mix | 0.2 |
| Enzyme | 0.041 |
| Total | 2 |

2) Centrifuge the cocktail microtiter plate at 1000 RPM for one minute.

3) Add 2 μL the High Plex iLEX Gold reaction into 384-well sample microtiter plate.

4) Seal the 384-well sample microtiter plate with plate sealing film.

5) Centrifuge the 384-well sample microtiter plate at 1000 RPM for one minute.

6) Thermocycle the 384-well sample microtiter plate as follows:

| | | |
| --- | --- | --- |
| 94° C. | 30 seconds | |
| 94° C. | 5 seconds | For 40 cycles |
| 52° C. | 5 seconds | For 5 cycles |

| | |
|---|---|
| 80° C. | 5 seconds |
| 72° C. | 3 minutes |
| 4° C. | forever |

Clean up the High Ple iPLEX Gold Reaction Products. The cleanup of high plex iPLEX Gold reaction products involves adding water and then Clean Resin to the sample microtiter plate. Spread Clean Resin onto the 384-well dimple plate. Add nanopure water to each well of the 384-well sample microtiter plate. Add Clean Resin to the 384-well sample microtiter plate. Rotate and centrifuge the 384-well sample microtiter plate.

Acquiring Spectra

The ACQUIRE module controls the MassARRAY Analyzer Compact (Compact) to acquire spectra from SpectroCHIPs. As each SpectroCHIP is processed by the Compact, the spectral data is automatically processed and saved to the MassARRAY database.

The method involves 15 SNP markers which are most associated with PCOS and the credibility thereof is higher. The detecting process can be more easily carried out with less expense.

REFERENCES

1. Rotterdam ESHRE/ASRM-Sponsored PCOS Consensus Workshop Group: Revised 2003 consensus on diagnostic criteria and longterm health risks related to polycystic ovary syndrome. Fertil Steril 2004; 81: 19-25.
2. Goodarzi M O, Azziz R. Diagnosis, epidemiology, and genetics of the polycystic ovary syndrome. Best Prac Res Clin Endocrinol Metab 2006; 20: 193-200.
3. Ehrmann D A, Barnes R B, Rosenfield R L, Cavaghan M K, Imperial J. Prevalence of impaired glucose tolerance and diabetes in women with polycystic ovary syndrome. Diabetes Care 1999; 22: 141-6.
4. Carmina E. Cardiovascular risk and events in polycystic ovary syndrome. Climacteric 2009; 12 Suppl 1:22-5.
5. Kandaraki E, Christakou C, Diamanti-Kandarakis E. Metabolic syndrome and polycystic ovary syndrome . . . and vice versa. Arq Bras Endocrinol Metabol 2009; 53:227-37.
6. Wild S, Pierpoint T, Jacobs H, McKeigue P. Long-term consequences of polycystic ovary syndrome: results of a 31 year follow-up study. Hum Fertil(Camb) 2000; 3:101-5.
7. Legro R S, Castracane V D, Kauffman R P. Detecting insulin resistance in polycystic ovary syndrome: purposes and pitfalls. Obstet Gynecol Sury 2004; 59:141-54.
8. Espinós-Gómez J J, Corcoy R, Calaf J. Prevalence and predictors of abnormal glucose metabolism in Mediterranean women with polycystic ovary syndrome. Gynecol Endocrinol 2009; 25:199-204.
9. Kulshreshtha B, Ganie M A, Praveen E P, et al. Insulin response to oral glucose in healthy, lean young women and patients with polycystic ovary syndrome. Gynecol Endocrinol 2008; 24: 637-43.
10. Shi Y, Guo M, Yan J, et al. Analysis of clinical characteristics in large-scale Chinese women with polycystic ovary syndrome. Neuro Endocrinol Lett 2007; 28: 807-10.
11. Sudo S, Kudo M, Wada S, Sato O, Hsueh A J, Fujimoto S. Genetic and functional analyses of polymorphisms in the human FSH receptor gene. Mol Hum Reprod 2002; 8:893-9.
12. Gaasenbeek M, Powell B L, Sovio U, et al. Large-scale analysis of the relationship between CYP11A promoter variation, polycystic ovarian syndrome, and serum testosterone. J Clin Endocrinol Metab 2004; 89:2408-13.
13. Wang Y, Wu X, Cao Y, Yi L, Chen J. A microsatellite polymorphism (tttta)n in the promoter of the CYP11a gene in Chinese women with polycystic ovary syndrome. Fertil Steril 2006; 86: 223-6.
14. Chen Z J, Shi Y H, Zhao Y R, et al. Correlation between single nucleotide polymorphism of insulin receptor gene with polycystic ovary syndrome. Zhonghua Fu Chan Ke Za Zhi 2004; 39: 582-5.
15. Villuendas G, San Millán J L, Sancho J, Escobar-Morreale H F. The -597 G-->A and -174 G-->C polymorphisms in the promoter of the IL-6 gene are associated with hyperandrogenism. J Clin Endocrinol Metab 2002; 87: 1134-41.
16. Simoni M, Tempfer C B, Destenaves B, Fauser B C. Functional genetic polymorphisms and female reproductive disorders: Part I: Polycystic ovary syndrome and ovarian response. Hum Reprod Update 2008; 14: 459-84.
17. Li, Y., Willer, C. J., Ding, J., Scheet, P. & Abecasis, G. R. MaCH: using sequence and genotype data to estimate haplotypes and unobserved genotypes. *Genetic epidemiology* 34, 816-834 (2010).
18. Li, Y., Willer, C., Sanna, S. & Abecasis, G. Genotype imputation. *Annual review of genomics and human genetics* 10, 387-406 (2009).
19. Marchini, J., Howie, B., Myers, S., McVean, G. & Donnelly, P. A new multipoint method for genome-wide association studies by imputation of genotypes. *Nature genetics* 39, 906-913 (2007).
20. Howie, B. N., Donnelly, P. & Marchini, J. A flexible and accurate genotype imputation method for the next generation of genome-wide association studies. *PLoS genetics* 5, e1000529 (2009).
21. Price, A. L. et al. Principal components analysis corrects for stratification in genome-wide association studies. *Nature genetics* 38, 904-909 (2006).
22. Lindgren, C. M. et al. Genome-wide association scan meta-analysis identifies three Loci influencing adiposity and fat distribution. *PLoS genetics* 5, e1000508 (2009).
23. Purcell, S. et al. PLINK: a tool set for whole-genome association and population-based linkage analyses. *The American Journal of Human Genetics* 81, 559-575 (2007).
24. Pruim, R. J. et al. LocusZoom: regional visualization of genome-wide association scan results. *Bioinformatics* 26, 2336-2337 (2010).
25. Yong, Y. & Lin, H. E. SHEsis, a powerful software platform for analyses of linkage disequilibrium, haplotype construction, and genetic association at polymorphism loci. *Cell research* 15, 97-98 (2005).
26. Chen, Z. J. et al. Genome-wide association study identifies susceptibility loci for polycystic ovary syndrome on chromosome 2p16. 3, 2p21 and 9q33. 3. *Nature genetics* 43, 55-59 (2011).
27. Petukhova, L. et al. Genome-wide association study in alopecia areata implicates both innate and adaptive immunity. *Nature* 466, 113-117 (2010).
28. Kerns, S. L. et al. Genome-wide association study to identify single nucleotide polymorphisms (SNPs) associated with the development of erectile dysfunction in African-American men after radiotherapy for prostate cancer. *International Journal of Radiation Oncology\* Biology\* Physics* 78, 1292-1300 (2010).
29. Hao, Y., Chun, A., Cheung, K., Rashidi, B. & Yang, X. Tumor suppressor LATS1 is a negative regulator of oncogene YAP. *Journal of Biological Chemistry* 283, 5496-5509 (2008).

30. Morin-Kensicki, E. M. et al. Defects in yolk sac vasculogenesis, chorioallantoic fusion, and embryonic axis elongation in mice with targeted disruption of Yap65. *Molecular and cellular biology* 26, 77-87 (2006).
31. Barrett, J. C. et al. Genome-wide association study and meta-analysis find that over 40 loci affect risk of type 1 diabetes. *Nature genetics* 41, 703-707 (2009).
32. Cooper, J. D. et al. Meta-analysis of genome-wide association study data identifies additional type 1 diabetes risk loci. *Nature genetics* 40, 1399-1401 (2008).
33. Todd, J. A. et al. Robust associations of four new chromosome regions from genome-wide analyses of type 1 diabetes. *Nature genetics* 39, 857-864 (2007).
34. Plagnol, V. et al. Genome-Wide Association Analysis of Autoantibody Positivity in Type 1 Diabetes Cases. *PLoS Genetics* 7, e1002216 (2011).
35. Wang, H. et al. Genetically dependent ERBB3 expression modulates antigen presenting cell function and type 1 diabetes risk. *PloS one* 5, e11789 (2010).
36. Weedon, M. N. et al. A common variant of HMGA2 is associated with adult and childhood height in the general population. *Nature genetics* 39, 1245-1250 (2007).
37. Kazmierczak, B. et al. Cloning and molecular characterization of part of a new gene fused to HMGIC in mesenchymal tumors. *The American journal of pathology* 152, 431-435 (1998).
38. Voight, B. F. et al. Twelve type 2 diabetes susceptibility loci identified through large-scale association analysis. *Nature genetics* 42, 579-589 (2010).
39. Asher, H. R. et al. Disruption of the architectural factor HMGI-C: DNA-binding AT hook motifs fused in lipomas to distinct transcriptional regulatory domains. *Cell* 82, 57-65 (1995).
40. O'Flaherty, E. & Kaye, J. TOX defines a conserved subfamily of HMG-box proteins. *BMC genomics* 4, 13 (2003).
41. Moller, D. E. & Flier, J. S. Detection of an alteration in the insulin-receptor gene in a patient with insulin resistance, acanthosis nigricans, and the polycystic ovary syndrome (type A insulin resistance). *New England Journal of Medicine* 319, 1526-1529 (1988).
42. Moller, D. E., Yokota, A., White, M. F., Pazianos, A. G. & Flier, J. S. A naturally occurring mutation of insulin receptor alanine 1134 impairs tyrosine kinase function and is associated with dominantly inherited insulin resistance. *Journal of Biological Chemistry* 265, 14979-14985 (1990).
43. Taylor, S. I. et al. Mutations in insulin-receptor gene in insulin-resistant patients. *Diabetes Care* 13, 257-279 (1990).
44. Chen, Z. J. et al. Correlation between single nucleotide polymorphism of insulin receptor gene with polycystic ovary syndrome). *Zhonghua fu chan ke za zhi* 39, 582-585 (2004).
45. Siegel, S. et al. AC/T single nucleotide polymorphism at the tyrosine kinase domain of the insulin receptor gene is associated with polycystic ovary syndrome. *Fertility and sterility* 78, 1240-1243 (2002).
46. Accili, D. et al. Early neonatal death in mice homozygous for a null allele of the insulin receptor gene. *Nature genetics* 12, 106-109 (1996).
47. Huang, G. et al. ZNF217 suppresses cell death associated with chemotherapy and telomere dysfunction. *Human molecular genetics* 14, 3219-3225 (2005).
48. Simoni, M., Tempfer, C. B., Destenaves, B. & Fauser, B. Functional genetic polymorphisms and female reproductive disorders: Part I: polycystic ovary syndrome and ovarian response. *Human reproduction update* 14, 459-484 (2008).
49. Sun, L. et al. FSH directly regulates bone mass. *cell* 125, 247-260 (2006).

The invention claimed is:

1. A method of detecting a predisposition of an individual to develop polycystic ovary syndrome or at least one pathology or risk factor associated with polycystic ovary syndrome (PCOS), the method comprising:

providing DNA of the individual;

providing a plurality of probes chosen from among SEQ ID NO. 46-77, 82-97 and 100-135, or a plurality of primers chosen from among SEQ ID NO. 136-163, 168-183 and 186-221;

detecting a presence of a genotype at the site N of at least one single nucleotide polymorphism (SNP) marker of the DNA using the plurality of probes or the plurality of primers, wherein a nucleotide sequence of the at least one SNP marker is shown as: SEQ ID NO.1, wherein N is C or T; SEQ ID NO.2, wherein N is A or G; SEQ ID NO.3, wherein N is C or T; SEQ ID NO.4, wherein N is A or C; SEQ ID NO.5, wherein N is C or T; SEQ ID NO.6, wherein N is A or C; SEQ ID NO.7, wherein N is C or T; SEQ ID NO.8, wherein N is C or T; SEQ ID NO.9, wherein N is A or G; SEQ ID NO.10, wherein N is C or T; SEQ ID NO.11, wherein N is C or T; SEQ ID NO.12, wherein N is C or T; SEQ ID NO.13, wherein N is A or G; SEQ ID NO.14, wherein N is C or T; SEQ ID NO.15, wherein N is A or G; SEQ ID NO.16, wherein N is C or T; SEQ ID NO.19, wherein N is C or T; SEQ ID NO.20, wherein N is C or T; SEQ ID NO.21, wherein N is C or T; SEQ ID NO.22, wherein N is A or G; SEQ ID NO.23, wherein N is A or G; SEQ ID NO.24, wherein N is C or T; SEQ ID NO.25, wherein N is A or G; SEQ ID NO.26, wherein N is C or T; SEQ ID NO.28, wherein N is G or T; SEQ ID NO.29, wherein N is A or G; SEQ ID NO.30, wherein N is C or T; SEQ ID NO.31, wherein N is A or G; SEQ ID NO.32, wherein N is C or T; SEQ ID NO.33, wherein N is C or T; SEQ ID NO.34, wherein N is C or T; SEQ ID NO.35, wherein N is C or T; SEQ ID NO.36, wherein N is A or G; SEQ ID NO.37, wherein N is C or T; SEQ ID NO.38, wherein N is C or T; SEQ ID NO.39, wherein N is C or T; SEQ ID NO.40, wherein N is A or C; SEQ ID NO.41, wherein N is G or T; SEQ ID NO.42, wherein N is G or T; SEQ ID NO.43, wherein N is C or T; SEQ ID NO.44, wherein N is A or G; or SEQ ID NO.45, wherein N is C or T; and determining, based on the genotype of said SNP marker, that the individual has a predisposition to develop polycystic ovary syndrome or at least one pathology or risk factor associated with polycystic ovary syndrome.

2. The method of claim 1, wherein the detecting the presence of the genotype at the site N of the at least one SNP marker is carried out using the plurality of probes.

3. The method of claim 2, wherein the probes are chosen from SEQ ID NO. 46 and 47 for SNP marker NO.1; SEQ ID NO. 48 and 49 for SNP marker NO.2; SEQ ID NO. 50 and 51 for SNP marker NO.3; SEQ ID NO. 52 and 53 for SNP marker NO.4; SEQ ID NO. 54 and 55 for SNP marker NO.5; SEQ ID NO. 56 and 57 for SNP marker NO.6; SEQ ID NO. 58 and 59 for SNP marker NO.7; SEQ ID NO. 60 and 61 for SNP marker NO.8; SEQ ID NO. 62 and 63 for SNP marker NO.9; SEQ ID NO. 64 and 65 for SNP marker NO.10; SEQ ID NO. 66 and 67 for SNP marker NO.11; SEQ ID NO. 68 and 69 for SNP marker NO.12; SEQ ID NO. 70 and 71 for SNP marker NO.13; SEQ ID NO. 72 and 73 for SNP marker NO.14; SEQ ID NO. 74 and 75 for SNP marker NO.15; SEQ ID NO. 76 and 77 for SNP marker NO.16; SEQ ID NO. 82 and 83 for SNP marker NO.19; SEQ ID NO. 84 and 85 for SNP marker NO.20; SEQ ID NO. 86 and 87 for SNP marker NO.21; SEQ ID NO. 88 and 89 for SNP marker NO.22; SEQ ID NO. 90 and 91 for SNP marker NO.23; SEQ ID NO. 92 and 93 for SNP marker NO.24; SEQ ID NO. 94 and 95 for SNP marker NO.25; SEQ ID NO. 96 and 97 for SNP marker NO.26; SEQ ID NO. 100 and 101 for SNP marker NO.28; SEQ ID NO. 102 and 103 for SNP marker NO.29; SEQ ID NO. 104 and 105 for SNP marker NO.30; SEQ ID NO. 106 and 107 for SNP marker NO.31; SEQ ID NO. 108 and 109 for SNP marker NO.32; SEQ ID NO. 110 and 111 for SNP marker NO.33; SEQ ID NO. 112 and 113 for SNP marker NO.34; SEQ ID NO. 114 and 115 for SNP marker NO.35; SEQ ID NO. 116 and 117 for SNP marker NO.36; SEQ ID NO. 118 and 119 for SNP marker NO.37; SEQ ID NO. 120 and 121 for SNP marker NO.38; SEQ ID NO. 122 and 123 for SNP marker NO.39; SEQ ID NO. 124 and 125 for SNP marker NO.40; SEQ ID NO. 126 and 127 for SNP marker NO.41; SEQ ID NO. 128 and 129 for SNP marker NO.42; SEQ ID NO. 130 and 131 for SNP marker NO.43; SEQ ID NO. 132 and 133 for SNP marker NO.44; and/or SEQ ID NO. 134 and 135 for SNP marker NO.45.

4. The method of claim 2, wherein the detecting the presence of the genotype at the site N of the at least one SNP marker is carried out with a chip comprising the plurality of probes.

5. The method of claim 4, wherein the probes are shown as SEQ ID NO. 56, 57, 66, 67, 88, 89, 90, 91, 94, 95, 102, 103, 104, 105, 110, 111, 112, 113, 114, 115, 118, 119, 126, 127, 128, 129, 130, 131, 132 and 133.

6. The method of claim 1, wherein the detecting the presence of the genotype at the site N of the at least one SNP marker is carried out using the plurality of primers.

7. The method of claim 6, wherein the primers are chosen from SEQ ID NO. 136 and 137 for SNP marker NO.1; SEQ ID NO. 138 and 139 for SNP marker NO.2; SEQ ID NO. 140 and 141 for SNP marker NO.3; SEQ ID NO. 142 and 143 for SNP marker NO.4; SEQ ID NO. 144 and 145 for SNP marker NO.5; SEQ ID NO. 146 and 147 for SNP marker NO.6, 7 or 8; SEQ ID NO. 148 and 149 for SNP marker NO.9; SEQ ID NO. 150 and 151 for SNP marker NO.10; SEQ ID NO. 152 and 153 for SNP marker NO.11; SEQ ID NO. 154 and 155 for SNP marker NO.12; SEQ ID NO. 156 and 157 for SNP marker NO.13; SEQ ID NO. 158 and 159 for SNP marker NO.14; SEQ ID NO. 160 and 161 for SNP marker NO.15; SEQ ID NO. 162 and 163 for SNP marker NO.16; SEQ ID NO. 168 and 169 for SNP marker NO.19; SEQ ID NO. 170 and 171 for SNP marker NO.20; SEQ ID NO. 172 and 173 for SNP marker NO.21; SEQ ID NO. 174 and 175 for SNP marker NO.22; SEQ ID NO. 176 and 177 for SNP marker NO.23; SEQ ID NO. 178 and 179 for SNP marker NO.24; SEQ ID NO. 180 and 181 for SNP marker NO.25; SEQ ID NO. 182 and 183 for SNP marker NO.26; SEQ ID NO. 186 and 187 for SNP marker NO.28; SEQ ID NO. 188 and 189 for SNP marker NO.29; SEQ ID NO. 190 and 191 for SNP marker NO.30; SEQ ID NO. 192 and 193 for SNP marker NO.31; SEQ ID NO. 194 and 195 for SNP marker NO.32; SEQ ID NO. 196 and 197 for SNP marker NO.33; SEQ ID NO. 198 and 199 for SNP marker NO.34; SEQ ID NO. 200 and 201 for SNP marker NO.35; SEQ ID NO. 202 and 203 for SNP marker NO.36; SEQ ID NO. 204 and 205 for SNP marker NO.37; SEQ ID NO. 206 and 207 for SNP marker NO.38; SEQ ID NO. 208 and 209 for SNP marker NO.39; SEQ ID NO. 210 and 211 for SNP marker NO.40; SEQ ID NO. 212 and 213 for SNP marker NO.41; SEQ ID NO. 214 and 215 for SNP marker NO.42; SEQ ID NO. 216 and 217 for SNP marker NO.43; SEQ ID NO. 218 and 219 for SNP marker NO.44; and/or SEQ ID NO. 220 and 221 for SNP marker NO.45.

8. The method of claim 1, wherein the detecting is carried out by hybridization.

9. The method of claim 1, wherein the detecting is performed using sequencing.

10. The method of claim 9, wherein said sequencing is chosen from PCR, Real-time Quantitative PCR, and MassARRAY.

* * * * *